US010688198B2

(12) United States Patent
Ray et al.

(10) Patent No.: US 10,688,198 B2
(45) Date of Patent: Jun. 23, 2020

(54) SALICYLIC ACID-BASED POLYMERIC CEST CONTRAST AGENTS TARGETING PROSTATE-SPECIFIC MEMBRANE ANTIGEN AND USES THEREOF

(71) Applicant: THE JOHNS HOPKINS UNIVERSITY, Baltimore, MD (US)

(72) Inventors: Sangeeta Ray, Ellicott City, MD (US); Xing Yang, Baltimore, MD (US); Xiaolei Song, Baltimore, MD (US); Michael T. McMahon, Columbia, MD (US); Martin G. Pomper, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/764,316

(22) PCT Filed: Sep. 29, 2016

(86) PCT No.: PCT/US2016/054425
§ 371 (c)(1),
(2) Date: Mar. 28, 2018

(87) PCT Pub. No.: WO2017/059060
PCT Pub. Date: Apr. 6, 2017

(65) Prior Publication Data
US 2018/0264143 A1    Sep. 20, 2018

Related U.S. Application Data

(60) Provisional application No. 62/235,080, filed on Sep. 30, 2015.

(51) Int. Cl.
*A61K 49/00* (2006.01)
*A61K 49/08* (2006.01)
*C07F 5/00* (2006.01)
*C07F 19/00* (2006.01)
*C07F 1/04* (2006.01)
*C08F 222/38* (2006.01)
*A61K 49/12* (2006.01)
*C07F 5/02* (2006.01)
*A61K 51/06* (2006.01)
*A61K 49/14* (2006.01)

(52) U.S. Cl.
CPC ...... *A61K 49/0043* (2013.01); *A61K 49/0032* (2013.01); *A61K 49/0054* (2013.01); *A61K 49/085* (2013.01); *A61K 49/124* (2013.01); *A61K 49/146* (2013.01); *A61K 51/065* (2013.01); *C07F 1/04* (2013.01); *C07F 5/00* (2013.01); *C07F 5/003* (2013.01); *C07F 5/02* (2013.01); *C07F 19/00* (2013.01); *C08F 222/38* (2013.01); *A61K 49/0039* (2013.01); *A61K 2123/00* (2013.01)

(58) Field of Classification Search
CPC ......... A61K 49/00; A61K 49/08; A61K 49/12
See application file for complete search history.

(56) References Cited

U.S. PATENT DOCUMENTS

| 4,622,389 A | 11/1986 | Nagasawa et al. |
| 2003/0219780 A1 | 11/2003 | Olejnik et al. |

FOREIGN PATENT DOCUMENTS

| WO | WO 2009/002529 | 12/2008 |
| WO | WO 2009/070302 | 6/2009 |
| WO | WO 2014/186737 | 11/2014 |

OTHER PUBLICATIONS

Xing Yang et al., Salicylic Acid and Analogues as diaCEST MRI Contrast Agents with Highly Shifted Exchangeable Proton Frequencies, Angew. Chem. Int. Ed. 52, 8116-8119. (Year: 2013).*
Airan et al., MIR biosensor for protein kinase A encoded by a single synthetic gene. Magn Reson Med. 2012 Dec;68(6):1919-23.
Cai et al., Magnetic resonance imaging of glutamate. Nat Med. 2012 Jan 22;18(2):302-6.
Caravan, Strategies for increasing the sensitivity of gadolinium based MRI contrast agents. Chem Soc Rev. Jun. 2006;35(6):512-23.
Chan et al., Natural D-glucose as a biodegradable MRI contrast agent for detecting cancer. Magn Reson Med. Dec. 2012;68(6):1764-73.
Hancu et al., CEST and PARACEST MR contrast agents. Acta Radiol. Oct. 2010;51(8):910-23.
Haris et al., MICEST: a potential tool for non-invasive detection of molecular changes in Alzheimer's disease. J Neurosci Methods. Jan. 15, 2013;212(1):87-93.
Hyman et al., Probing oxidative stress: Small molecule fluorescent sensors of metal ions, reactive oxygen species, and thiols. Coord Chem Rev. Oct. 1, 2012;256(1920):2333-2356.
Jin et al., Spin-locking versus chemical exchange saturation transfer MRI for investigating chemical exchange process between water and labile metabolite protons.Magn Reson Med. May 2011;65(5):1448-60.
Kiess et al., Prostate-specific membrane antigen as a target for cancer imaging and therapy. QJ Nucl Med Mol Imaging. Sep. 2015;59(3):241-68.
Ling et al., PAssessment of glycosaminoglycan concentration in vivo by chemical exchange-dependent saturation transfer (gagCEST). Proc Natl Acad Sci U S A. Feb. 19, 2008;105(7):2266-70.
Liu et al., Nuts and bolts of chemical exchange saturation transfer MRI. NMR Biomed. Jul. 2013;26(7):810-28.
Liu et al., High-Throughput Screening of Chemical Exchange Saturation Transfer MR Contrast Agents. Con. Media. & Mol. Imag. 2010; 5(3): 162-170.

(Continued)

*Primary Examiner* — Michael G. Hartley
*Assistant Examiner* — Jagadishwar R Samala
(74) *Attorney, Agent, or Firm* — Casimir Jones, S.C.; Jeffrey W. Childers

(57) ABSTRACT

Salicylic acid-based polymeric CEST contrast agents targeting prostate-specific membrane antigen, pharmaceutical composition comprising the same and methods of use thereof are disclosed.

40 Claims, 13 Drawing Sheets
(6 of 13 Drawing Sheet(s) Filed in Color)

(56) References Cited

OTHER PUBLICATIONS

Longo et al., Iopamidol as a responsive MRI-chemical exchange saturation transfer contrast agent for pH mapping of kidneys: In vivo studies in mice at 7 T. Magn. Reson. Med. 2011;65(1):202-211.
McMahon et al.,New "multicolor" polypeptide diamagnetic chemical exchange saturation transfer (DIACEST) contrast agents for MRI. Magn Reson Med. Oct. 2008;60(4):803-12.
Que et al., Responsive magnetic resonance imaging contrast agents as chemical sensors for metals in biology and medicine. Chem Soc Rev. Jan. 2010;39(1):51-60.
Salhotra et al., Amide proton transfer imaging of 9L gliosarcoma and human glioblastoma xenografts. NMR Biomed. Jun. 2008;21(5):489-97.
Schmeltzer et al.Synthesis and Characterization of Salicylic Acid-Based Poly(Anhydride-Ester) Copolymers. J Bioact Compat Polym. Mar. 2006;21(2):123-133.
Sherry et al., Chemical exchange saturation transfer contrast agents for magnetic resonance imaging. Annu Rev Biomed Eng. 2008;10:391-411.
Terreno et al., Encoding the frequency dependence in MRI contrast media: the emerging class of CEST agents. Contrast Media Mol Imaging. Mar.-Apr. 2010;5(2):78-98.
Torrealdea et al., Contrast Media Mol. Imaging 2013 doi: 10.1002/cmmi.1522.
Van Zijl et al., Chemical exchange saturation transfer (CEST): what is in a name and what isn't? Magn. Reson. Med. 2011;65(4):927-948.
Van Zijl et al., MRI detection of glycogen in vivo by using chemical exchange saturation transfer imaging (glycoCEST). Proc Natl Acad Sci U S A. Mar. 13, 2007;104(11):4359-64.
Ward et al., JA new class of contrast agents for MRI based on proton chemical exchange dependent saturation transfer (CEST). J Magn Reson. Mar. 2000;143(1):79-87.
Yang et al., Salicylic acid and analogues as diaCEST MRI contrast agents with highly shifted exchangeable proton frequencies. Angew Chem Int Ed Engl. 2013;52:8116-19.
International Search Report and Written Opinion for PCT/US2016/054425, dated Jan. 13, 2017, 12 pages.

* cited by examiner

|  | SR-IX-21-2 (SA-U) | SR-IX-21-3, 1 (SA-DOTA-U) | MAA-Cest-Urea (SA-T) | SR-IX-21-CEST no linker, (SA-DOTA-T), 2 | SR-IX-21-CEST long linker, SA-DOTA-Linker-T)3 | ZJ43 |
|---|---|---|---|---|---|---|
| EC50 | 0.64 µM | 0.42 µM | 1.63 nM | 1.26 nM | 0.50 nM | 9.16 nM |
| KI | 1.280e-007 µM | 8.484e-008 µM | 3.261e-010 nM | 2.518e-010 nM | 1.006e-010 nM | 1.831e-009 nM |
| 95% Confidence Intervals |  |  |  |  |  |  |
| Bottom | 803.3 to 941.5 | 850.1 to 951.2 | 869.6 to 947.1 | 926.9 to 999.6 | 937.7 to 974.6 | 938.8 to 1018 |
| Top | 1317 to 1392 | 1279 to 1340 | 1269 to 1379 | 1203 to 1297 | 1260 to 1317 | 1213 to 1295 |
| EC50 | 0.30 µM to 1.39 µM | 0.19 µM to 0.9 µM | 0.68 nM to 3.92 nM | 0.43 nM to 3.69 nM | 0.30 nM to 0.87 nM | 3.04 nM to 27 nM |
| $K_I$ | 0.05 µM to 0.277 µM | 0.04 µM to 0.188 µM | 0.14 nM to 0.78 nM | 0.09 nM to 0.74 nM | 0.06 nM to 0.174 nM | 0.6 nM to 5.5 nM |

*Fig. 10A*

SALICYLIC ACID-BASED POLYMERIC CEST CONTRAST AGENTS TARGETING PROSTATE-SPECIFIC MEMBRANE ANTIGEN AND USES THEREOF

CROSS-REFERENCE TO RELATED APPLICATIONS

This application is a 35 U.S.C. § 371 National Stage Entry of International Application No. PCT/US2016/054425 having an international filing date of Sep. 29, 2016, which claims the benefit of U.S. Provisional Application No. 62/235,080, filed Sep. 30, 2015, the contents of which are incorporated herein by reference in their entirety.

FEDERALLY SPONSORED RESEARCH OR DEVELOPMENT

This invention was made with government support under CA134675, CA148901 and EB015031 awarded by the National Institutes of Health. The government has certain rights in the invention.

BACKGROUND

The prostate-specific membrane antigen (PSMA) is a type II integral membrane protein that is abundantly expressed in prostate cancer and the endothelium of neovasculature in most solid tumors. PSMA is increasingly recognized as an important target for cancer imaging and therapy.

Over the past decade, a broad range of radiolabeled compounds have been synthesized for imaging and therapy of prostate and many other types of cancer and tumor neovasculature in combination with noninvasive imaging techniques, such as magnetic resonance imaging (MRI), which achieves high spatial and temporal resolution. The imaging probes for magnetic resonance imaging (MRI) are termed "contrast agents," since they enhance the water proton-based contrast between the imaging target and the surrounding tissue. Detection with MRI relies on contrast in the MRI signal between the tissue of interest and its surrounding tissue.

Recently, a new type of MRI contrast that relies on direct chemical exchange of protons with bulk water has been developed and is referred to as chemical exchange saturation transfer (CEST) MRI. CEST MRI is a technique in which concentration marker molecules are labeled by either saturating or labeling their exchangeable proton spins by radio-frequency (RF) irradiation. If such saturation or labeling can be achieved rapidly, i.e., before the spin exchanges, exchange of such labeled spins with water leads to transfer of the magnetization, allowing indirect detection of the solute via the water resonance through a change in signal intensity in MRI.

A variety of organic molecules possessing protons that exchange rapidly with the surrounding water protons have been suggested as new contrast agents. These exchangeable protons can be "magnetically tagged" using a radiofrequency saturation pulse applied at their resonance frequency. The tagged protons exchange with the protons of surrounding water molecules and consequently reduce the MRI signal. This effect in and of itself would not be visible at the low concentrations of solute, but the exchanged protons are replaced with fresh, unsaturated protons and the same saturation process is repeated. Over time (e.g., several seconds) this repetition results in signal amplification and very low concentrations of agents can be detected. Hence, these agents are termed CEST contrast agents.

Each CEST contrast agent can have a different saturation frequency, which depends on the chemical shift of the exchangeable spin. The magnitude of proton transfer enhancement (PTE) due to this effect, and the resulting signal reduction from equilibrium ($S_0$) to saturated ($S_{sat}$), are given by:

$$PTE = \frac{NM_w \alpha k_{ex}}{(1-x_{CA})R_{1wat} + x_{CA}k_{ex}} \cdot \{1 - e^{-[(1-x_{CA})R_{1wat} + x_{CA}k_{ex}]t_{sat}}\} \quad [\text{Eq. 1}]$$

and $$(1 - S_{sat}/S_0) = \frac{PTE \cdot [CA]}{2 \cdot [H_2O]}. \quad [\text{Eq. 2}]$$

wherein "CA" is the contrast agent containing multiple exchangeable protons, $x_{CA}$ is its fractional exchangeable proton concentration, $\alpha$ is the saturation efficiency, k is the pseudo first-order rate constant, N is the number of exchangeable protons per molecular weight unit, and $M_w$ is the molecular weight of the CA. The exponential term describes the effect of back exchange and water longitudinal relaxation ($R_{1wat}=1/T_{1wat}$) on the transfer during the RF saturation period ($t_{sat}$). This effect will be larger when spins exchange faster, but, under such conditions, saturation must occur faster, as well, which increases the radio-frequency power needed. In addition, the resonance of the particular spins must be well separated from the bulk in the NMR spectrum, which requires a slow exchange on the NMR time scale. This condition means that the frequency difference of the exchangeable spins with the bulk is much larger than the exchange rate ($\Delta\omega > k$).

Thus, the CEST technology becomes more applicable at higher magnetic fields or when using paramagnetic shift agents. Any molecule that exhibits a significant PTE effect can be classified as a CEST (contrast) agent. The concept of these agents as MR contrast agents is somewhat similar to the chemical amplification of colorimetric labels in in situ gene expression assays. For instance, CEST agents can be detected by monitoring the water intensity as a function of the saturation frequency, leading to a so-called Z-spectrum. In such spectra, the saturation effect of the contrast agent on the water resonance is displayed as a function of irradiation frequency.

Since the first report of CEST contrast in 2000, CEST MR imaging has become a widely used MRI contrast mechanism, and CEST contrast is generated by the dynamic exchange process between an exchangeable proton of a biomarker of interest and the surrounding water protons. To detect the biomarkers, the magnetization of some of their exchangeable protons is nullified by applying a selective radiofrequency saturation pulse at the specific resonance frequency (chemical shift) of the target protons. Due to exchange of the "saturated" agent protons with surrounding water protons, the net water signal is reduced, thus enhancing the MRI contrast.

CEST contrast agents have many advantages, such as lower toxicity due to the absence of lanthanide metals, ease of modification, and clearance through breakdown during natural biochemical processes. However, currently reported organic CEST agents suffer from sensitivity drawbacks, however, especially due to a small chemical shift difference between exchangeable proton and water. There are many challenges with respect to detecting CEST contrast agents, such as low spatial/temporal resolution, artifacts and low contrast-noise-ratio, and difficulties separating CEST contrast from other sources of water signal loss. Therefore, there remains a need for the design and development of MRI contrast agents that offer improved sensitivity and contrast effects in producing MR images.

SUMMARY

In some aspects, the presently disclosed subject matter provides a compound of formula (I), formula (II), formula (III), or formula (IV):

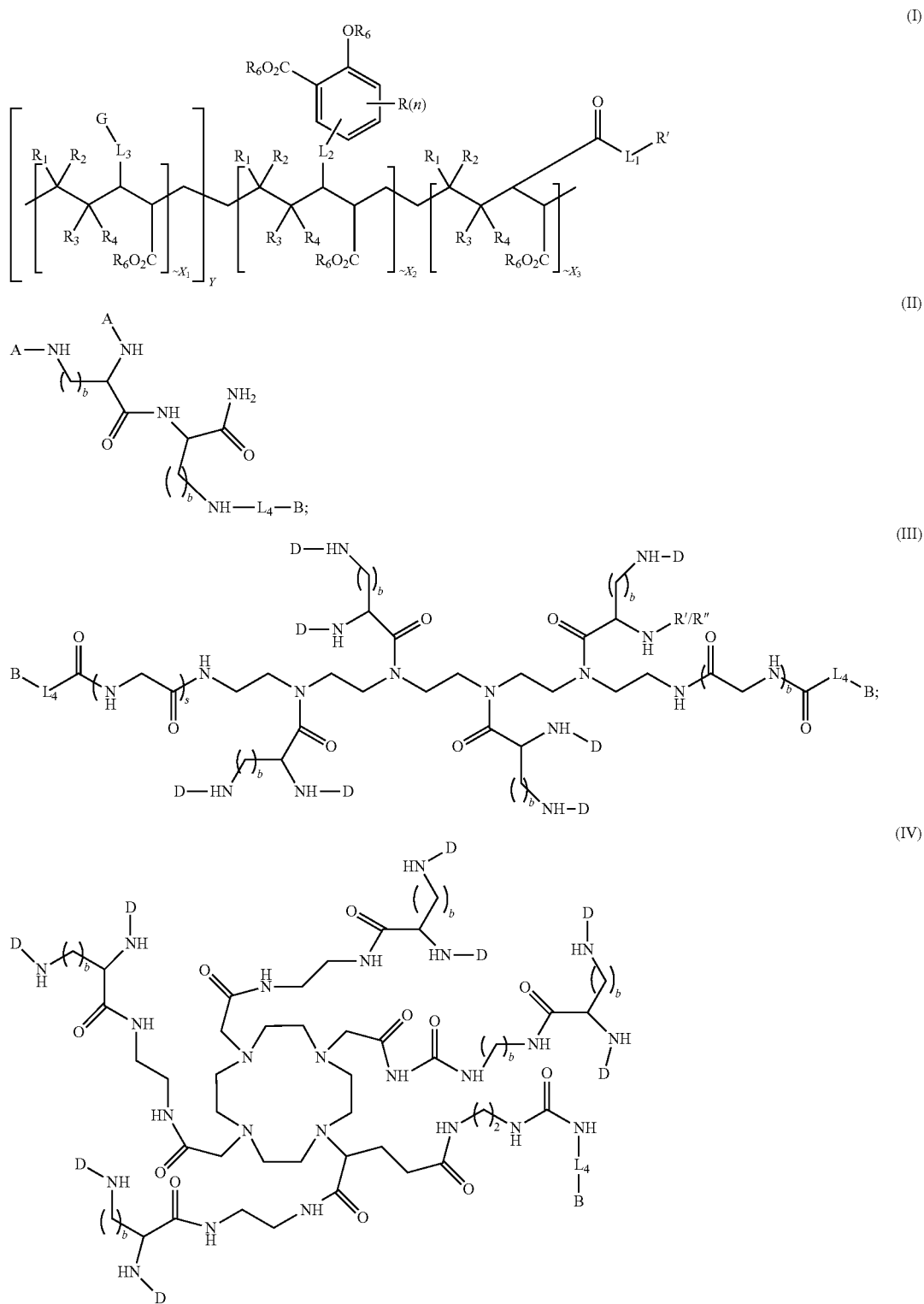

wherein:
R' is

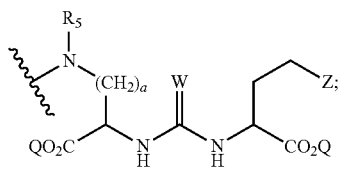

B is R' or

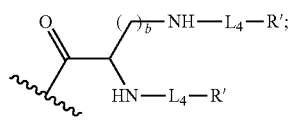

Z is tetrazole or CO$_2$Q; Q is H or a protecting group; W is O or S; a is an integer selected from the group consisting of 0, 1, 2, 3 and 4; b is an integer selected from the group consisting of 1, and 4; n is independently an integer selected from the group consisting of 0, 1, 2, and 3; s is an integer selected from the group consisting of 0, 1, 2, 3 and 4; each R is independently selected from the group consisting of hydrogen, substituted or unsubstituted alkyl, alkoxyl, hydroxyl, hydroxyalkyl, carboxyl, acyl, carbonyl, carbamoyl, alkylcarbamoyl, halogen, amino, alkylamino, nitro, nitrile, amide, haloalkyl, aryl, cycloalkyl, aralkyloxyl, and —SO$_3$H; R$_1$, R$_2$, R$_3$ and R$_4$ are independently selected from the group consisting of H or substituted or unsubstituted linear or branched alkyl, substituted or unsubstituted aryl, and alkoxyl; R$_5$ is independently H, C$_1$-C$_4$ alkyl or C$_2$-C$_{12}$ aryl; each R$_6$ is independently H, Na or a protecting group; L$_1$ is a linking group selected from the group consisting of —(CH$_2$)$_m$—, —(CH$_2$—CH$_2$—O)$_t$—, —(O—CH$_2$—CH$_2$)$_t$—, —NR$_7$—(CHR$_8$)$_m$—NR$_7$—C(=O)—(CH$_2$)$_m$—C(=O)— and —NR$_7$—(CHR$_8$)$_m$—C(=O)—NR$_7$—(CH$_2$)$_m$—C(=O)—; L$_2$ is a linking group selected from the group consisting of —(CH$_2$)$_m$—NR$_7$—C(=O)—(CH$_2$)$_p$—, —(CH$_2$)$_m$—C(=O)—NR$_7$—(CH$_2$)$_p$—, —(CH$_2$)$_m$—NR$_7$—C(=O)—NR$_7$—(CH$_2$)$_p$—, —(CH$_2$)$_m$—NR$_7$—C(=O)—NR$_7$—(CH$_2$)$_p$—, —(CH$_2$)$_m$—O—C(=O)—NR$_7$—, —(CH$_2$)$_m$—O—C(=O)—NR$_7$—(CH$_2$)$_p$—, —(CH$_2$)$_m$—NR$_7$—C(=O)—O—(CH$_2$)$_p$—, —(CH$_2$)$_m$—NR$_7$—C(=O)—O—(CH$_2$)$_p$—, —SO$_2$—NH—(CH$_2$)$_p$—, and —(CH$_2$)$_m$—SO$_2$—NH—(CH$_2$)$_p$—; L$_3$ is a linking group selected from the group consisting of —C(=O)—NR$_7$—(CH$_2$)$_m$—, —C(=O)—NR$_7$—(CH$_2$)$_m$—NR$_7$—, —C(=O)—NR$_7$—(CH$_2$)$_m$—C(=O)—NR$_7$—, —C(=O)—NR$_7$—(CH$_2$)$_m$—NR$_7$—C(=O)—, —C(=O)—NR$_7$—(CH$_2$)$_m$—NR$_7$—C(=O)—NR$_7$—, —C(=O)—NR$_7$—(CH$_2$)$_m$—NR$_7$—C(=O)—(CH$_2$)$_p$—, —C(=O)—NR$_7$—(CH$_2$)$_m$—C(=O)—NR$_7$—(CH$_2$)$_p$—, —C(=O)—NR$_7$—(CH$_2$)$_m$—(O—CH$_2$—CH$_2$)$_t$—, —C(=O)—NR$_7$—(CH$_2$)$_m$—(CH$_2$—CH$_2$—O)$_t$—(CH$_2$)$_p$—, and —C(=O)—NR$_7$—(CH$_2$)$_m$—(O—CH$_2$—CH$_2$)$_t$—C(=O)—NR$_7$—; L$_4$ is a linking group selected from the group consisting of —(CH$_2$)$_m$—, —C(=O)—(CH$_2$)$_m$—C(=O)—, —C(=O)—(CH$_2$)$_m$—NR$_7$—C(=O)—, —C(=O)—(CH$_2$—CH$_2$—O)$_t$—C(=O)—, —C(=O)—(CHR$_8$)$_m$—C(=O)—, —C(=O)—(CHR$_8$)$_m$—NR$_7$—C(=O)—, —C(=O)—(CH$_2$—CH$_2$—O)t-C(=O)—, and —C(=O)—(O—CH$_2$—CH$_2$)$_t$—C(=O)—;

each R$_7$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; each R$_8$ is independently selected from the group consisting of hydrogen, and —COOR$_6$; m and p are each independently an integer selected from the group consisting of 0, 1, 2, 3, 4, 5, 6, 7 and 8; t is an integer selected from the group consisting of 1, 2, 3, 4, 5, 6, 7, 8, 9, 10, 11 and 12; Y is an integer selected from the group consisting of 0 and 1; G is an azide, an alkyne, a fluorescent dye moiety that emits light in the visible or near-infrared (NIR) spectrum, or a chelating moiety optionally comprising a metal or a radiometal; X$_1$ is an integer selected from the group consisting of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and 2; X$_2$ and X$_3$ are each independently an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40; A is selected from the group consisting of:

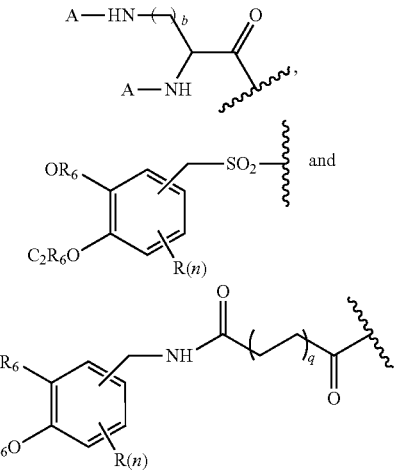

wherein q is an integer selected from the group consisting of 1, 2, 3, 4, and 5; D is selected from the group consisting of:

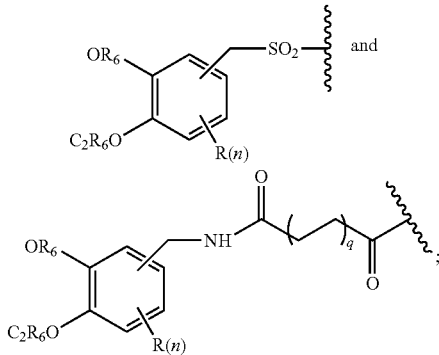

or a salt or a stereoisomer thereof.

In other aspects, the presently disclosed subject matter provides pharmaceutical compositions comprising a compound of formula (I), formula (II), formula (III), and/or formula (IV), and a pharmaceutically acceptable carrier, diluent or excipient.

In further aspects, the presently disclosed subject matter provides a method for producing a magnetic resonance imaging (MRI) of one or more PSMA-expressing tumors or cells, the method comprising contacting the one or more PSMA-expressing tumors or cells with an effective amount of a magnetic resonance imaging contrast agent; and imaging the target using a based MRI technique to produce the MR image of the one or more PSMA-expressing tumors or cells, wherein the magnetic resonance imaging contrast agent is a compound of formula (I), formula (I), formula (II), formula (III), and/or formula (IV) or a pharmaceutical composition of any thereof.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
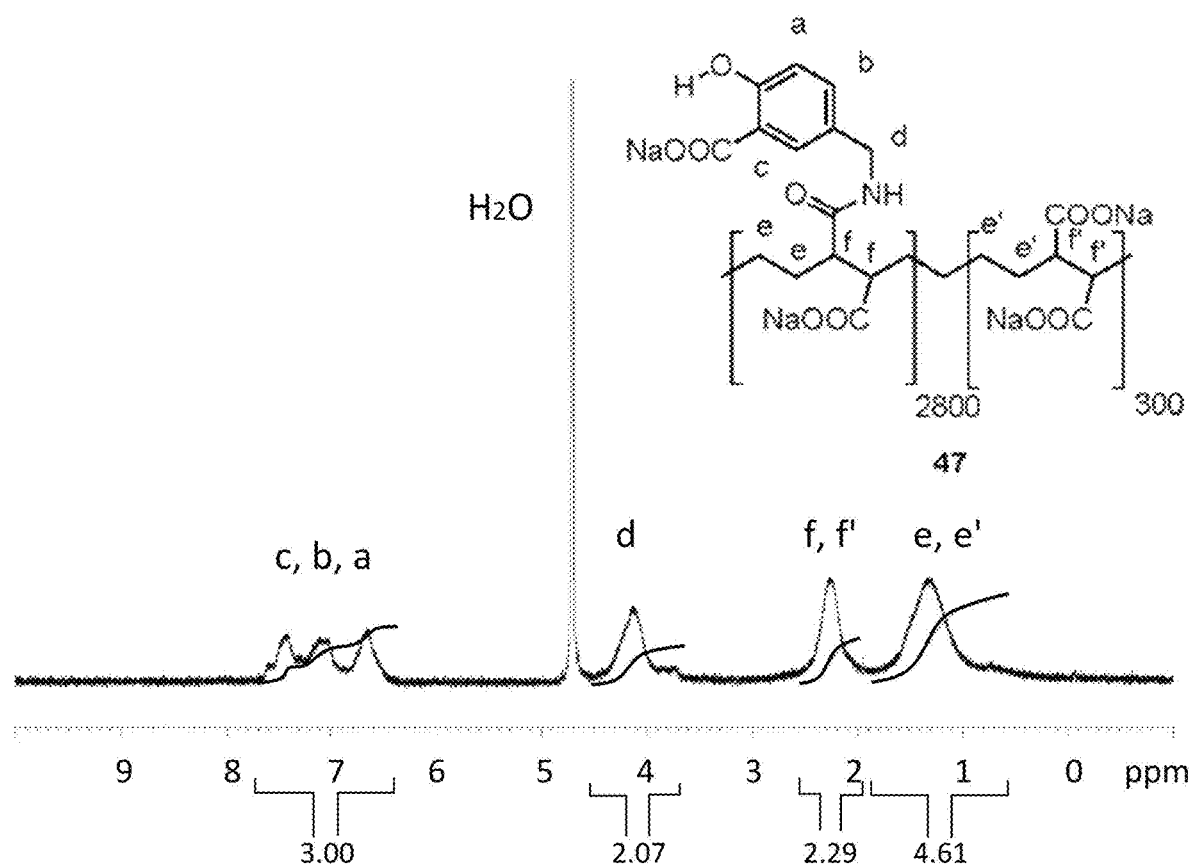
Figure 2:
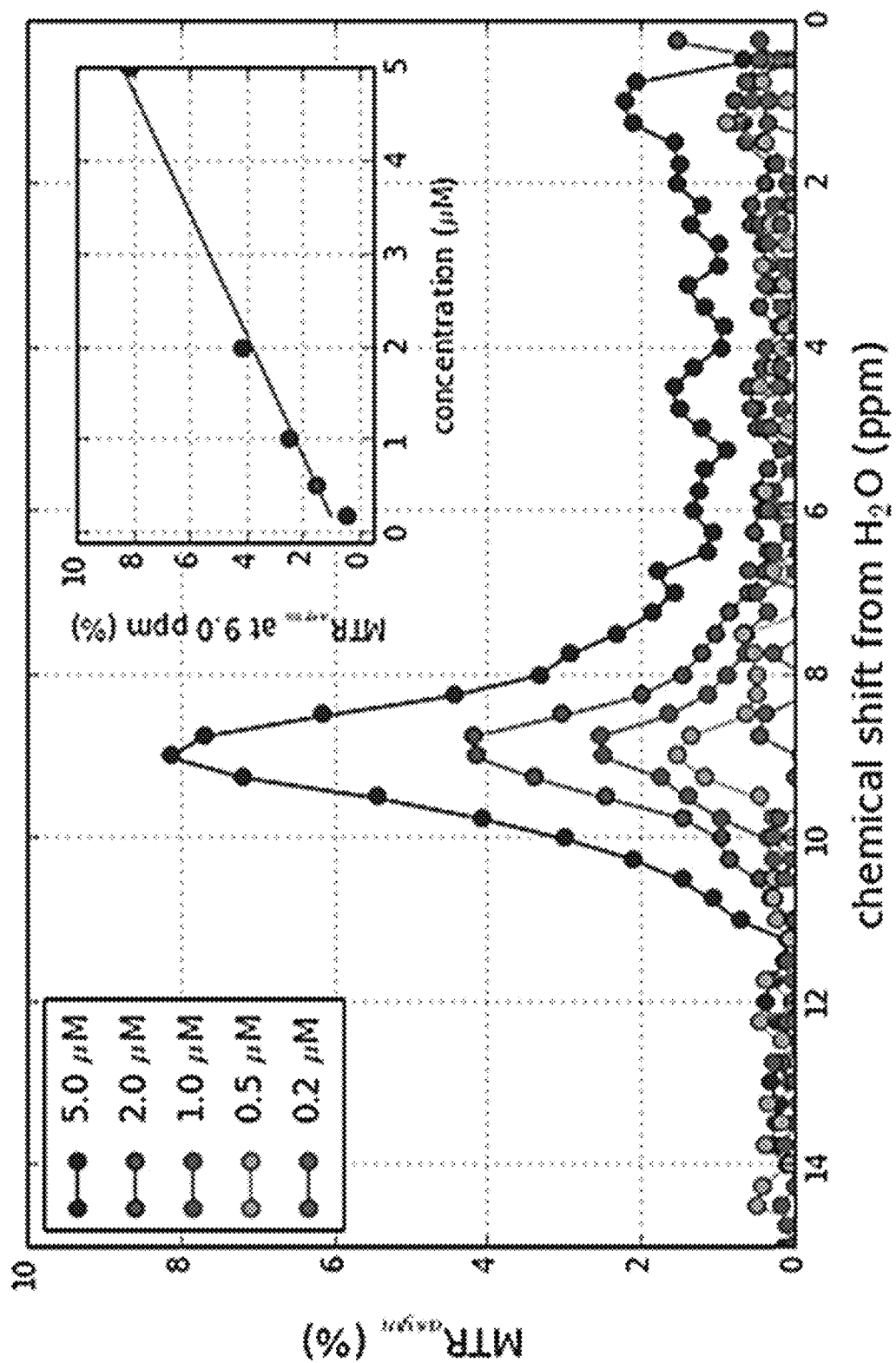
Figure 3:
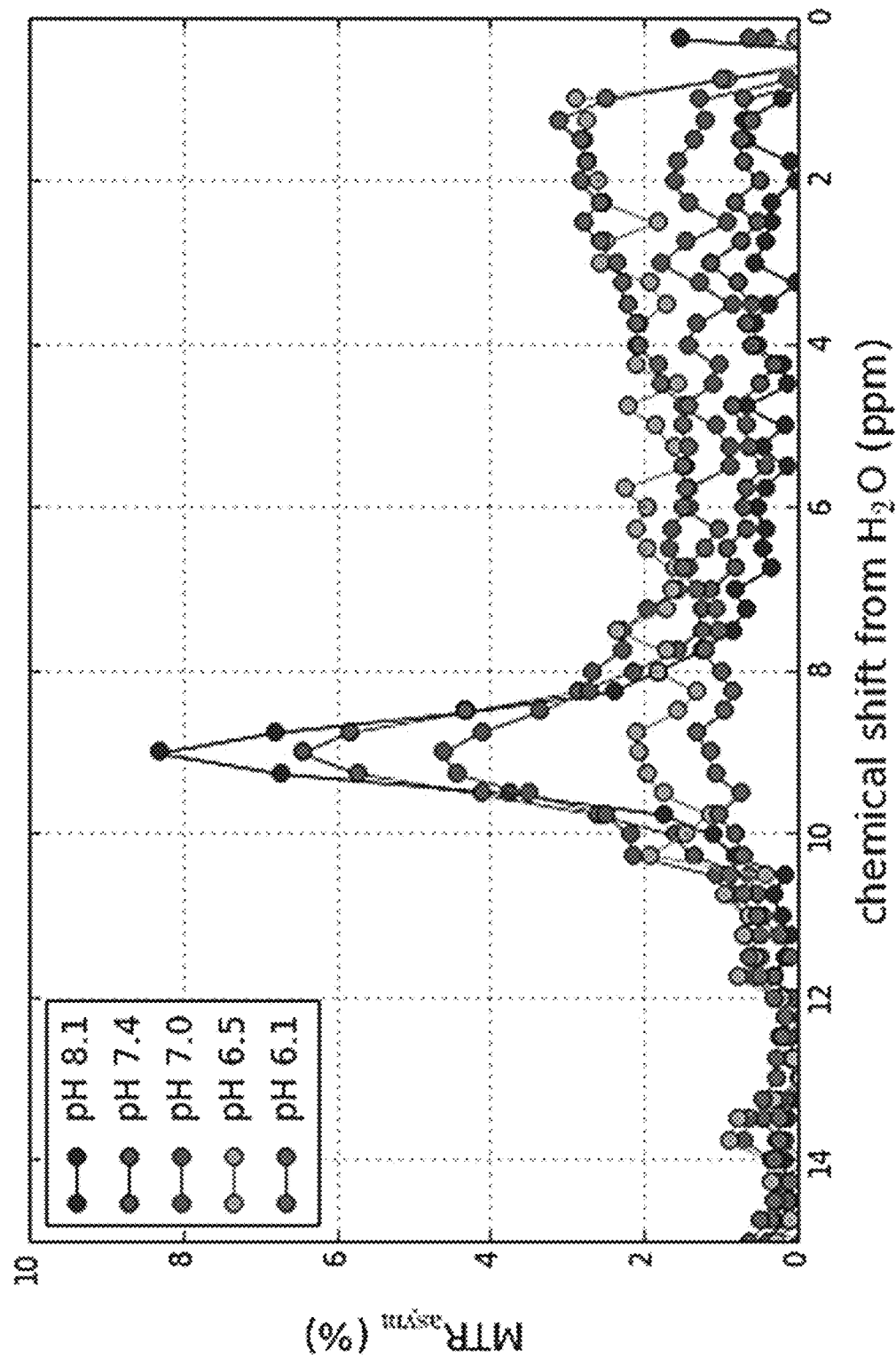
Figure 4:
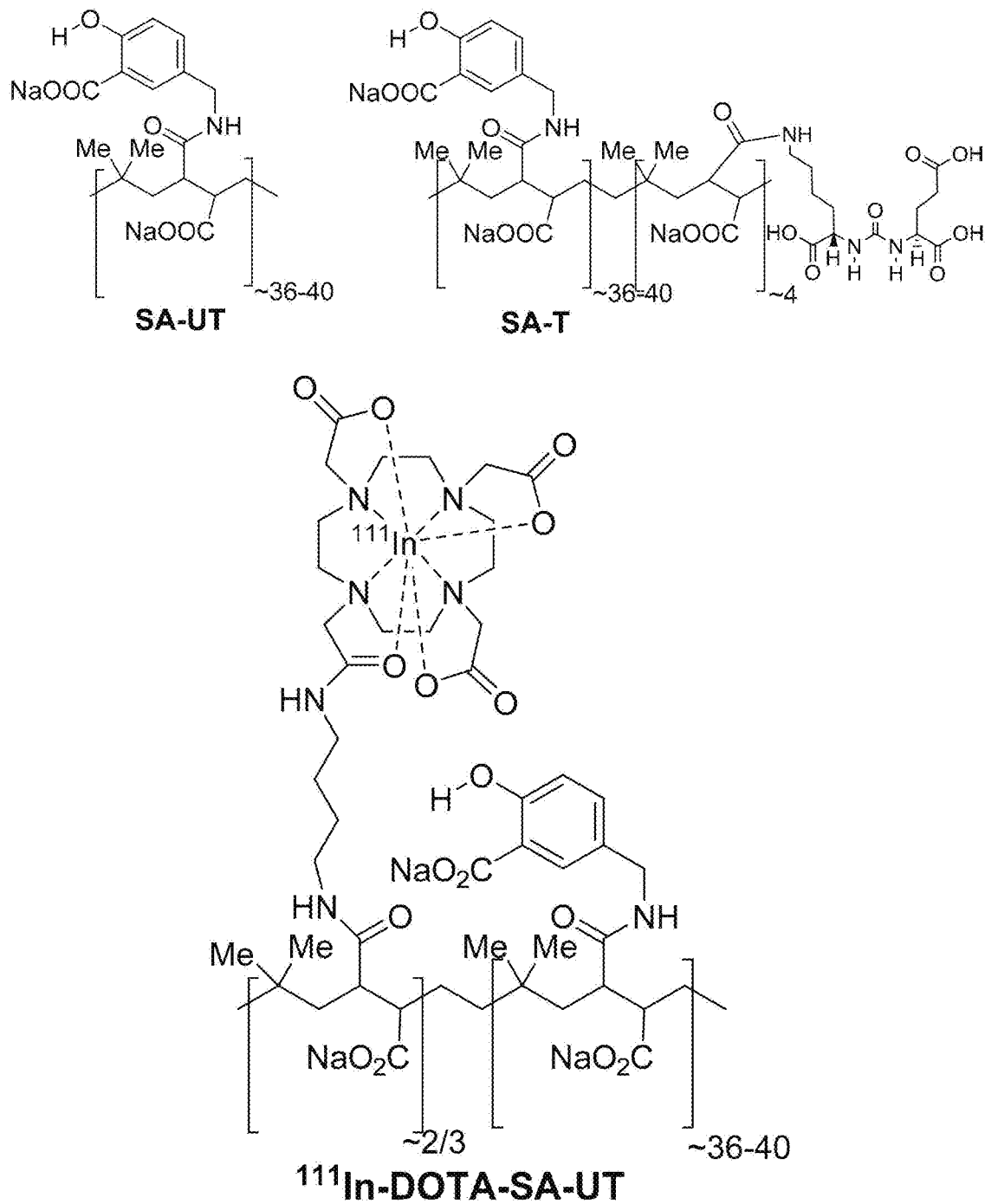
Figure 4:
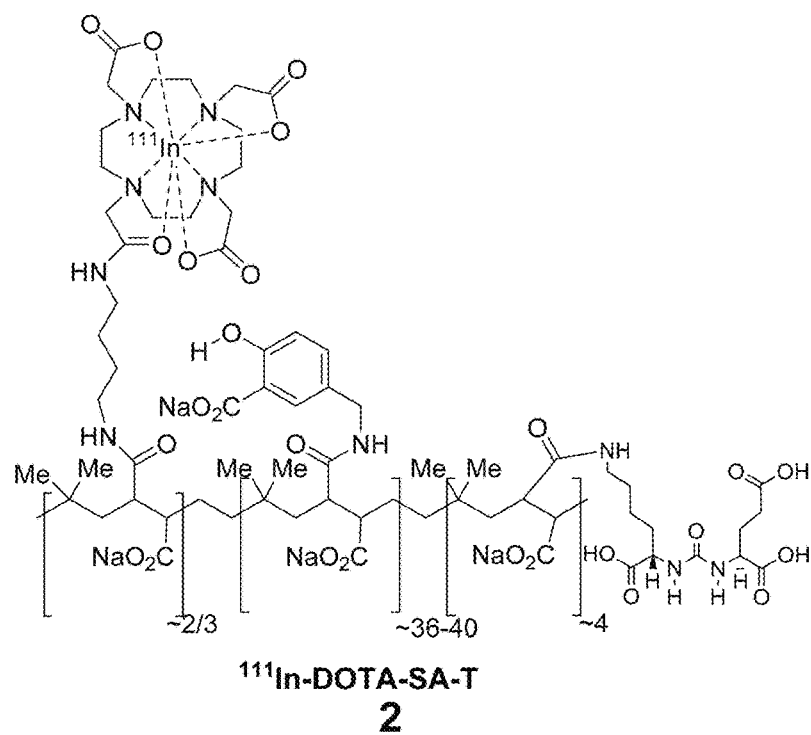
Figure 4:
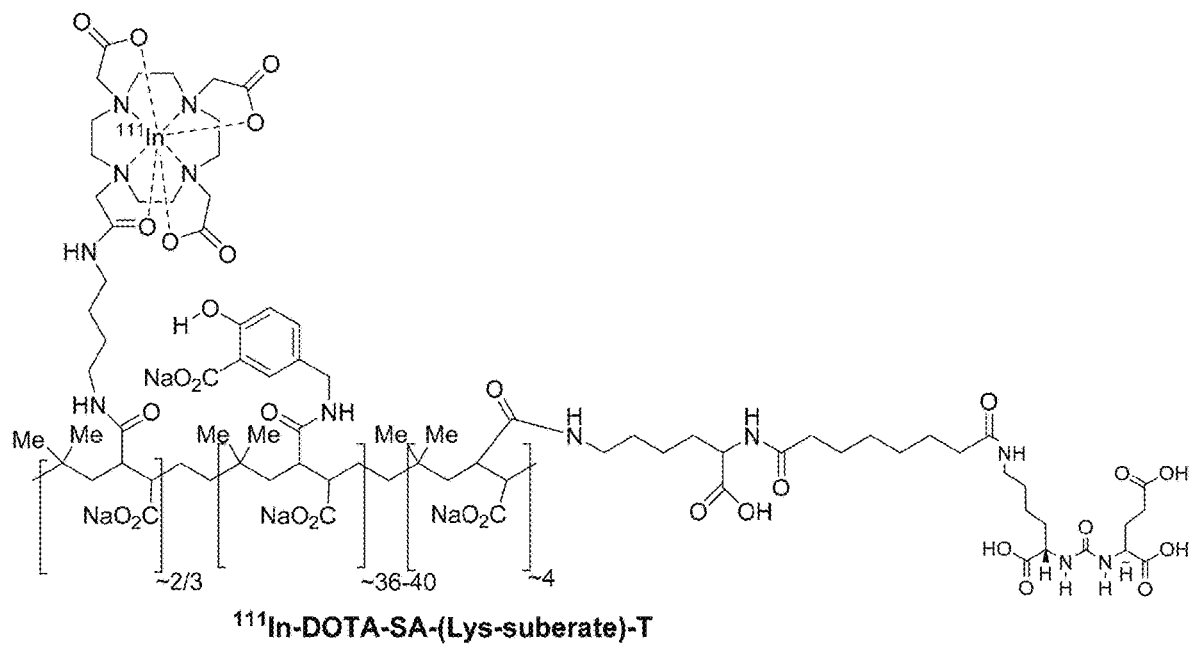
Figure 5A:
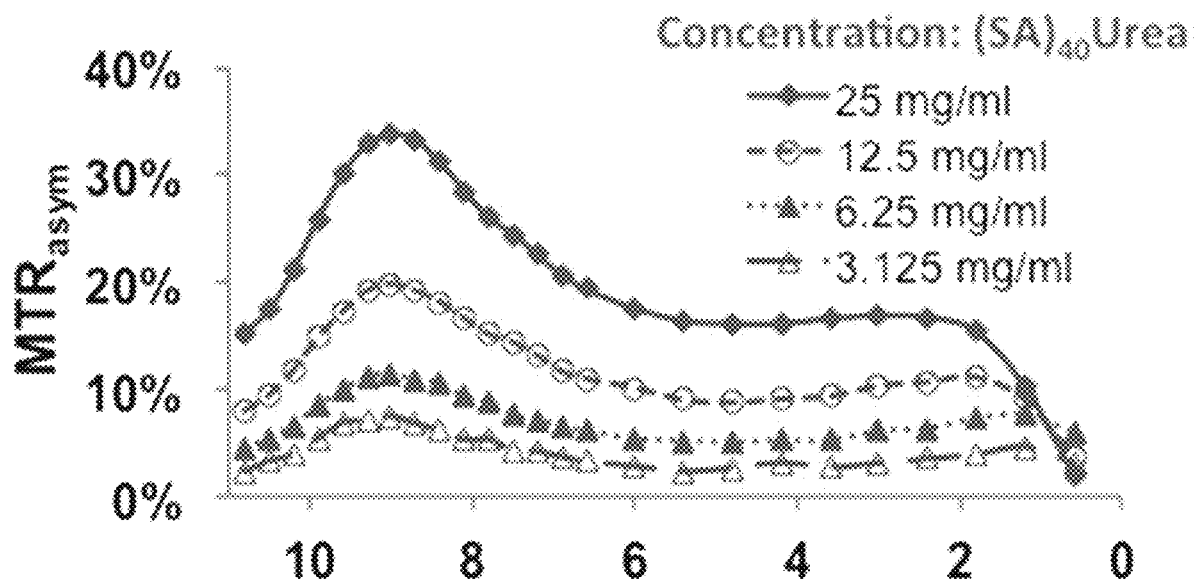
Figure 5B:
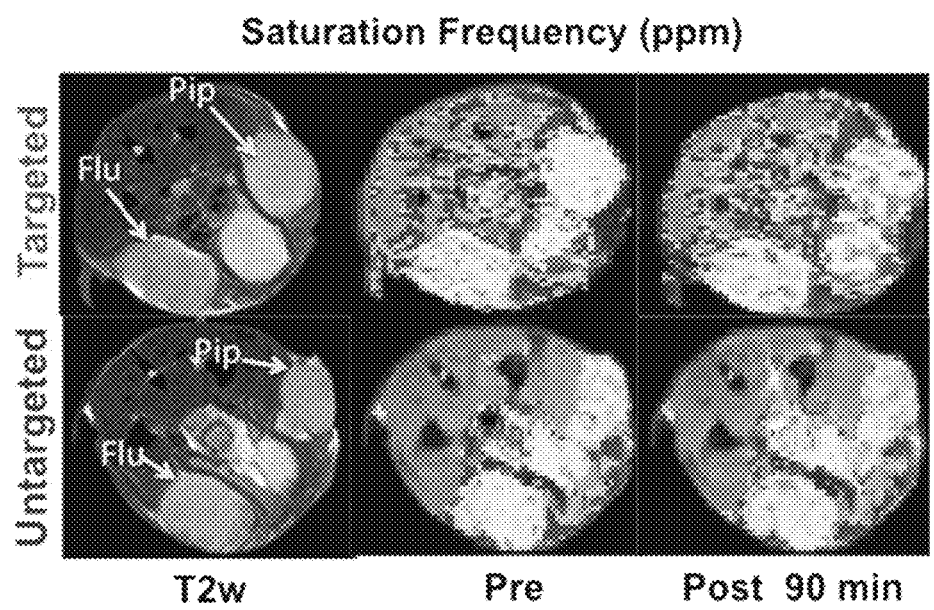
Figure 5C:
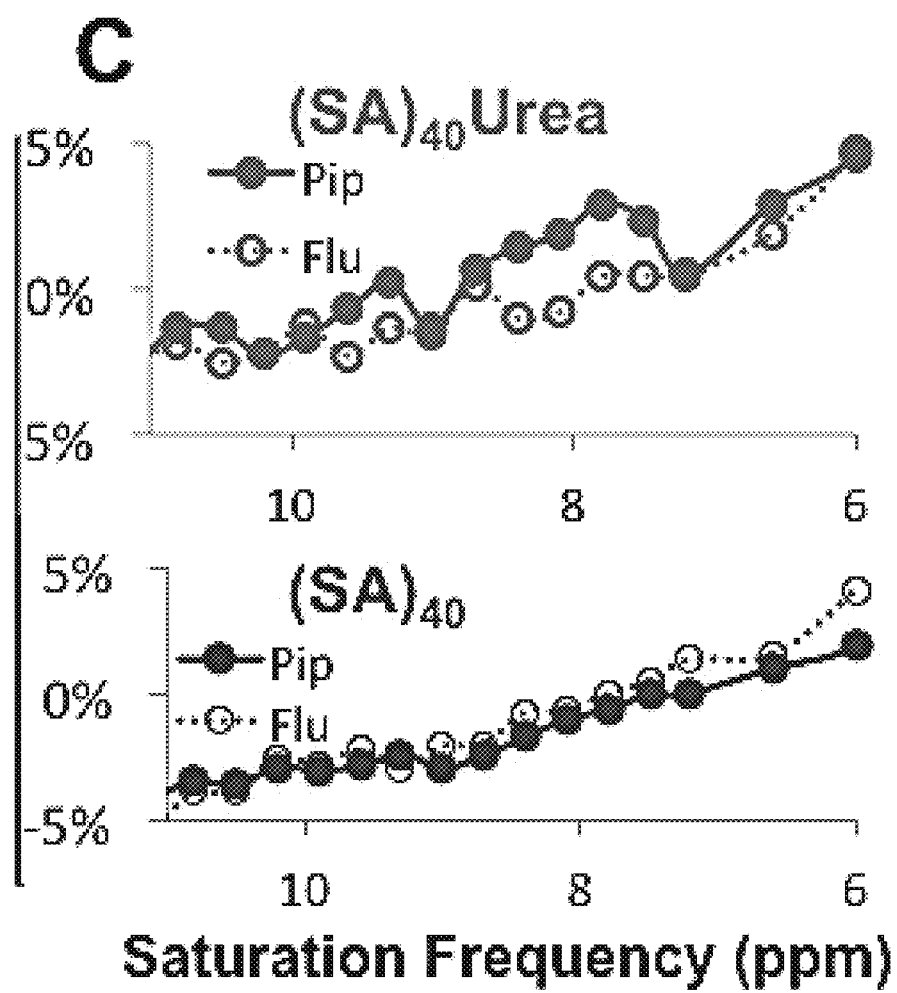
Figure 6:
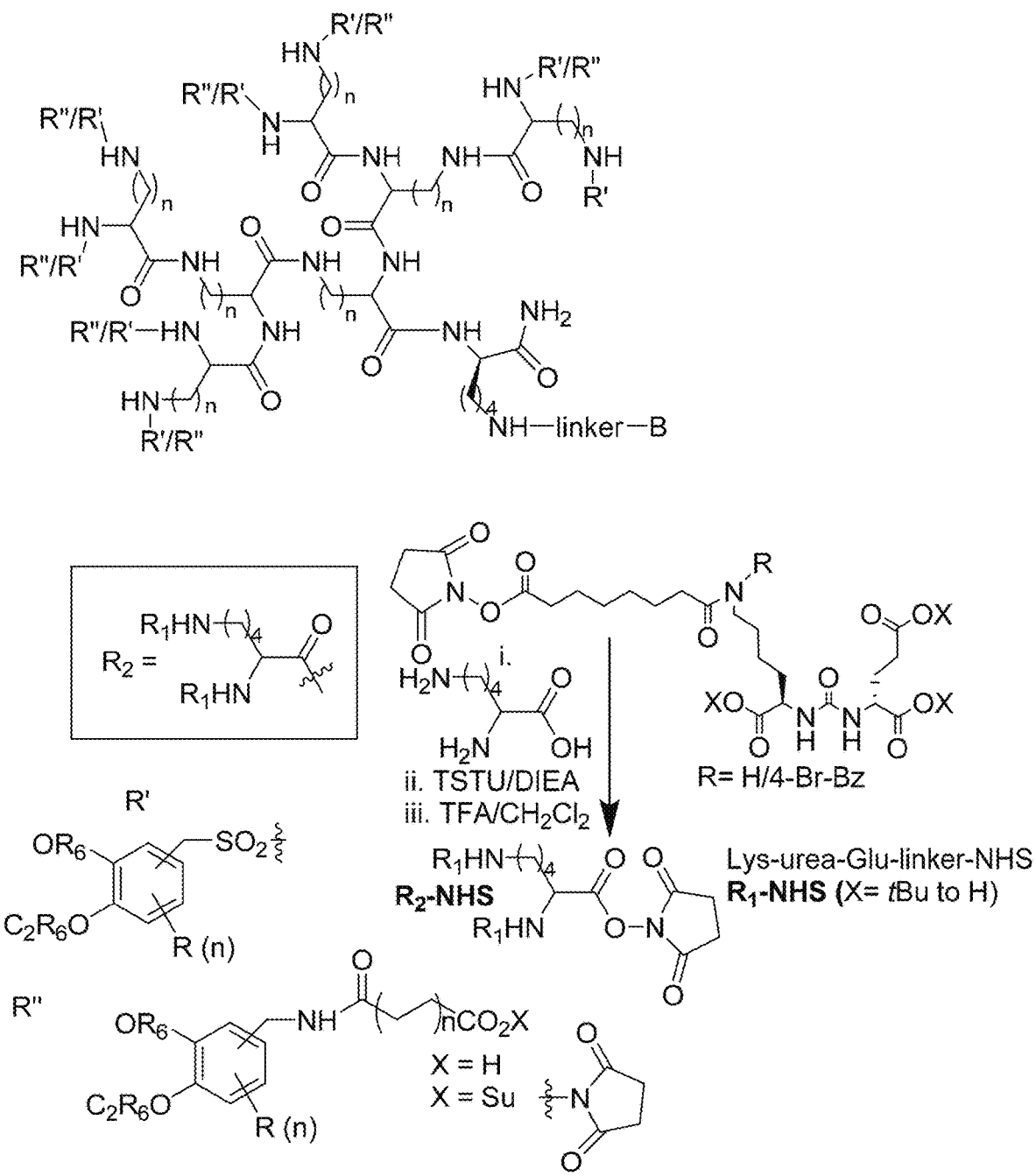
Figure 7:
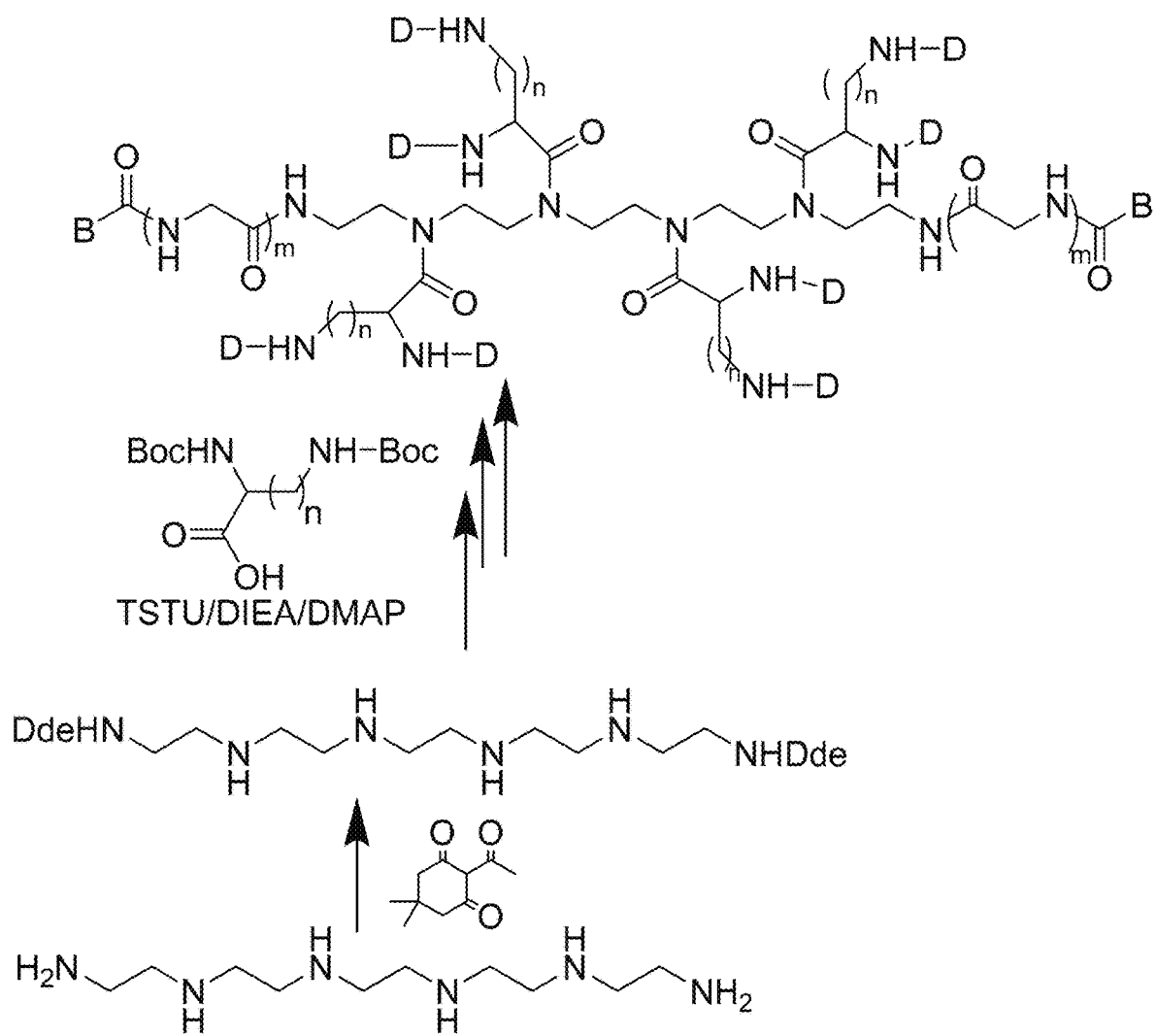
Figure 8:
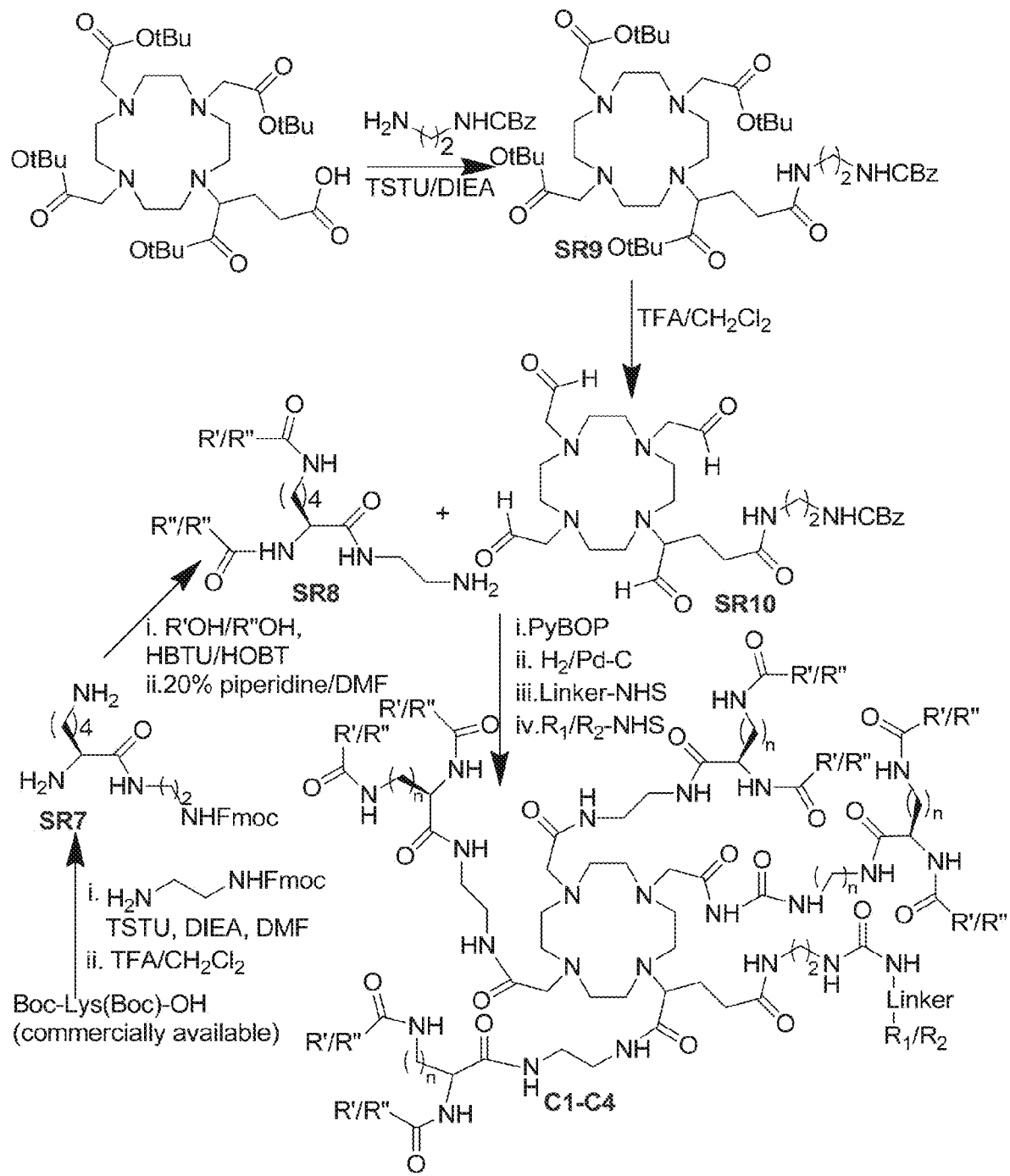
Figure 9A:
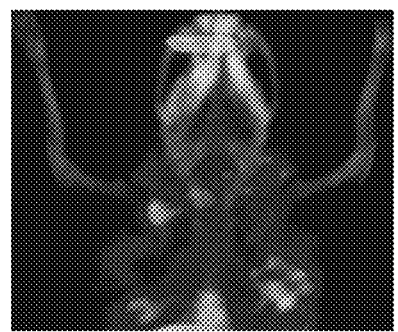
Figure 9D:
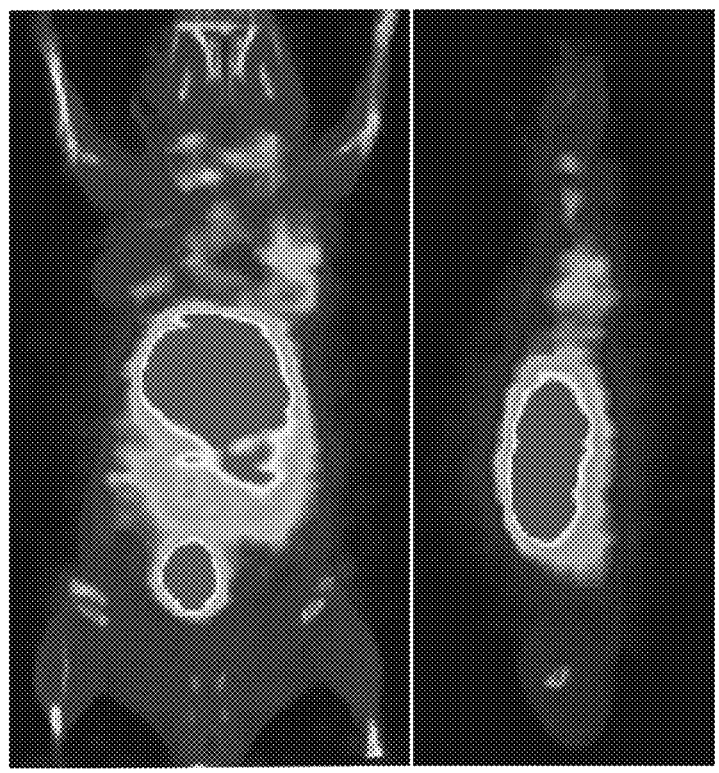
Figure 9D:
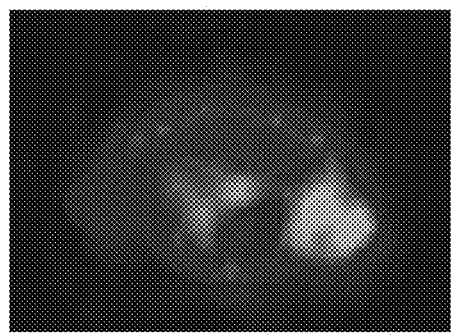
Figure 10B:
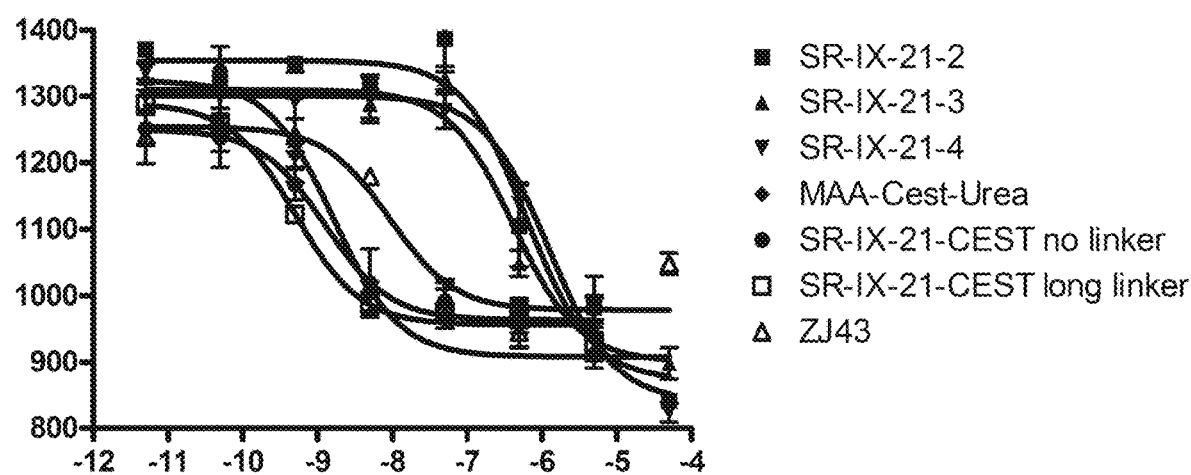

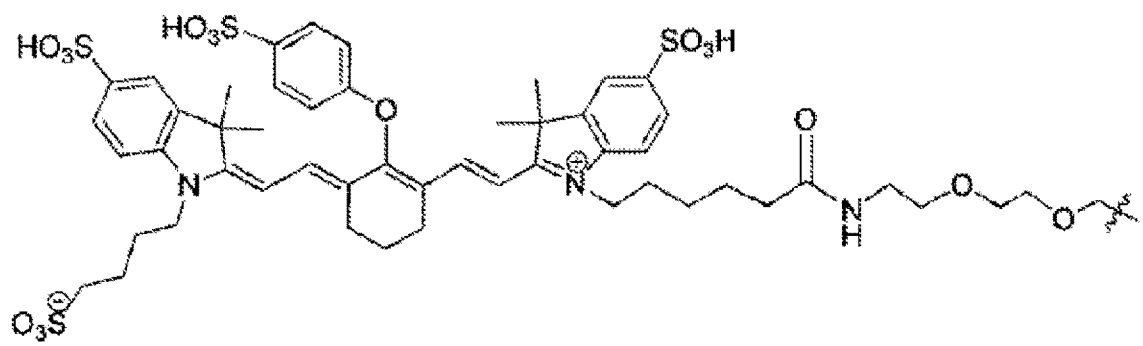

Having thus described the presently disclosed subject matter in general terms, reference will now be made to the accompanying Figures, which are not necessarily drawn to scale, and wherein:

FIG. 1 shows the H-NMR spectrum of polymer 47 in $D_2O$;

FIG. 2 shows CEST contrast of the polymer 47 at micromolar level;

FIG. 3 shows pH dependence of polymer 47;

FIG. 4 shows a representative structure of a salicylic acid (SA) analog grafted on a polymeric platform (SA-T) with a PSMA targeting moiety, and the structure of a control CEST copolymer (SA-UT) without a targeting moiety;

FIG. 5A, FIG. 5B, and FIG. 5C show: (FIG. 5A) a $MTR_{asym}$ spectrum that illustrates the in vitro characterization of SA-T PolyCEST at four concentrations of the targeted SA-T polymeric diaCEST agent for PSMA-targeted probe; (FIG. 5B) in vivo CEST MR images showing the PSMA+ PIP and PSMA− flu tumors after injection of both targeted (($SA)_{40}$-Urea) and untargeted (($SA)_{40}$) CEST polymers. The CEST imaging process consists of three components, image collection, WASSR correction, and CNR filtering and contour leveling; and (FIG. 5C) $MTR_{asym}$ spectra for the regions of interest drawn over the whole tumors 90 minutes post-injection of SA-T PolyCEST and the control test copolymer SA-UT;

FIG. 6 shows a synthetic scheme for the presently disclosed branched multimeric platform for contrast enhancement and PSMA targeting;

FIG. 7 shows a synthetic scheme for the presently disclosed linear multimeric platform for contrast enhancement and PSMA targeting;

FIG. 8 shows a synthetic scheme for the presently disclosed cyclic multimeric platform for contrast enhancement and PSMA targeting;

FIG. 9A, FIG. 9B, FIG. 9C, and FIG. 9D show (FIG. 9A) 3D volume rendering followed by (FIG. 9B) 2D coronal, (FIG. 9C) sagittal and (FIG. 9D) axial view at 4 h post-injection of targeted polymer 3, $^{111}$In-DOTA-SA-Lys-suberate-T; and FIG. 10A and FIG. 10B show (FIG. 10A) the PSMA inhibitory activity and (FIG. 10B) the $IC_{50}$ curves for the compounds of the present invention and ZJ43, a known high affinity inhibitor.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Salicylic Acid-Based Polymeric CEST Contrast Agents Targeting Prostate-Specific Membrane Antigen and Uses Thereof Magnetic Resonance Imaging (MRI) has been widely used as a diagnostic tool to detect changes in soft tissue due to its exquisite spatial resolution. One of the standard methods to detect pathologies involves injection of a magnetic resonance (MR) contrast agent, such as the gadolinium (III) complexes routinely used for angiography (see, e.g., Caravan, *Chem. Soc. Rev.* (2006); Kubicek and Toth, *Advances in Inorganic Chemistry* (2009)). Chemical exchange saturation transfer (CEST) contrast agents are a new alternative, which have become popular due to the unique features of these agents (see, e.g., Hancu, et al., *Acta Radiol* (2010); Terreno, et al., *Contrast Media Mol. Imaging* (2010); Liu, et al., *NMR Biomed* (2013); van Zijl and Yadav, *Magn. Reson. Med.* (2011)).

One of the attractive features of CEST probes is that MR contrast can be produced by a variety of organic diamagnetic compounds possessing exchangeable protons with suitable proton transfer rates (Hancu, et al., *Acta Radiol* (2010); Terreno, et al., *Contrast Media Mol. Imaging* (2010); Liu, et al., *NMR Biomed* (2013); van Zijl and Yadav, *Magn. Reson. Med.* (2011)) such as, for example, glucose (see, e.g., Chan, et al., *Magn. Reson. Med.* (2012); Jin et al., *Magn. Reson. Med.* (2011); Torrealdea, et al., *Contrast Media Mol. Imaging* (2013)), glycogen (see, e.g., van Zijl, et al., *Proc. Natl. Acad. Sci.*), myoinositol (see, e.g., Hans, et al., *Neurosci. Meth.* (2013)), glutamate (see, e.g., Cai, et al., *Nat. Med.* (2012)), creatine (see, e.g., Hancu, et al., *Acta Radiol* (2010); Terreno, et al., *Contrast Media Mol. Imaging* (2010); Liu, et al., *NMR Biomed* (2013); van Zijl and Yadav, *Magn. Reson. Med.* (2011)), L-arginine (see, e.g., Ward, et al., *J. Magn. Reson.* (2000)), glycosaminoglycans (see, e.g., Ling, et al., *Proc. Natl. Acad. Sci. USA* (2008)), nucleic acids (see, e.g., Chan, et al., *Magn. Reson. Med.* (2012); Jin, et al., *Magn. Reson. Med.* (2011); Torrealdea, et al., *Contrast Media Mol. Imaging* (2013)), and peptides (see e.g., McMahon, et al., *Magn. Reson. Med.* (2008); Airan, et al., *Magn. Reson. Med.* (2012); Salhotra, et al., *NMR Biomed* (2008)).

The CEST contrast mechanism involves selective irradiation of labile protons on the diamagnetic CEST (diaCEST) agent to perturb their signal, with this signal change then transferred to water via a dynamic exchange process between these labile protons and bulk water (see, e.g., van Zijl, *Proc. Natl. Acad. Sci.* (2007)). Because a number of common metabolites possess labile protons, there can be challenges in discriminating the signal loss associated with the metabolite of interest and background (see, e.g., Liu, et al., *NMR Biomed* (2013)), with most of the exchangeable protons on metabolites resonating between 1 ppm to 3.6 ppm from water. Recently, iopamidol, a computed tomography (CT) agent approved for clinical use, was reported to produce strong CEST contrast at shifts that are further from water, from 4.2 ppm to 5.5 ppm (Longo, et al., *Magn Reson Med.* (2011)).

The presently disclosed subject matter features compositions and methods for CEST MRI that are useful for imaging PSMA, an attractive biomarker for imaging and therapy of prostate cancer and many other types of cancer and tumor neovasculature.

The presently disclosed subject matter is based, at least in part, on the unexpected discovery that salicylic acid (SA), one of the main metabolites of aspirin, possesses a suitable exchangeable proton that resonates 9.3 ppm from water, a frequency far removed from all other organic diaCEST agents reported to date. It also has been discovered that salicylic acid analogs produce significantly enhanced contrast in MR images detectable through chemical exchange saturation transfer (CEST), and retain their CEST contrast sensitivity when grafted on a polymeric platform. The SA modified polymeric platform (SA PolyCEST), can further be modified with Glu-Lysine urea, an inhibitor of Prostate-specific membrane antigen (PSMA), a cell surface protein that is over expressed in most prostate cancers, including hormone-refractory, metastatic disease and tumor neovasculature. The PSMA targeted SA PolyCEST retains its high CEST contrast sensitivity as well as its high binding affinity for PSMA.

The presently disclosed subject matter provides MRI contrast agents that may be used for various clinical or non-clinical purposes. Compared with paramagnetic CEST (paraCEST) contrast agents, organic CEST contrast agents of the presently disclosed subject matter have many advantages, such as, for example, lower toxicity due to the absence of lanthanide metals, ease of modification, and clearance through breakdown during natural biochemical processes. These characteristics are in sharp contrast to convention organic CEST agents, which suffer from sensitivity drawbacks, especially due to a small chemical shift difference between exchangeable proton and water.

A. Compounds of Formula (I), Formula (II), Formula (III) and Formula (IV)

Accordingly, in some embodiments, the presently disclosed subject matter provides a compound of formula (I), formula (II), formula (III), or formula (IV):

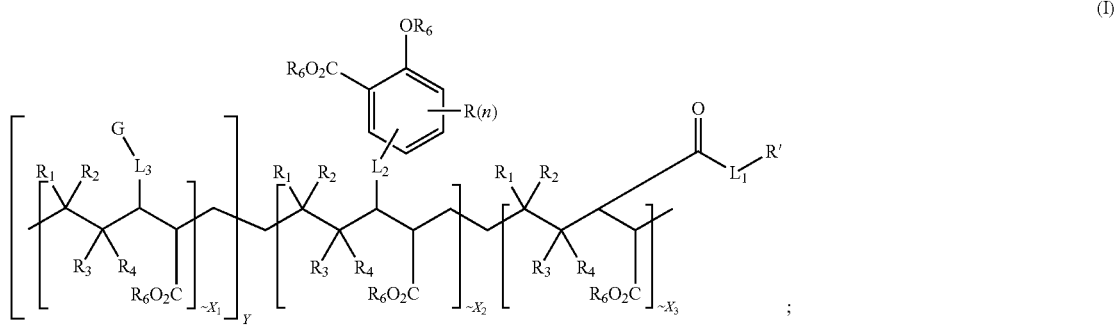

(I)

(II)

-continued

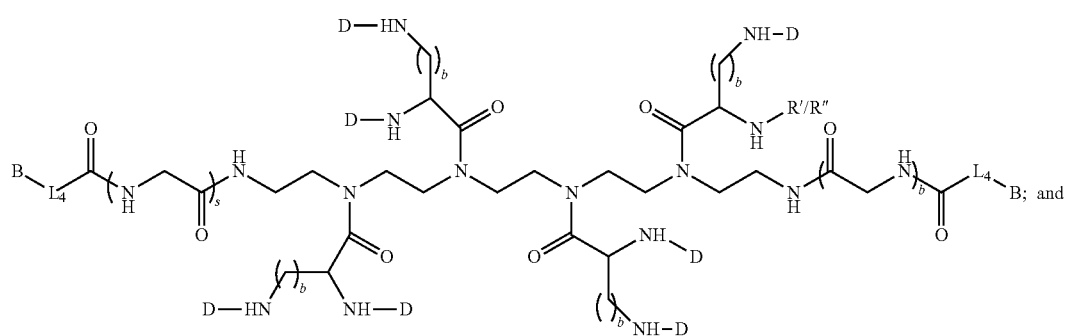

(III)

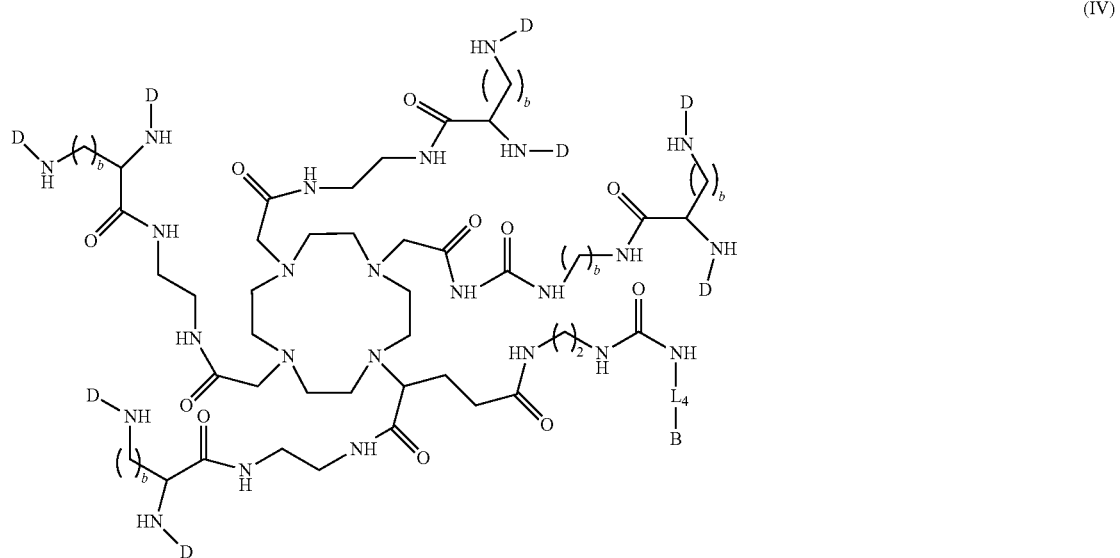

(IV)

wherein:

R' is

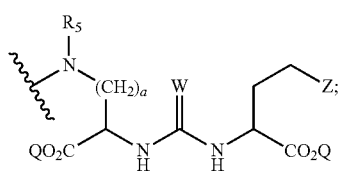

B is R' or

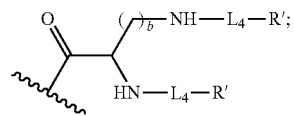

Z is tetrazole or $CO_2Q$; Q is H or a protecting group; W is O or S; a is an integer selected from the group consisting of 0, 1, 2, 3 and 4; b is an integer selected from the group consisting of 1, and 4; n is independently an integer selected from the group consisting of 0, 1, 2, and 3; s is an integer selected from the group consisting of 0, 1, 2, 3 and 4; each R is independently selected from the group consisting of hydrogen, substituted or unsubstituted alkyl, alkoxyl, hydroxyl, hydroxyalkyl, carboxyl, acyl, carbonyl, carbamoyl, alkylcarbamoyl, halogen, amino, alkylamino, nitro, nitrile, amide, haloalkyl, aryl, cycloalkyl, aralkyloxyl, and —$SO_3H$; $R_1$, $R_2$, $R_3$ and $R_4$ are independently selected from the group consisting of H or substituted or unsubstituted linear or branched alkyl, substituted or unsubstituted aryl, and alkoxyl; $R_5$ is independently H, $C_1$-$C_4$ alkyl or $C_2$-$C_{12}$ aryl; each $R_6$ is independently H, Na or a protecting group; $L_1$ is a linking group selected from the group consisting of —$(CH_2)_m$—, —$(CH_2$—$CH_2$—$O)_t$—, —$(O$—$CH_2$—$CH_2)_t$—, —$NR_7$—$(CHR_8)_m$—$NR_7$—$C(=O)$—$(CH_2)_m$—$C(=O)$— and —$NR_7$—$(CHR_8)_m$—$C(=O)$—$NR_7$—$(CH_2)_m$—$C(=O)$—; $L_2$ is a linking group selected from the group consisting of —$(CH_2)_m$—$NR_7$—$C(=O)$—$(CH_2)_p$—, —$(CH_2)_m$—$C(=O)$—$NR_7$—$(CH_2)_p$—, —$(CH_2)_m$—$NR_7$—$C(=O)$—$NR_7$—$(CH_2)_p$—, —$(CH_2)_m$—$NR_7$—$C(=O)$—$NR_7$—$(CH_2)_p$—, —$(CH_2)_m$—$O$—$C(=O)$—$NR_7$—, —$CH_2)_m$—$O$—$C(=O)$—$NR_7$—$(CH_2)_p$—, —$(CH_2)_m$—$NR_7$—$C(=O)$—$O$—$CH_2)_p$—, —$(CH_2)_m$—$NR_7$—$C(=O)$—$O$—$(CH_2)_p$—, —$SO_2$—$NH$—$(CH_2)_p$—, and —$(CH_2)_m$—$SO_2$—$NH$—$(CH_2)_p$—; $L_3$ is a linking group selected from the group consisting of —$C(=O)$—$NR_7$—$(CH_2)_m$—, —$C(=O)$—$NR_7$—$(CH_2)_m$—$NR_7$—, —$C(=O)$—$NR_7$—$(CH_2)_m$—$C(=O)$—$NR_7$—, —$C(=O)$—$NR_7$—$(CH_2)_m$—$NR_7$—$C(=O)$—, —$C(=O)$—$NR_7$—$(CH_2)_m$—$NR_7$—$C(=O)$—$NR_7$—, —$C(=O)$—$NR_7$—$(CH_2)_m$—$NR_7$—$C(=O)$—$(CH_2)_p$—, —$C(=O)$—$NR_7$—$(CH_2)_m$—$C(=O)$—$NR_7$—$(CH_2)_p$—, —$C(=O)$—$NR_7$—$(CH_2)_m$—$(O$—$CH_2$—$CH_2)_t$—, —$C(=O)$—$NR_7$—$(CH_2)_m$—$(CH_2$—$CH_2$—$O)_t$—

—(CH$_2$)$_p$—, and —C(=O)—NR$_7$—(CH$_2$)$_m$—(O—CH$_2$—CH$_2$)$_t$—C(=O)—NR$_7$—; L$_4$ is a linking group selected from the group consisting of —(CH$_2$)$_m$—, —C(=O)—(CH$_2$)$_m$—C(=O)—, —C(=O)—(CH$_2$)$_m$—NR$_7$—C(=O)—, —C(=O)—(CH$_2$—CH$_2$—O)$_t$—C(=O)—, —C(=O)—(CHR$_8$)$_m$—C(=O)—, —C(=O)—(CHR$_8$)$_m$—NR$_7$—C(=O)—, —C(=O)—(CH$_2$—CH$_2$—O)t-C(=O)—, and —C(=O)—(O—CH$_2$—CH$_2$)$_t$—C(=O)—; each R$_7$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; each R$_8$ is independently selected from the group consisting of hydrogen, and —COOR$_6$; m and p are each independently an integer selected from the group consisting of 0, 1, 2, 3, 4, 5, 6, 7 and 8; t is an integer selected from the group consisting of 1, 2, 3, 4, 5, 6, 7, 8, 9, 10, 11 and 12; Y is an integer selected from the group consisting of 0 and 1; G is an azide, an alkyne, a fluorescent dye moiety that emits light in the visible or near-infrared (NIR) spectrum, or a chelating moiety optionally comprising a metal or a radiometal; X$_1$ is an integer selected from the group consisting of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and 2; X$_2$ and X$_3$ are each independently an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40; A is selected from the group consisting of:

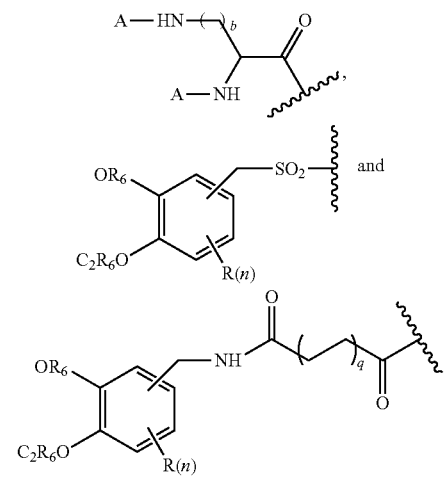

wherein q is an integer selected from the group consisting of 1, 2, 3, 4, and 5; D is selected from the group consisting of:

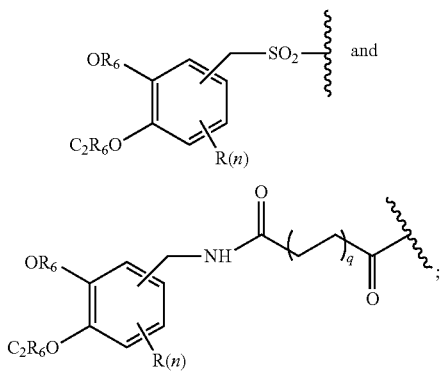

or a salt or a stereoisomer thereof.

In particular embodiments R' is

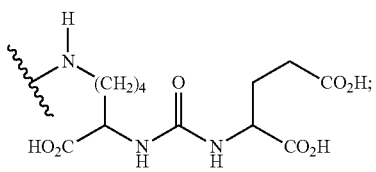

and

B is R' or

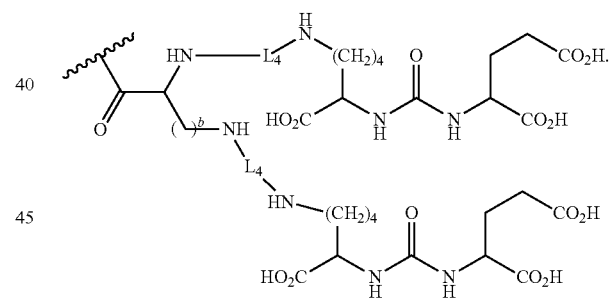

In other particular embodiments, the compound formula (II) is selected from the group consisting of:

(IIa)
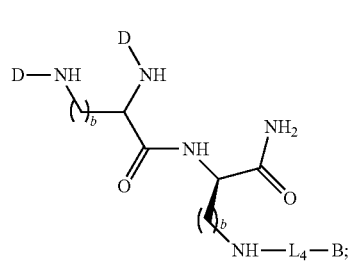

(IIb)
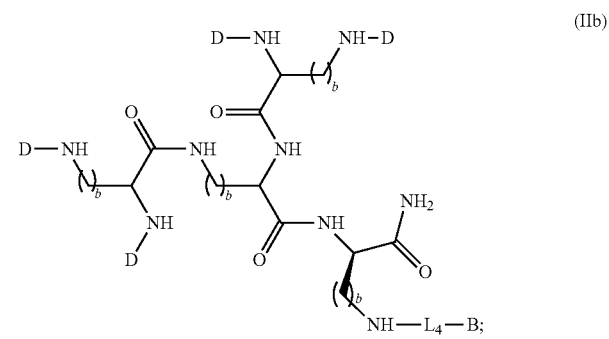

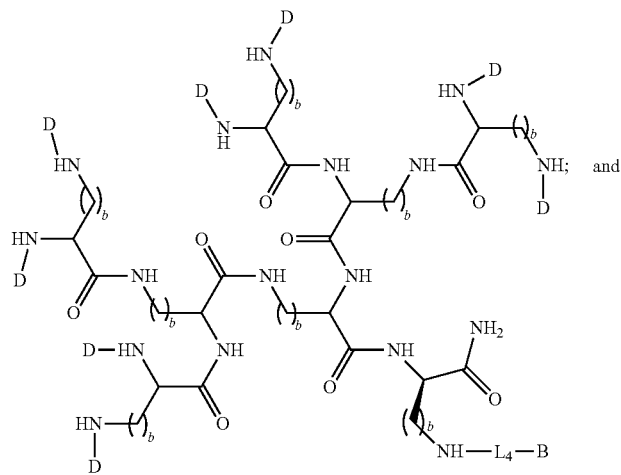

(IIc)

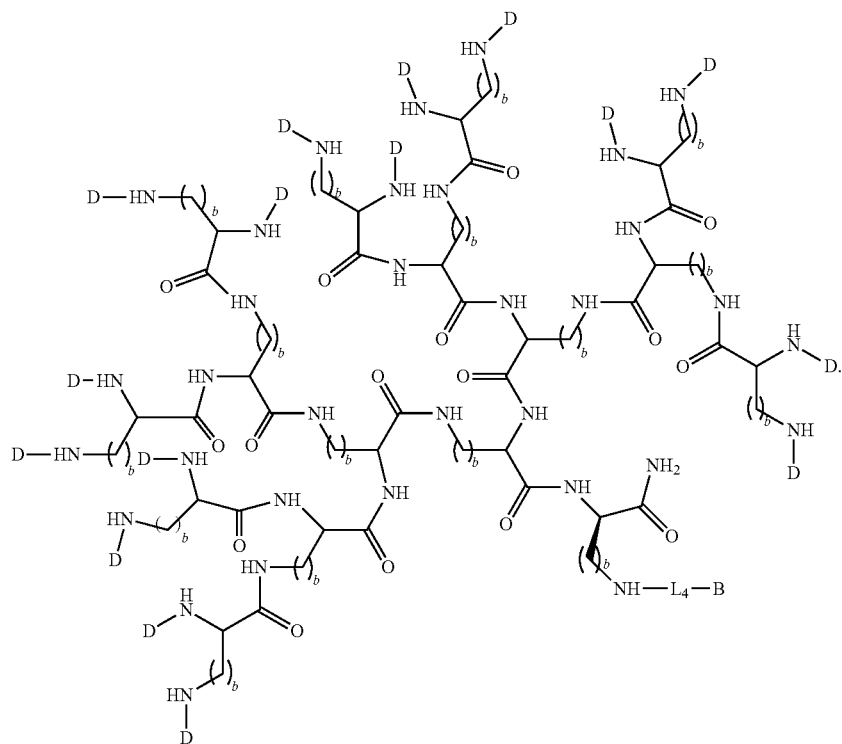

(IId)

In more particular embodiments, the ratio of CEST contrast moiety and targeting urea moiety (X₂:X₃) is about 10:1. In other particular embodiments, the ratio of NIR moiety, CEST contrast moiety and targeting urea moiety (X₁:X₂:X₃) is about 0.1:10:1. In yet more particular embodiments, the ratio of chelating moiety, CEST contrast moiety and targeting urea moiety (X₁:X₂:X₃) is about 1:10:1.

In further embodiments, the chelating moiety optionally comprising a metal or a radiometal, is selected from the group consisting of:

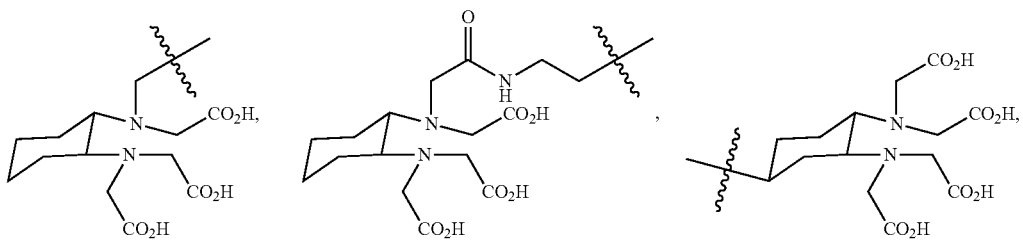

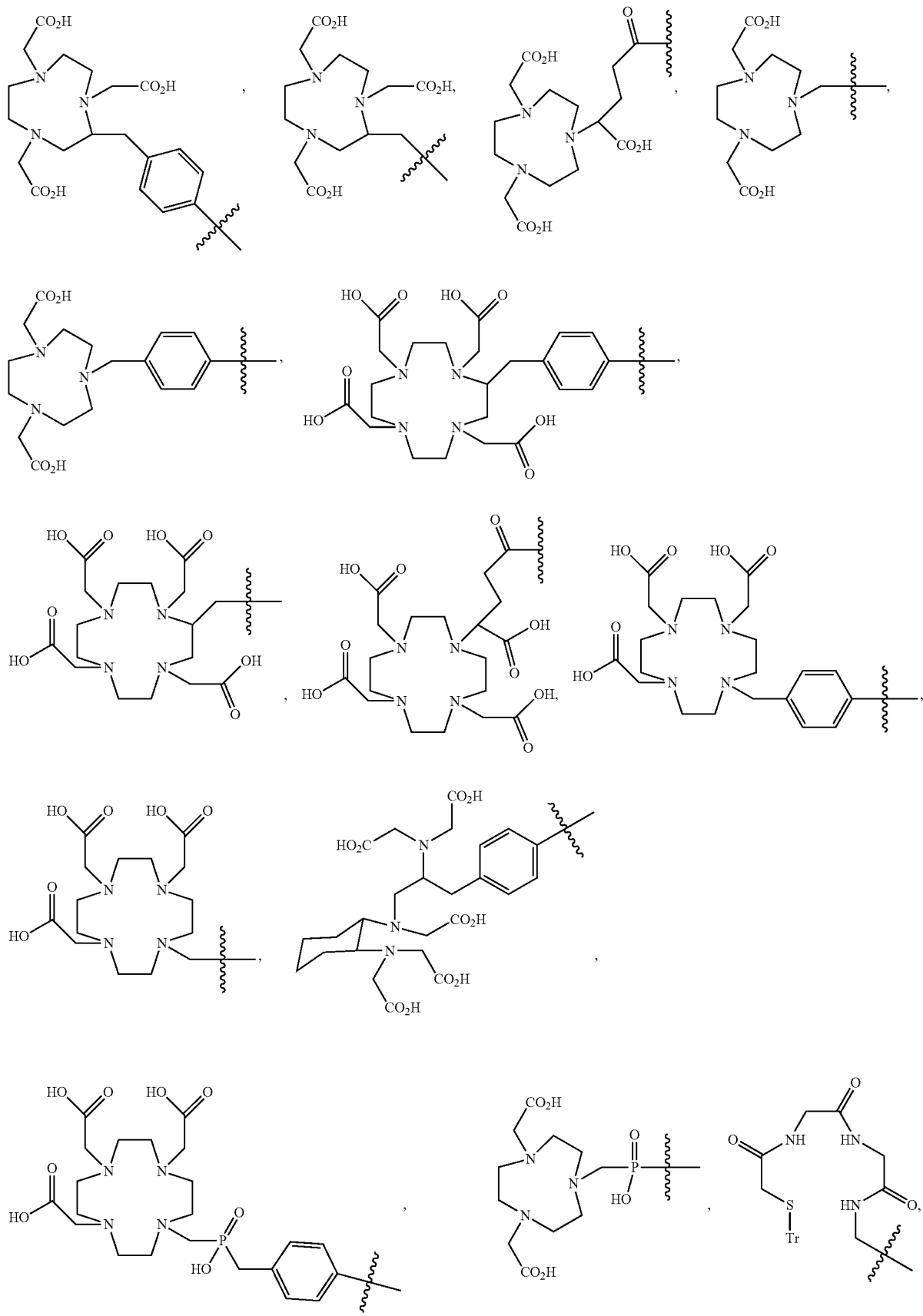

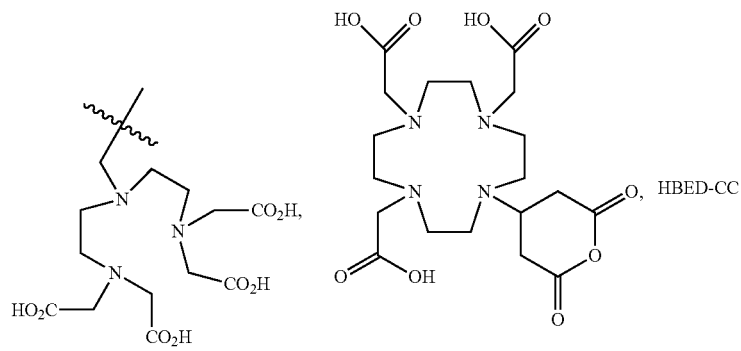

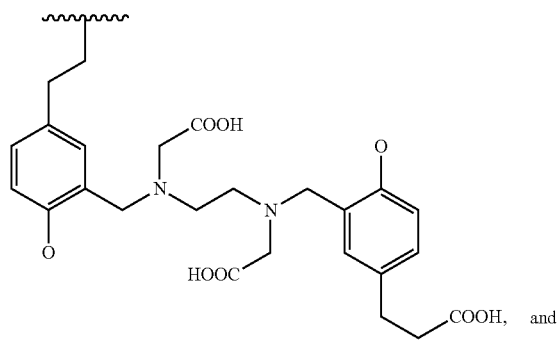

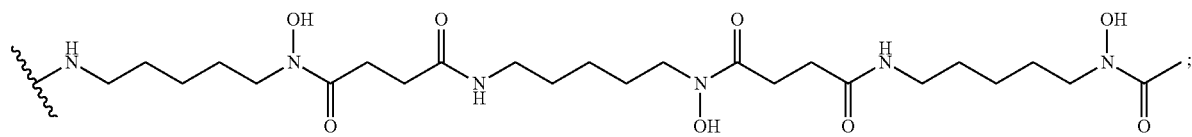

or a pharmaceutically acceptable salt thereof.

In certain embodiments the metal is selected from the group consisting of: Y, Lu, Tc, Zr, In, Sm, Re, Cu, Pb, Ac, Bi, Al, Ga, Re, Ho and Sc.

In other embodiments, the radiometal is selected from the group consisting of: $^{68}$Ga, $^{64}$Cu, Al—$^{18}$F, $^{86}$Y, $^{90}$Y, $^{89}$Zr, $^{111}$In, $^{99m}$Tc, $^{177}$Lu, $^{153}$Sm, $^{186}$Re, $^{188}$Re, $^{67}$Cu, $^{212}$Pb, $^{225}$Ac, $^{213}$Bi, $^{212}$Bi, $^{212}$Pb, $^{67}$Ga, $^{203}$Pb, $^{47}$Sc, and $^{166}$Ho.

In other embodiments, the NIR dye is selected from the group consisting of: carbocyanine, indocarbocyanine, oxacarbocyanine, thiacarbocyanine and merocyanine, polymethine, coumarine, rhodamine, xanthene, fluorescein, borondipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

In more specific embodiments, the fluorescent dye moiety is selected from the group consisting of:

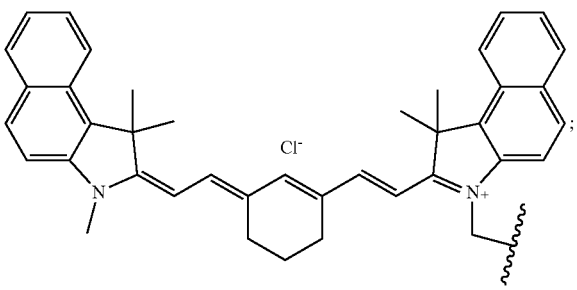
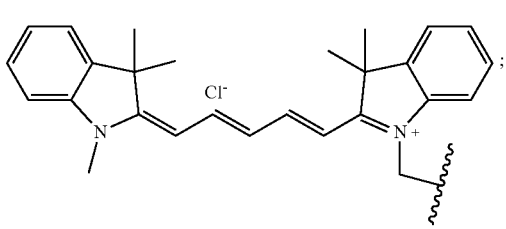

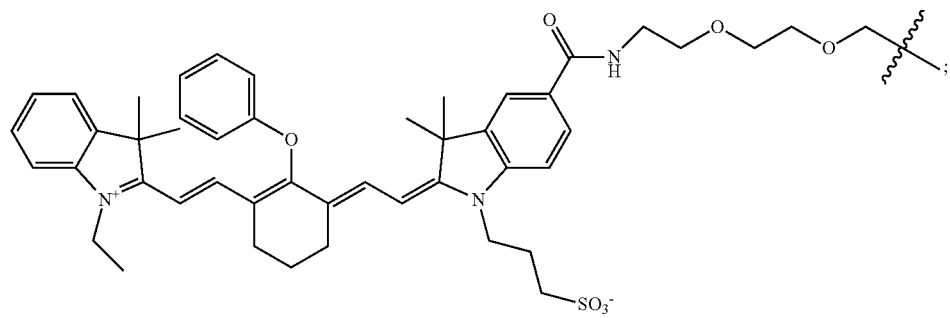
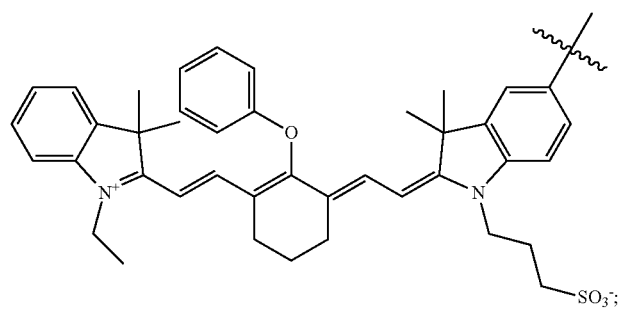
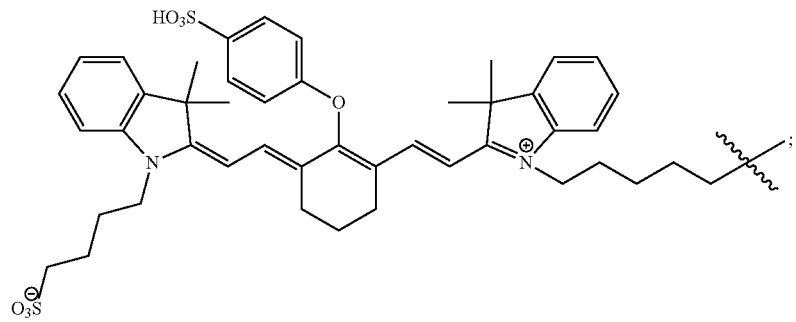
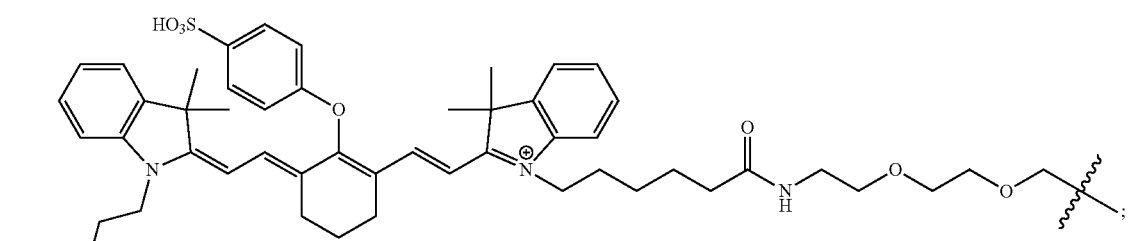
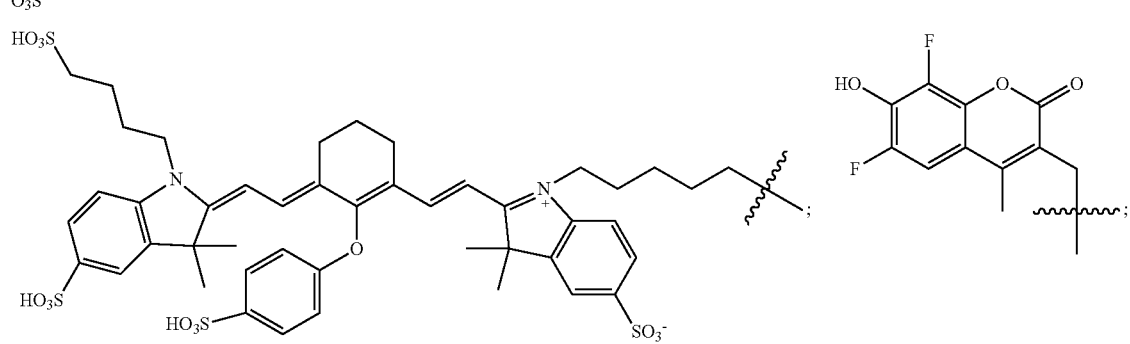

-continued
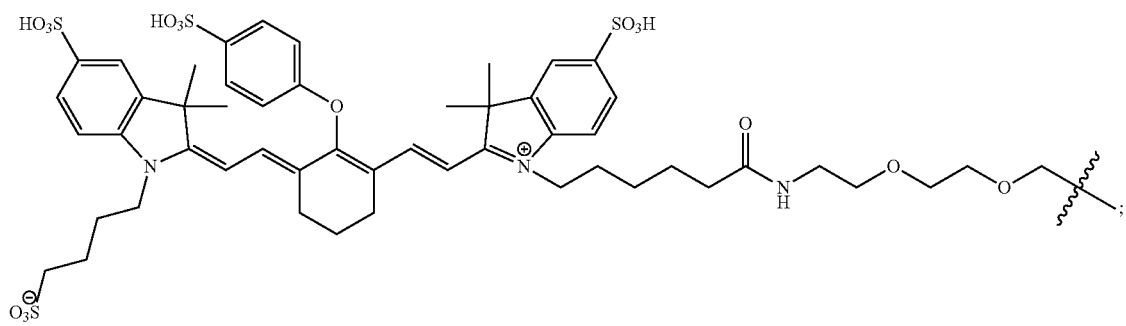
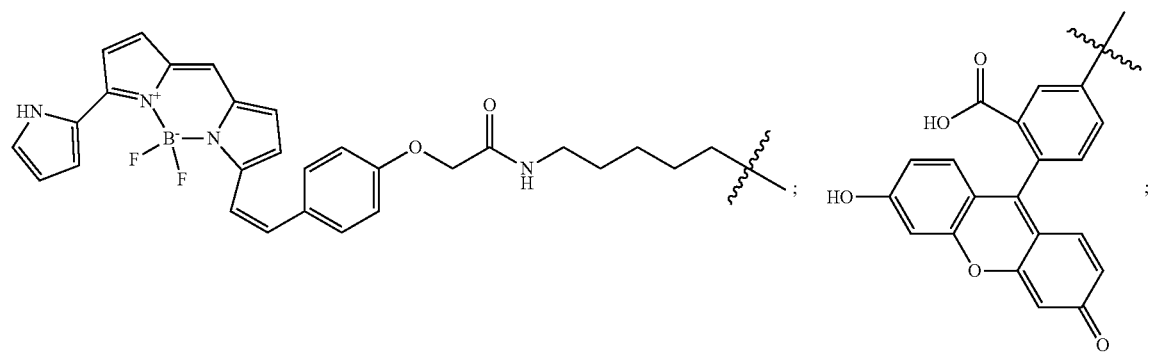
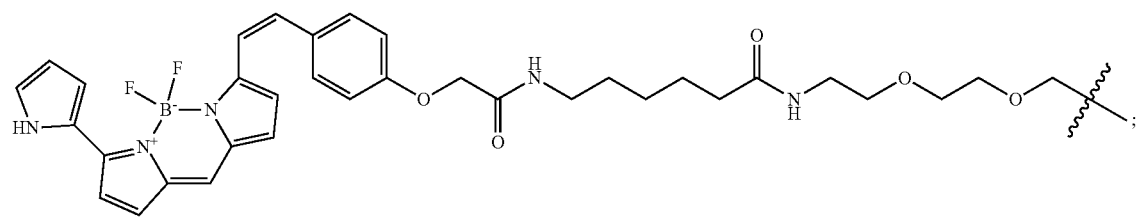
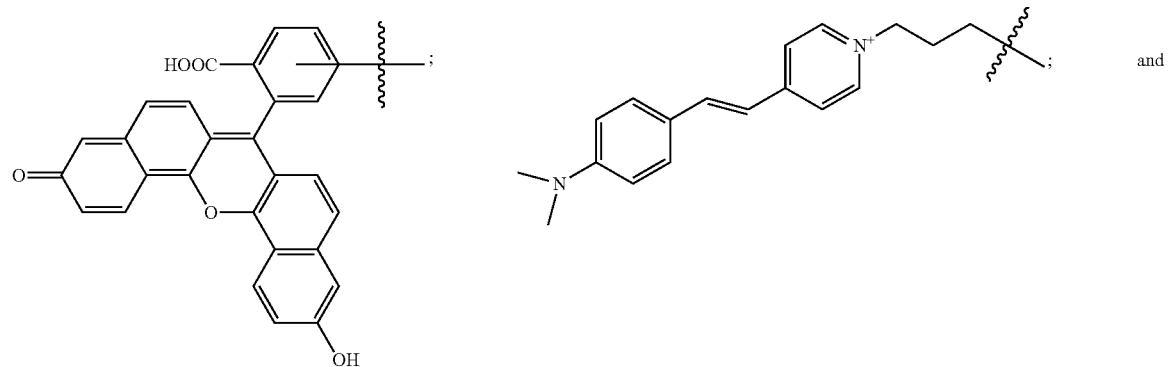
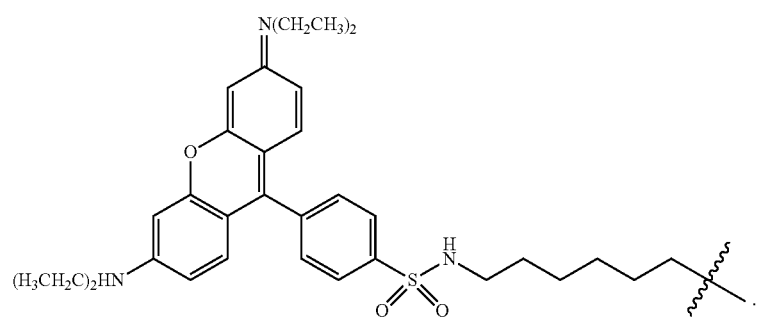

In representative embodiments, the compound of formula (I) is selected from the group consisting of:
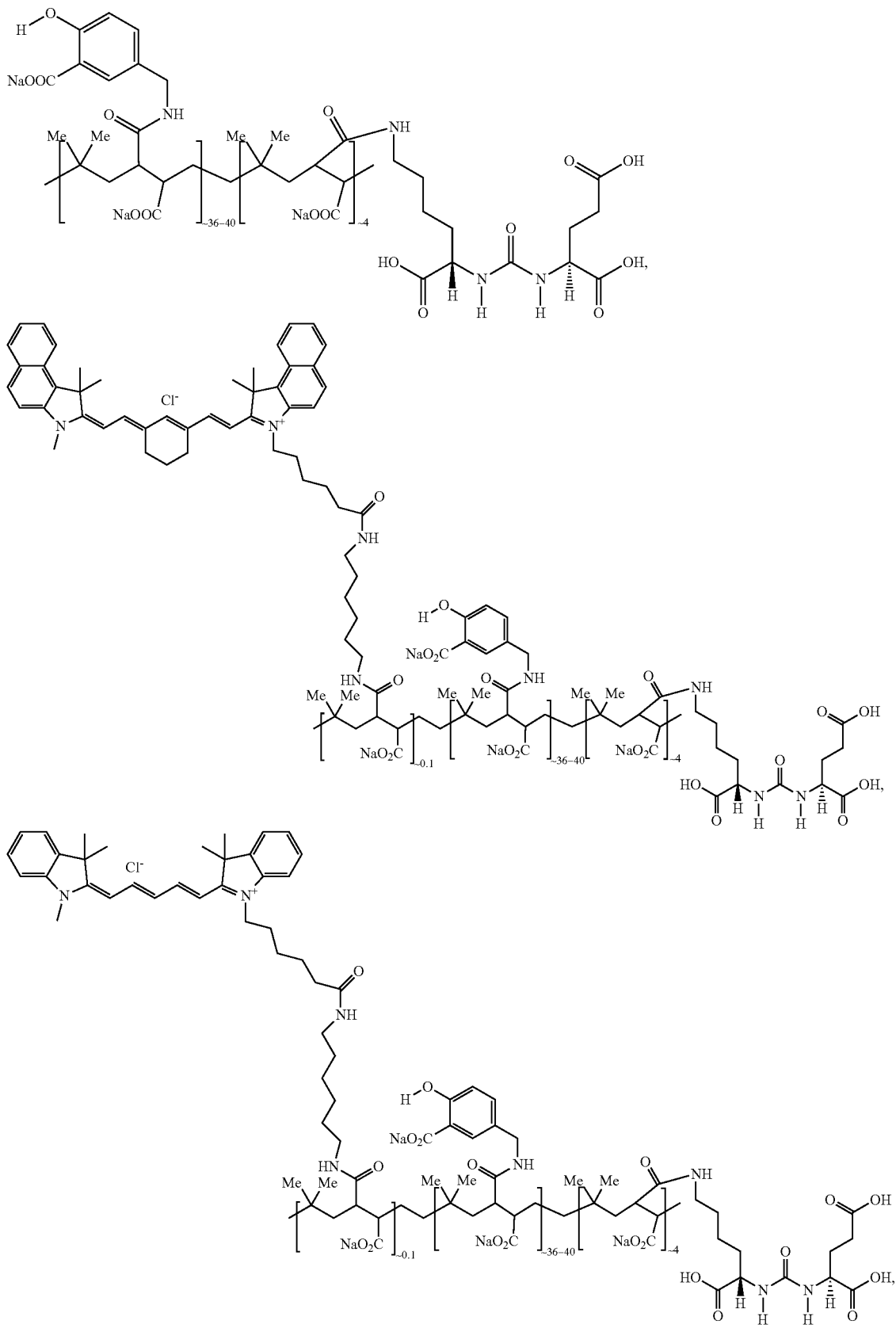

-continued
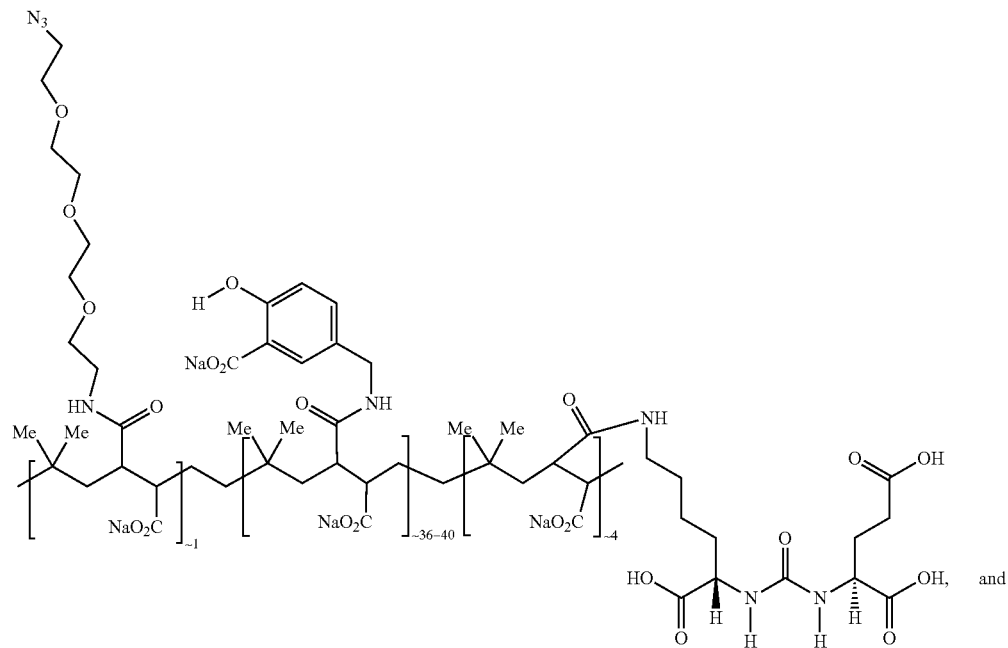
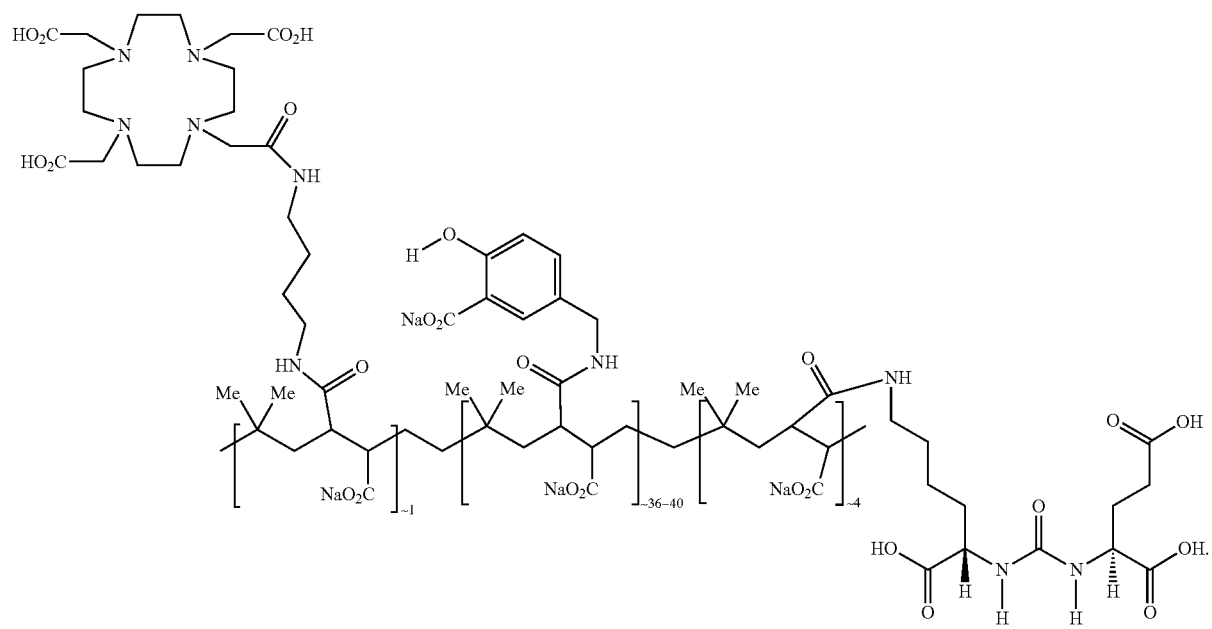
In other representative embodiments, the compound of formula (I) is selected from the group consisting of:

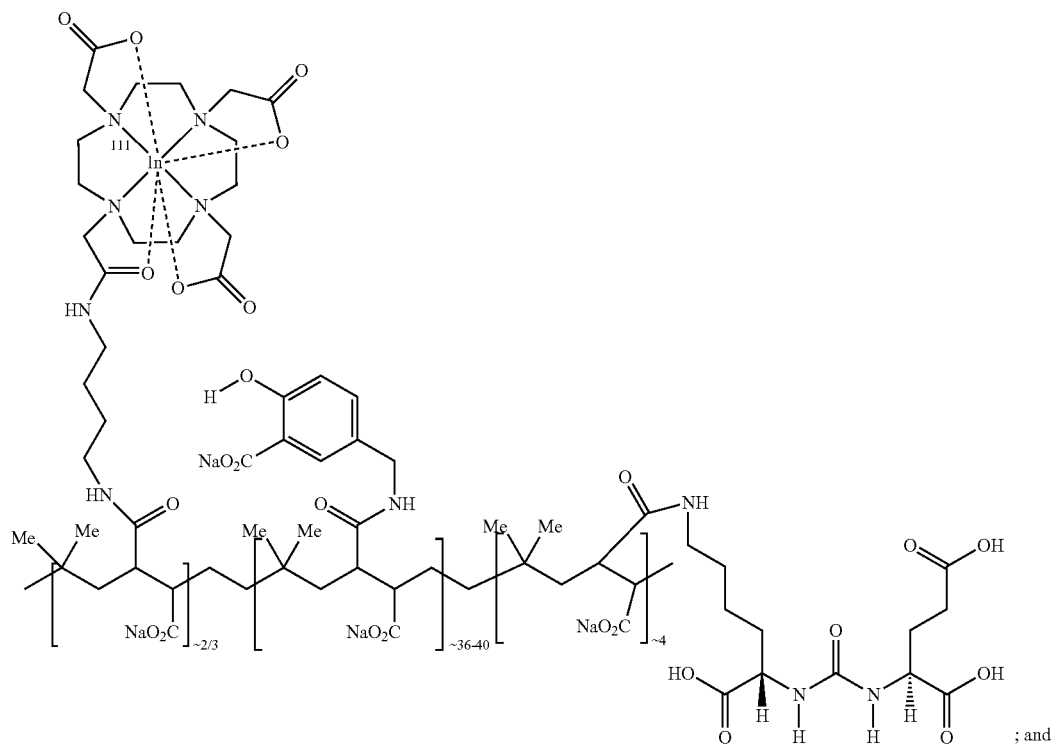

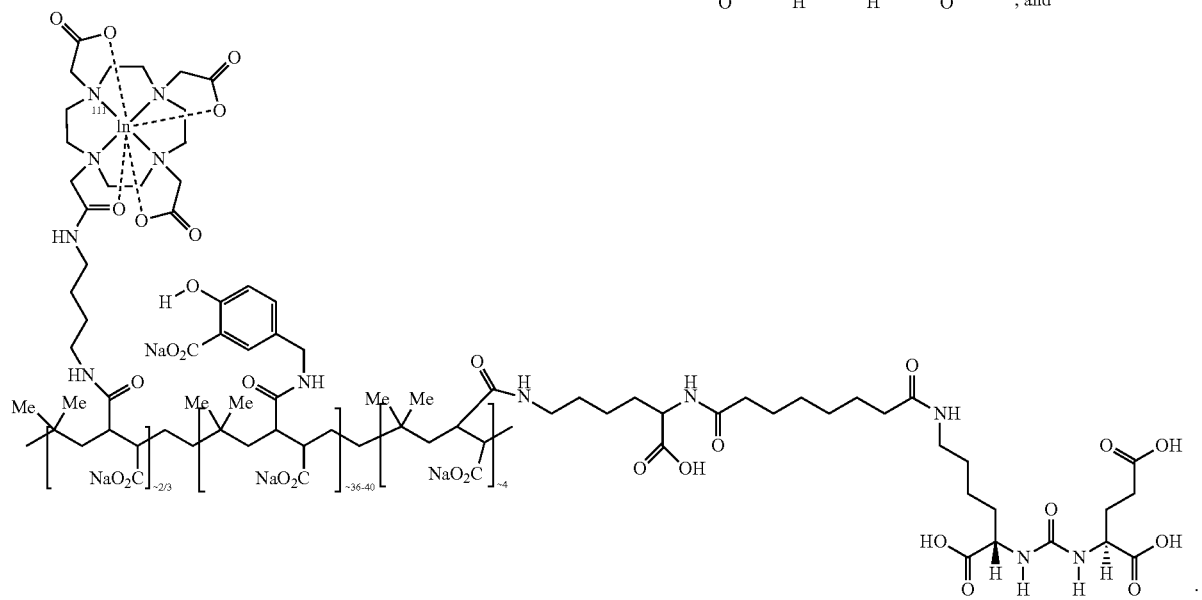

B. Pharmaceutical Compositions and Administration

In another aspect, the present disclosure provides a pharmaceutical comprising a compound of formula (I), formula (II), formula (III), and/or formula (IV) in admixture with a pharmaceutically acceptable carrier, diluent or excipient. One of skill in the art will recognize that the pharmaceutical compositions include the pharmaceutically acceptable salts or hydrates of the compounds described above.

Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

C. Methods of Using the Compounds of Formula (I), Formula (II), Formula (III) and/or Formula (IV), or Pharmaceutical Compositions of any Thereof In some embodiments, the presently disclosed subject matter features a method for producing a magnetic resonance imaging (MRI) of one or more PSMA-expressing tumors or cells, the method comprising contacting the one or more PSMA-expressing tumors or cells with an effective amount of a magnetic resonance imaging contrast agent; and imaging the target using a based MRI technique to produce the MR image of the one or more PSMA-expressing tumors or cells, wherein the magnetic resonance imaging contrast agent is a compound of formula (I), formula (II), formula (III) and/or formula (IV) or a pharmaceutical composition of any thereof; the compound formula (I), formula (II), formula (III) or formula (IV) comprising:

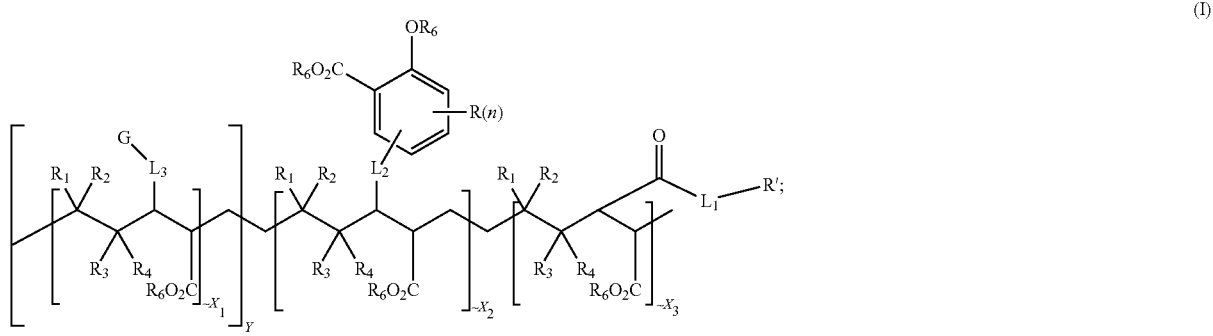

(I)

(II)

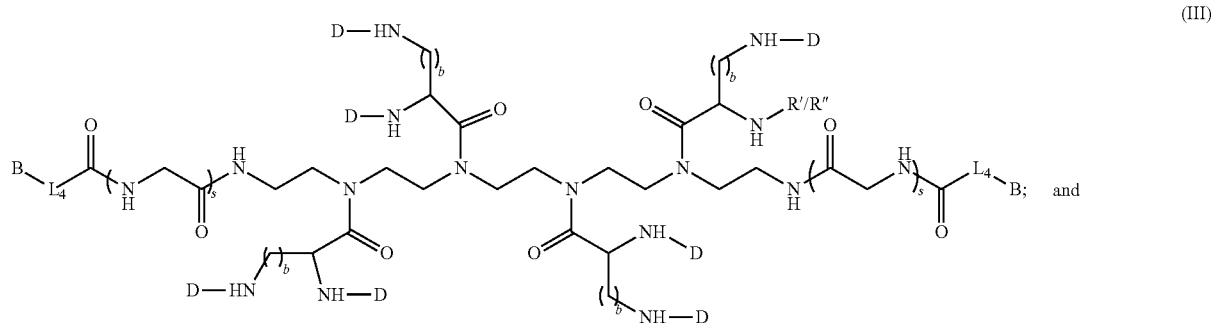

(III)

and

-continued (IV)

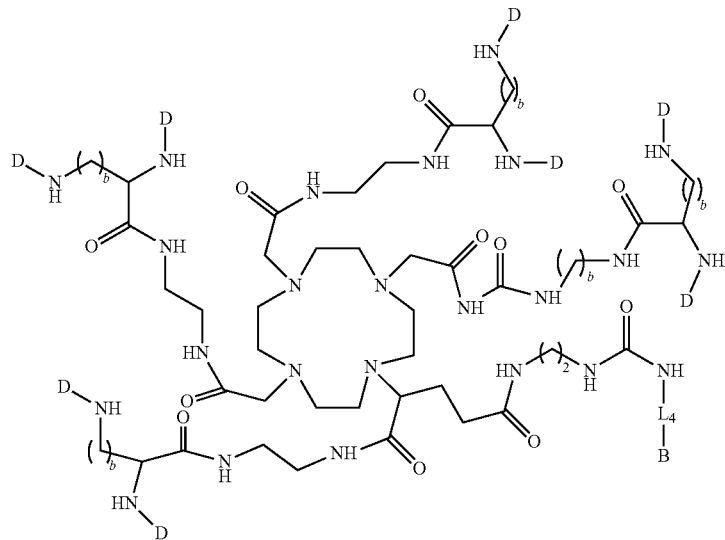

wherein:
R' is

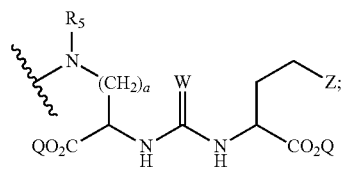

B is R' or

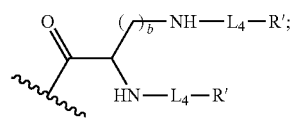

Z is tetrazole or $CO_2Q$; Q is H or a protecting group; W is O or S; a is an integer selected from the group consisting of 0, 1, 2, 3 and 4; b is an integer selected from the group consisting of 1, and 4; n is independently an integer selected from the group consisting of 0, 1, 2, and 3; s is an integer selected from the group consisting of 0, 1, 2, 3 and 4; each R is independently selected from the group consisting of hydrogen, substituted or unsubstituted alkyl, alkoxyl, hydroxyl, hydroxyalkyl, carboxyl, acyl, carbonyl, carbamoyl, alkylcarbamoyl, halogen, amino, alkylamino, nitro, nitrile, amide, haloalkyl, aryl, cycloalkyl, aralkyloxyl, and —$SO_3H$; $R_1$, $R_2$, $R_3$ and $R_4$ are independently selected from the group consisting of H or substituted or unsubstituted linear or branched alkyl, substituted or unsubstituted aryl, and alkoxyl; $R_5$ is independently H, $C_1$-$C_4$ alkyl or $C_2$-$C_{12}$ aryl; each $R_6$ is independently H, Na or a protecting group; $L_1$ is a linking group selected from the group consisting of —$(CH_2)_m$—, —$(CH_2$—$CH_2$—$O)_t$—, —$(O$—$CH_2$—$CH_2)_t$—, —$NR_7$—$(CHR_8)_m$—$NR_7$—$C(=O)$—$(CH_2)_m$—$C(=O)$— and —$NR_7$—$(CHR_8)_m$—$C(=O)$—$NR_7$—$(CH_2)_m$—$C(=O)$—; $L_2$ is a linking group selected from the group consisting of —$(CH_2)_m$—$NR_7$—$C(=O)$—$(CH_2)_p$—, —$(CH_2)_m$—$C(=O)$—$NR_7$—$(CH_2)_p$—, —$(CH_2)_m$—$NR_7$—$C(=O)$—$NR_7$—$(CH_2)_p$—, —$(CH_2)_m$—$NR_7$—$C(=O)$—$NR_7$—$(CH_2)_p$—, —$(CH_2)_m$—$O$—$C(=O)$—$NR_7$—, —$CH_2)_m$—$O$—$C(=O)$—$NR_7$—$(CH_2)_p$—, —$(CH_2)_m$—$NR_7$—$C(=O)$—$O$—$CH_2)_p$—, —$(CH_2)_m$—$NR_7$—$C(=O)$—$O$—$(CH_2)_p$—, —$SO_2$—$NH$—$(CH_2)_p$—, and —$(CH_2)_m$—$SO_2$—$NH$—$(CH_2)_p$—; $L_3$ is a linking group selected from the group consisting of —$C(=O)$—$NR_7$—$(CH_2)_m$—, —$C(=O)$—$NR_7$—$(CH_2)_m$—$NR_7$—, —$C(=O)$—$NR_7$—$(CH_2)_m$—$C(=O)$—$NR_7$—, —$C(=O)$—$NR_7$—$(CH_2)_m$—$NR_7$—$C(=O)$—, —$C(=O)$—$NR_7$—$(CH_2)_m$—$NR_7$—$C(=O)$—$NR_7$—, —$C(=O)$—$NR_7$—$(CH_2)_m$—$NR_7$—$C(=O)$—$(CH_2)_p$—, —$C(=O)$—$NR_7$—$(CH_2)_m$—$C(=O)$—$NR_7$—$(CH_2)_p$—, —$C(=O)$—$NR_7$—$(CH_2)_m$—$(O$—$CH_2$—$CH_2)_t$—, —$C(=O)$—$NR_7$—$(CH_2)_m$—$(CH_2$—$CH_2$—$O)_t$—$(CH_2)_p$—, and —$C(=O)$—$NR_7$—$(CH_2)_m$—$(O$—$CH_2$—$CH_2)_t$—$C(=O)$—$NR_7$—; $L_4$ is a linking group selected from the group consisting of —$(CH_2)_m$—, —$C(=O)$—$(CH_2)_m$—$C(=O)$—, —$C(=O)$—$(CH_2)_m$—$NR_7$—$C(=O)$—, —$C(=O)$—$(CH_2$—$CH_2$—$O)_t$—$C(=O)$—, —$C(=O)$—$(CHR_8)_m$—$C(=O)$—, —$C(=O)$—$(CHR_8)_m$—$NR_7$—$C(=O)$—, —$C(=O)$—$(CH_2$—$CH_2$—$O)t$-$C(=O)$—, and —$C(=O)$—$(O$—$CH_2$—$CH_2)_t$—$C(=O)$—; each $R_7$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; each $R_8$ is independently selected from the group consisting of hydrogen, and —$COOR_6$; m and p are each independently an integer selected from the group consisting of 0, 1, 2, 3, 4, 5, 6, 7 and 8; t is an integer selected from the group consisting of 1, 2, 3, 4, 5, 6, 7, 8, 9, 10, 11 and 12; Y is an integer selected from the group consisting of 0 and 1; G is an azide, an alkyne, a fluoerescent dye moiety that emits light in the visible or near-infrared (NIR) spectrum, or a chelating moiety optionally comprising a metal or a radiometal; $X_1$ is an integer selected from the group consisting of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and 2; $X_2$ and $X_3$ are each independently an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40; A is selected from the group consisting of:

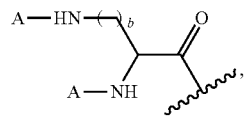

-continued

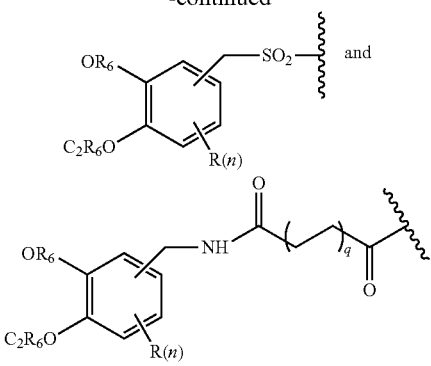

wherein q is an integer selected from the group consisting of 1, 2, 3, 4, and 5; D is selected from the group consisting of:

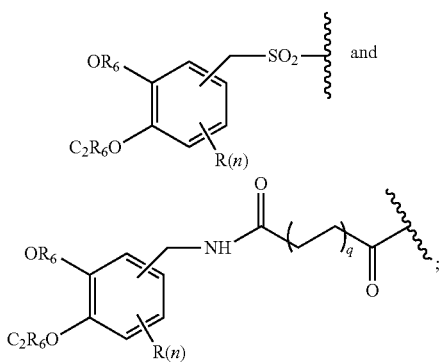

or a salt or a stereoisomer thereof.

"Contacting" means any action which results in at least one compound comprising the imaging agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s) or tumor(s).

Magnetic resonance imaging systems are known in the art and commercially available. In certain aspects, the magnetic resonance imaging system comprises an imaging apparatus configured to perform a CEST or FLEX MR technique using one or more compounds as described herein.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

A "tumor," as used herein, refers to all neoplastic cell growth and proliferation, whether malignant or benign, and all precancerous and cancerous cells and tissues.

In particular embodiments R' is

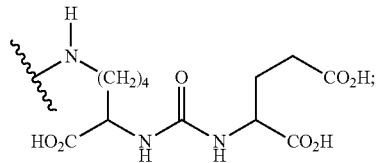

and
B is R' or

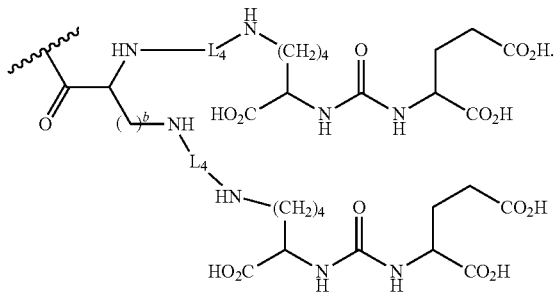

In other particular embodiments, the compound formula (II) is selected from the group consisting of:

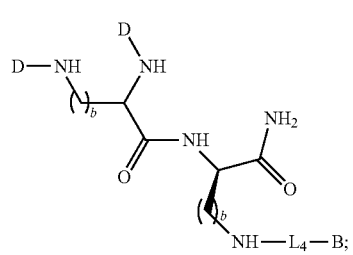

(IIa)

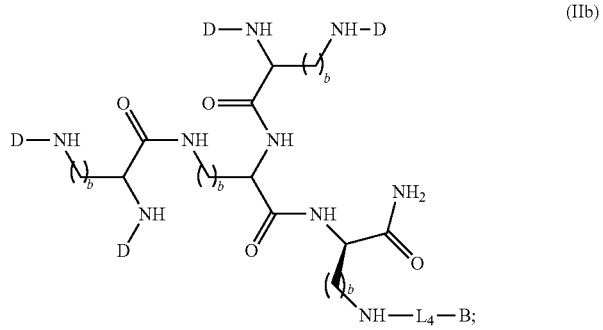

(IIb)

-continued

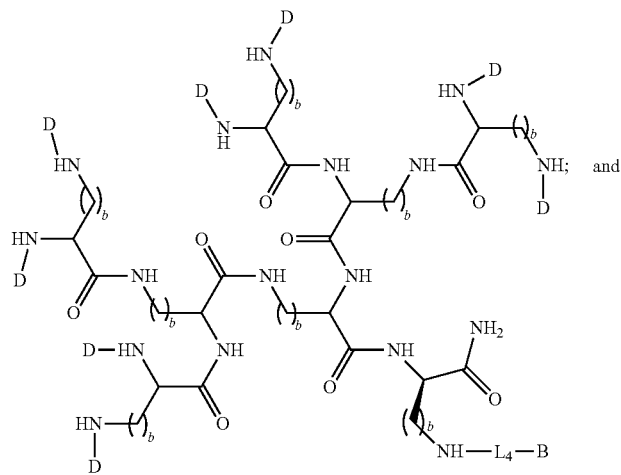

(IIc)

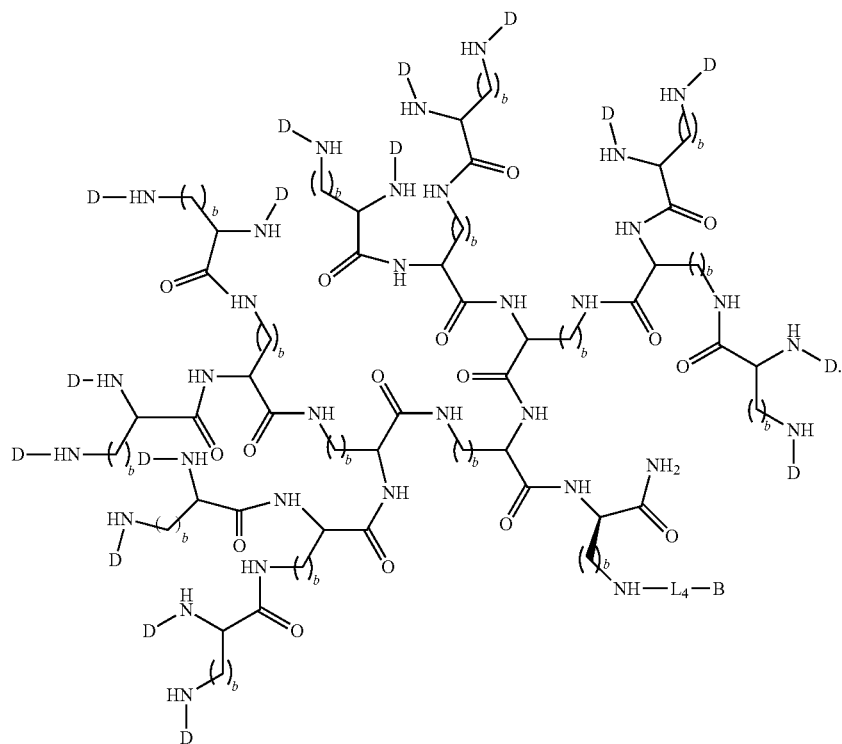

(IId)

In more particular embodiments, the ratio of CEST contrast moiety and targeting urea moiety ($X_2$:$X_3$) is about 10:1. In other particular embodiments, the ratio of NIR moiety, CEST contrast moiety and targeting urea moiety ($X_1$:$X_2$:$X_3$) is about 0.1:10:1. In yet more particular embodiments, the ratio of chelating moiety, CEST contrast moiety and targeting urea moiety ($X_1$:$X_2$:$X_3$) is about 1:10:1.

In further embodiments, the chelating moiety optionally comprising a metal or a radiometal, is selected from the group consisting of:

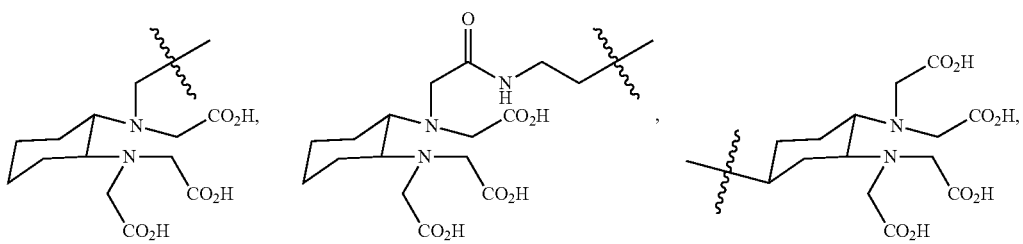

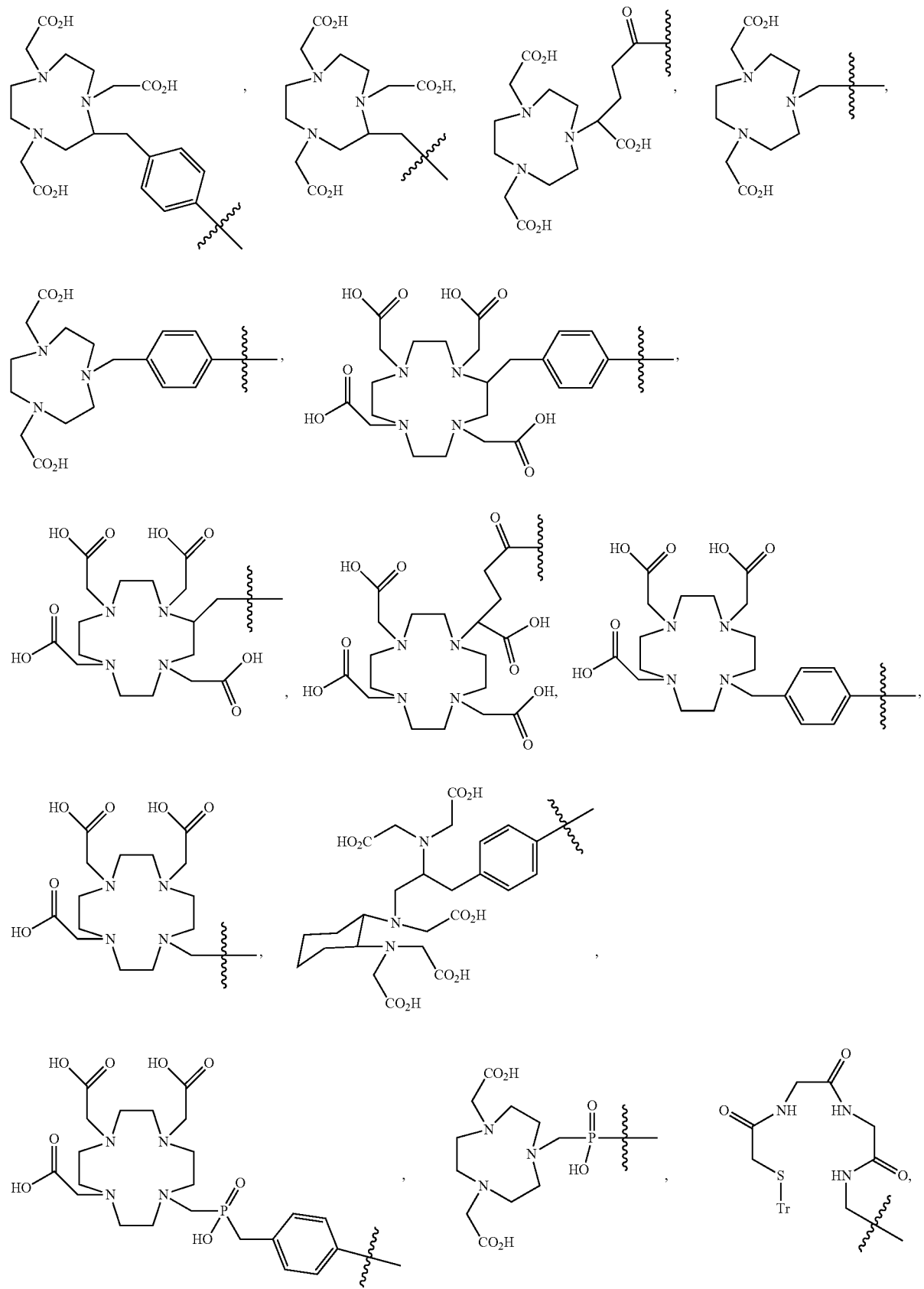

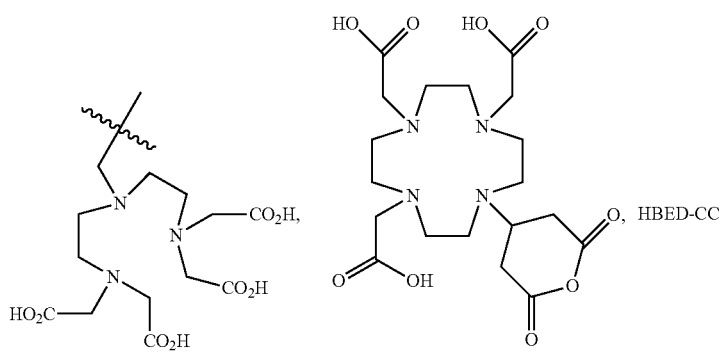

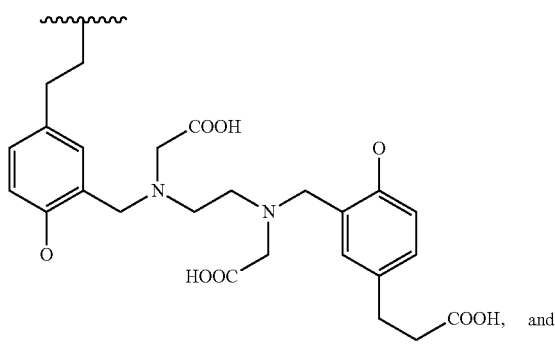

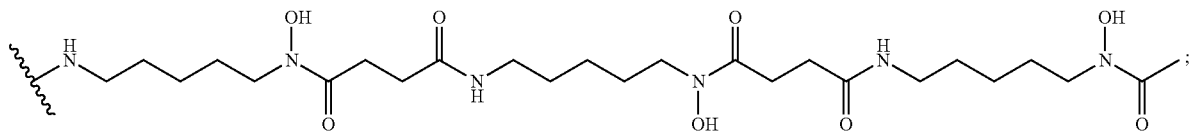

or a pharmaceutically acceptable salt thereof.

In certain embodiments the metal is selected from the group consisting of: Y, Lu, Tc, Zr, In, Sm, Re, Cu, Pb, Ac, Bi, Al, Ga, Re, Ho and Sc.

In other embodiments, the radiometal is selected from the group consisting of: $^{68}$Ga, $^{64}$Cu, Al—$^{18}$F, $^{86}$Y, $^{90}$Y, $^{89}$Zr, $^{111}$In, $^{99m}$Tc, $^{177}$Lu, $^{153}$Sm, $^{186}$Re, $^{188}$Re, $^{67}$Cu, $^{212}$Pb, $^{225}$Ac, $^{213}$Bi, $^{212}$Bi, $^{212}$Pb, $^{67}$Ga, $^{203}$Pb, $^{47}$Sc, and $^{166}$Ho.

In other embodiments, the NIR dye is selected from the group consisting of: carbocyanine, indocarbocyanine, oxacarbocyanine, thiacarbocyanine and merocyanine, polymethine, coumarine, rhodamine, xanthene, fluorescein, borondipyrromethane (BODIPY), Cy5, Cy5.5, Cy7, VivoTag-680, VivoTag-S680, VivoTag-S750, AlexaFluor660, Alexa Fluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

In more specific embodiments, the fluorescent dye moiety is selected from the group consisting of:

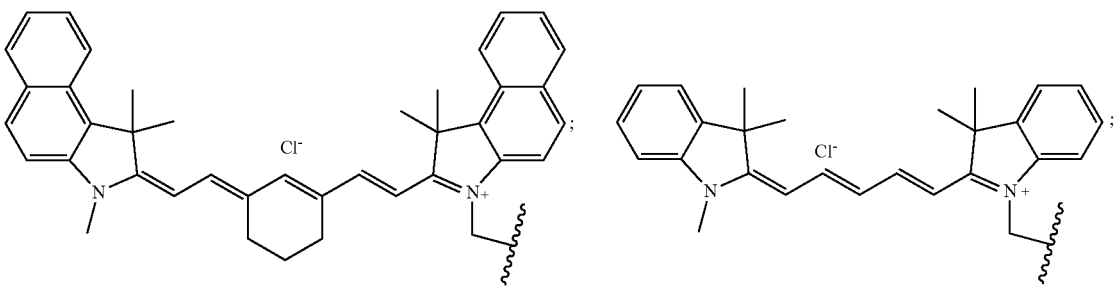

-continued
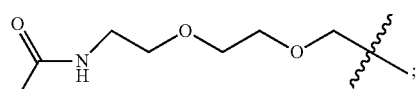
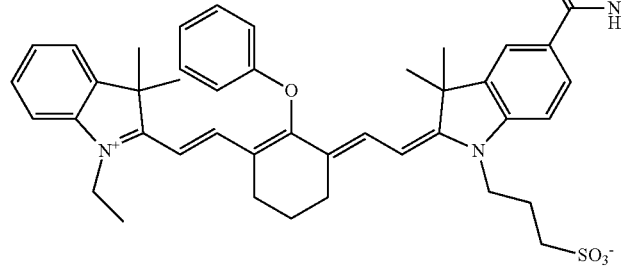
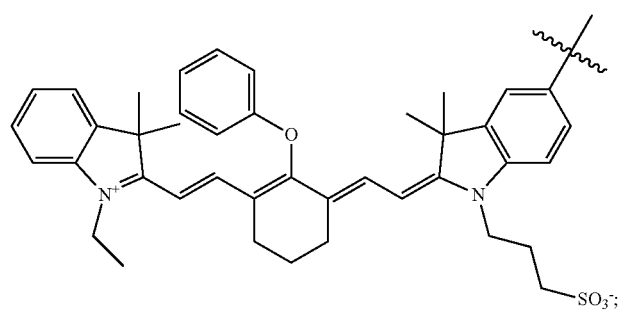
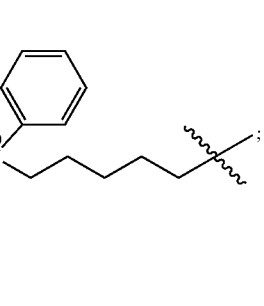
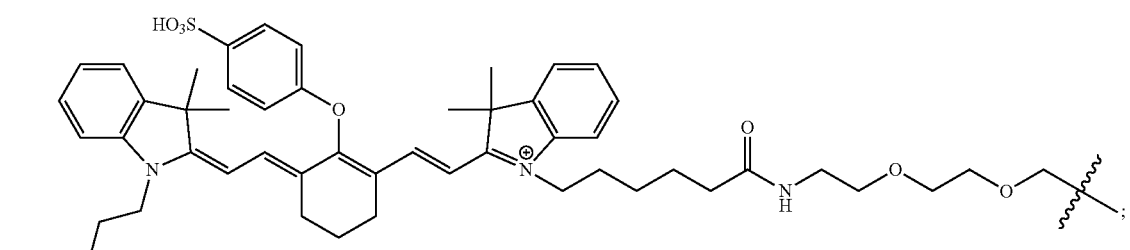
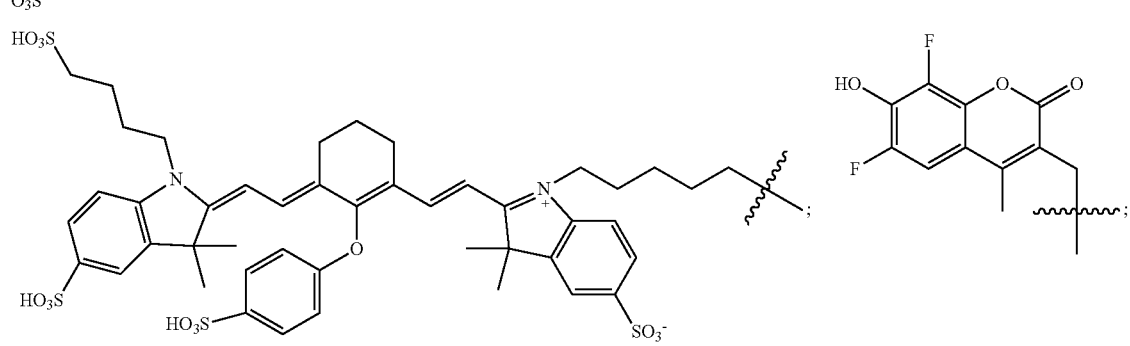

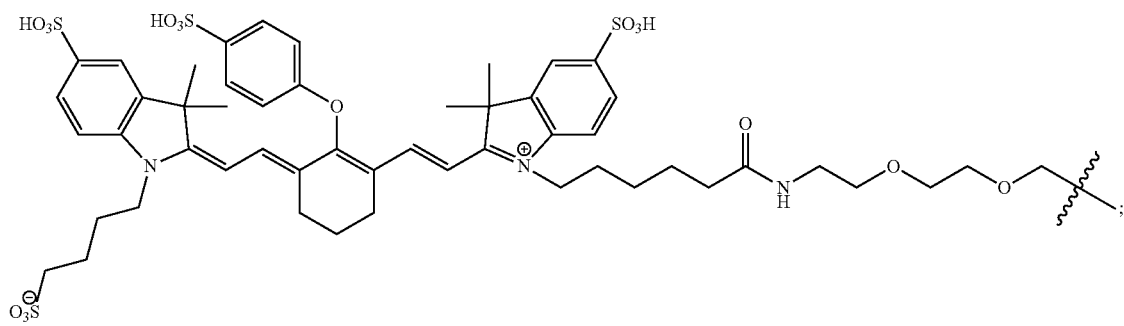
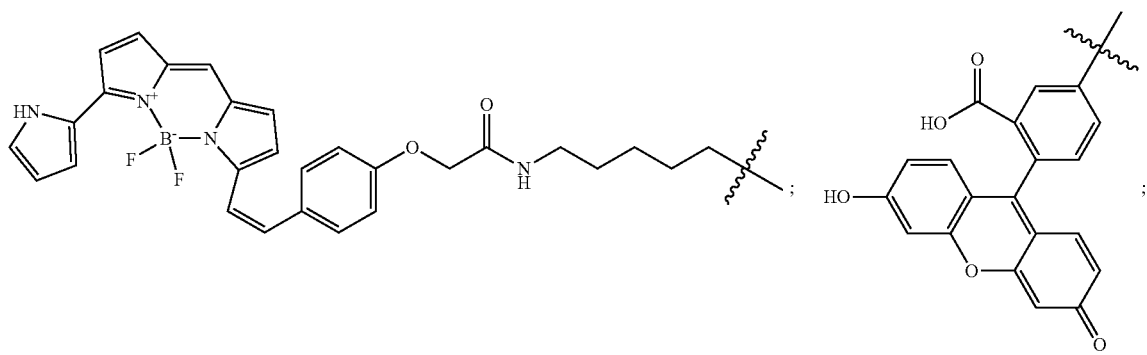
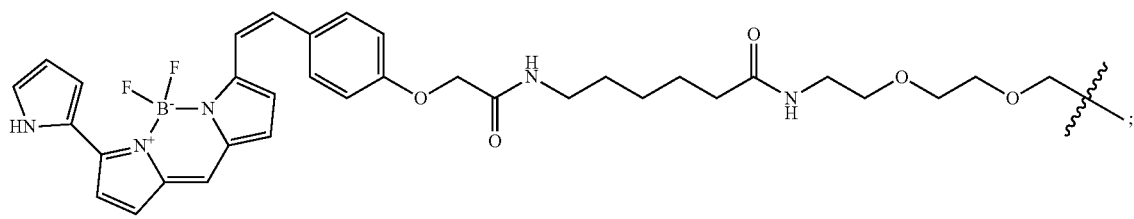
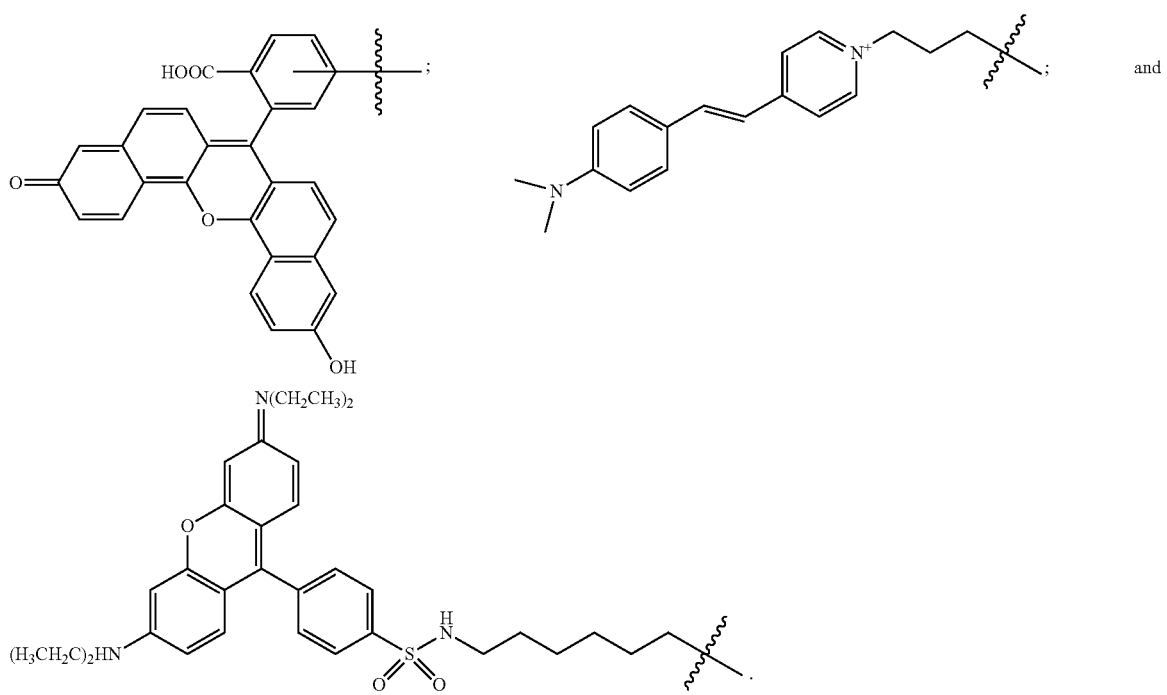

In representative embodiments, the compound of formula (I) is selected from the group consisting of:
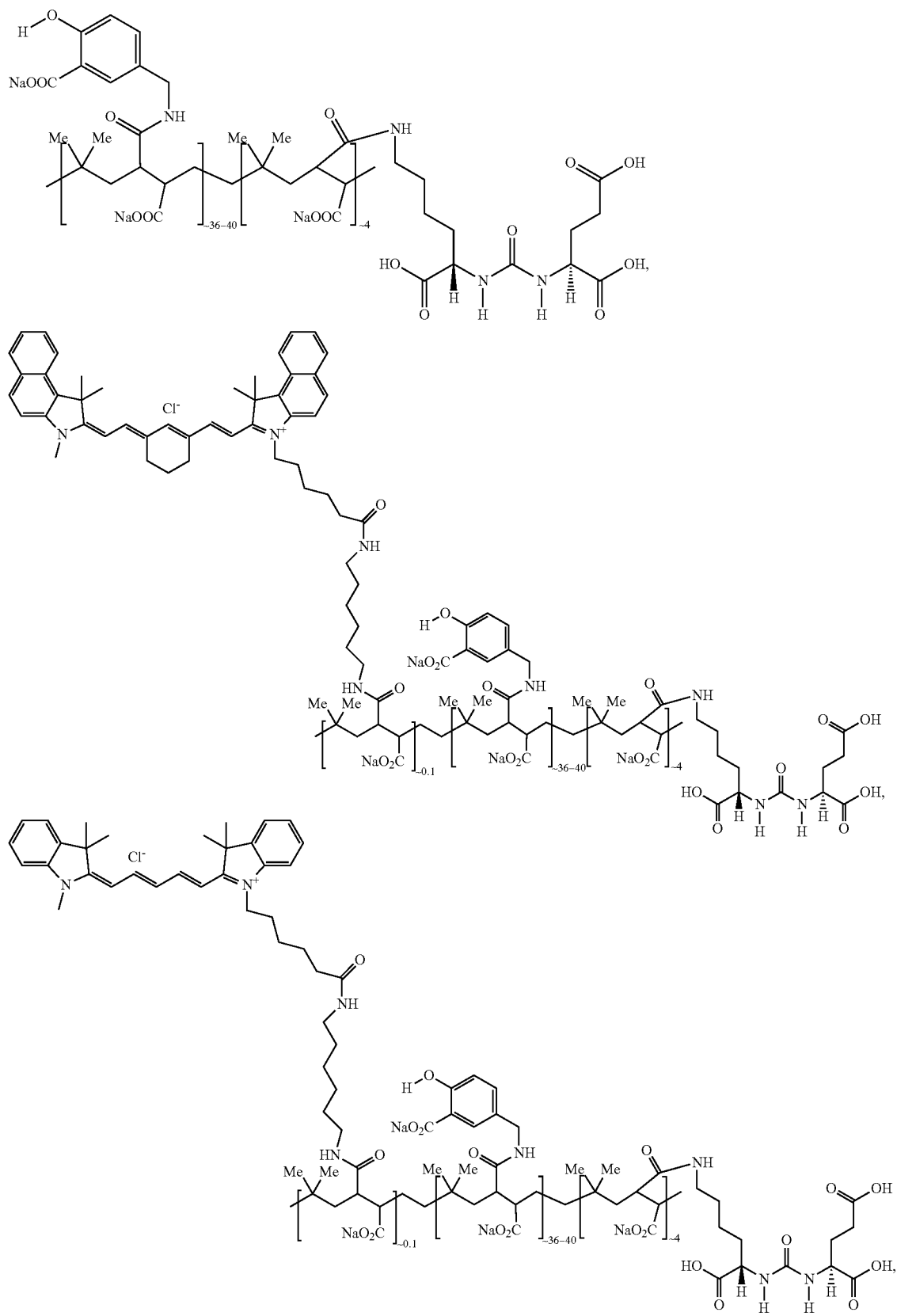

-continued
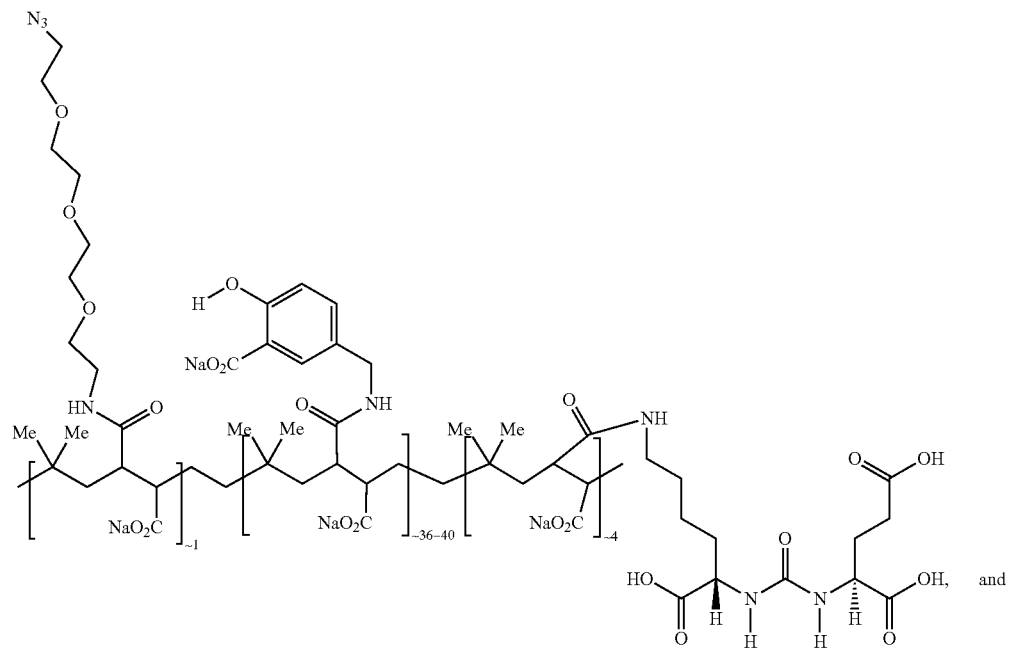
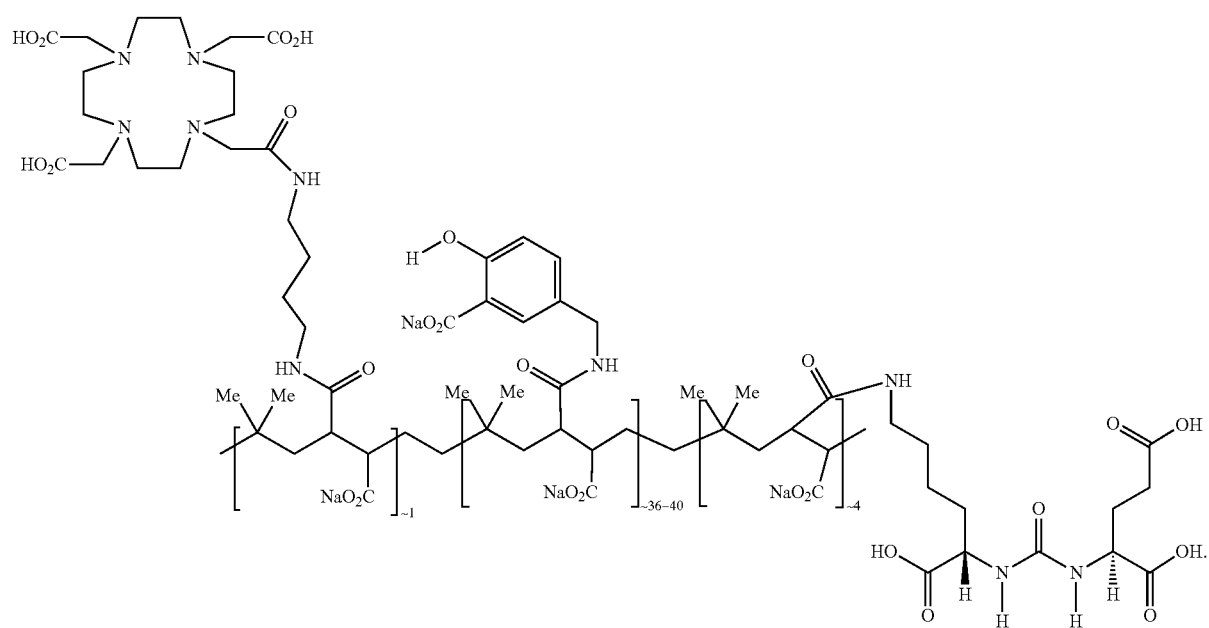

In other representative embodiments, the compound of formula (I) is selected from the group consisting of:

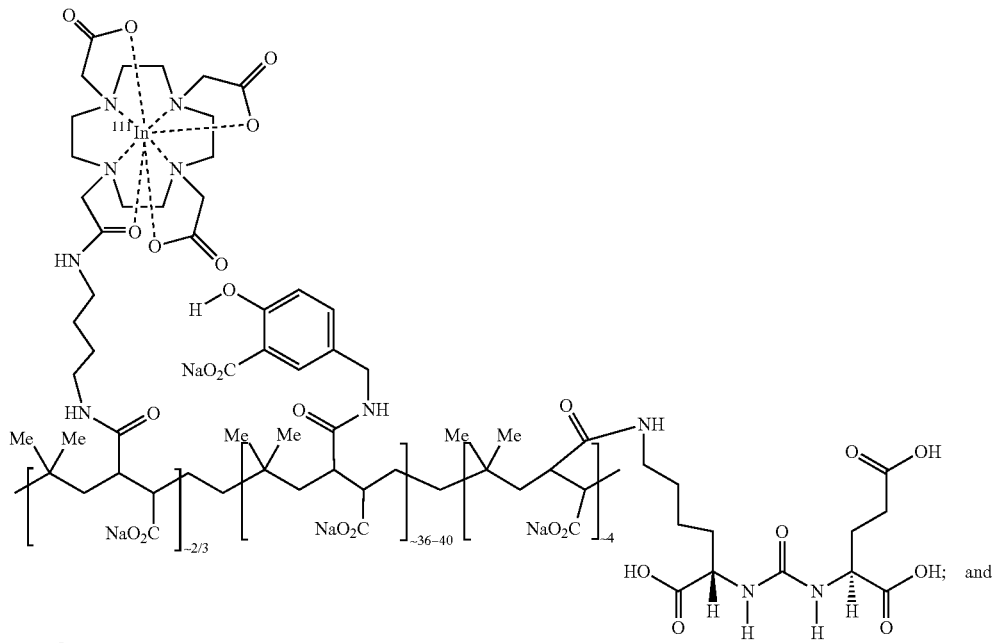

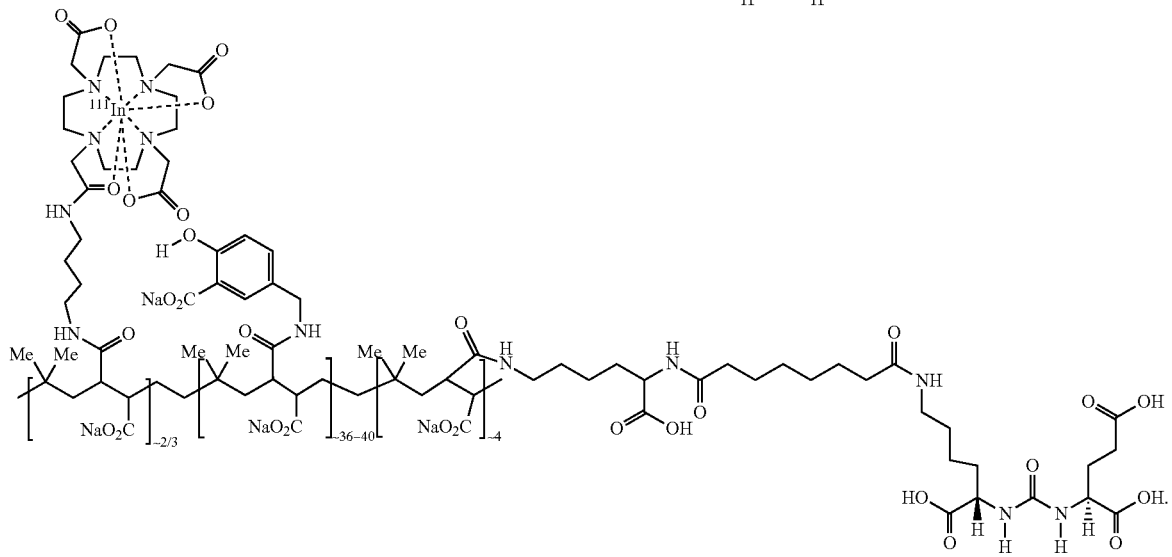

In further embodiments the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In yet more certain embodiments, the one or more PSMA-expressing tumors or cells is a prostate tumor or cell. In some embodiments, the tumor cells express PSMA, such as prostate tumor cells or metastasized prostate tumor cells.

In other embodiments, the one or more PSMA-expressing tumors or cells is found in vitro, in vivo or ex vivo. In further embodiments, the one or more PSMA-expressing tumors or cells is present in a subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In other particular embodiments, the method comprises further measuring a chemical shift change of exchangeable protons in said MRI contrast agent. In other embodiments, the one or more PSMA-expressing tumors or cells is imaged using CEST MRI. In yet other embodiments, the one or more PSMA-expressing tumors or cells is imaged using FLEX MRI.

The methods of the presently disclosed subject matter are useful for diagnosing, based on an image of one or more PSMA-expressing tumors or cells in a subject, whether the subject may have a particular disease (e.g., prostate cancer, hormone-refractory disease, metastatic diseases and tumor neovasculature, and the like). The methods also allow monitoring, based on an MR image of one or more PSMA-expressing tumors or cells in a subject, progression or regression of a disease or condition in the subject. The methods further also allow treating and/or preventing a disease or condition in a subject in need thereof.

As used herein, the term "treating" can include reversing, alleviating, inhibiting the progression of, preventing or reducing the likelihood of the disease, or condition to which such term applies, or one or more symptoms or manifestations of such disease or condition.

"Preventing" refers to causing a disease, condition, or symptom or manifestation of such, or worsening of the severity of such, not to occur.
Accordingly, the presently disclosed compounds can be administered prophylactically to prevent or reduce the incidence or recurrence of the disease, or condition.

The disease or condition is selected from the group consisting of prostate cancer, hormone-refractory disease, metastatic diseases and tumor neovasculature. In some other embodiments, the imaging is performed in combination with positron emission tomography (PET). In yet other embodiments, the imaging is performed in combination with single-photon emission computed tomography (SPECT).

The CEST approach of the presently disclosed subject matter can be further extended to designing other novel responsive agents for molecular and cellular MRI applications. Certain design criteria for creating MRI contrast agents can be found in Que et al. (Chem Soc. Rev. 2010, 39, 51-60) and Hyman et al. (Coordination Chemistry Reviews, 256 (2012), 2333-2356).

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) and formula (II) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2$O— is equivalent to —O$CH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, alkylamino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{2S}$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$); —CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH (CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

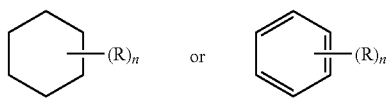

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

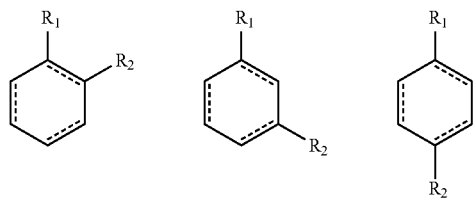

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R"', wherein R', R", and R"' are each independently selected from the group consisting of alkyl groups. Additionally, R', R", and/or R"' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)— or (S)— or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

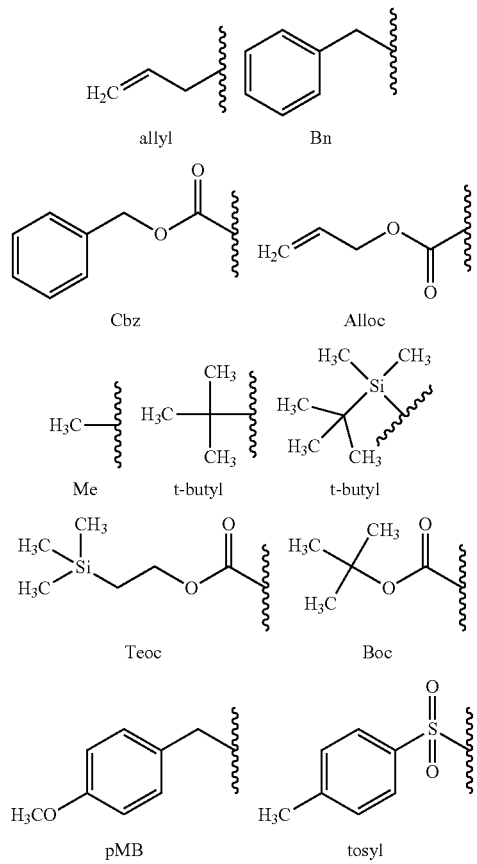

-continued

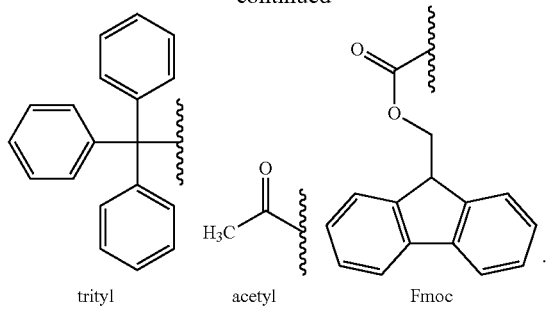

trityl     acetyl     Fmoc

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Salicylic Acid Modified Polymeric Platform CEST Contrast Agents Targeting Prostate-Specific Membrane Antigen Contrast agents have a significant role in clinical magnetic resonance (MR) imaging. Existing clinically approved contrast agents work by lowering the longitudinal ($T_1$) or transverse ($T_2$) relaxation times of water protons that come into close contact with the agent. Any image contrast produced by the agent generally reflects nonselective distribution of the complex in tissues by a crude physical clearance mechanism.

Recently, a new type of MRI contrast that relies on direct chemical exchange of protons with bulk water has been developed and is referred to as chemical exchange saturation transfer (CEST) MRI. CEST MRI is a technique in which concentration marker molecules are labeled by either saturating or labeling their exchangeable proton spins by radio-frequency (RF) irradiation. If such saturation or labeling can be achieved rapidly, i.e., before the spin exchanges, exchange of such labeled spins with water leads to transfer of the magnetization, allowing indirect detection of the solute via the water resonance through a change in signal intensity in MRI.

The integral membrane protein, prostate-specific membrane antigen (PSMA) is an increasingly important target for both imaging and therapy of prostate cancer (PC), particularly for the castration-resistant sub type that claims most lives. Conventional PC imaging is generally performed with magnetic resonance (MR) imaging to provide high resolution anatomic and functional data. It has been recently reported that PSMA could serve as a biomarker for MR-based molecular imaging by combining our well-optimized PSMA-targeting low molecular weight (LMW) urea-linker construct with preformed $Gd^{III}$-DOTA chelates on a multimeric platform. Moderate but significant $T_1$ contrast enhancements were generated, specifically in PSMA+ PC3 cells and in PSMA+ PC3 xenograft models.

The goal of this work is to generate a targeted CEST-based contrast agent for MR imaging of PSMA expression. The design of the presently disclosed CEST contrast agents is based on previous study on contrast enhancement multimeric platform.

As an initial study, poly(maleic anhydride)s, as commonly available industry materials, seem to be good candidates. There are several advantages for these materials. First, they could react mildly with free amines and generate water soluble carboxylate polymers. Second, maleic anhydride and substituted ethylene copolymers are available at different size with molecular weight from thousands D to hundreds kD. In order to incorporate salicylic acid to these polymers, commercially available 5-(aminomethyl)-2-hydroxy-benzoic acid (46) as the functional CEST probe was chosen. The reactive amino group is place at R5 position to avoid its effect to the USHY signal. As shown in Scheme 1, the synthesis of poly(salicylic acids) is just simply mixing the poly(substituted ethylen-alt-maleic anhydride) and 5-(aminomethyl)-2-hydroxy-benzoic acid in DMSO with excess triethylamine. After the reaction complete, the products could be easily purified by dialysis and can be obtained in high yield and purity. In addition, these water soluble polymeric contrast agents can be generated in gram scale conveniently.

Scheme 1

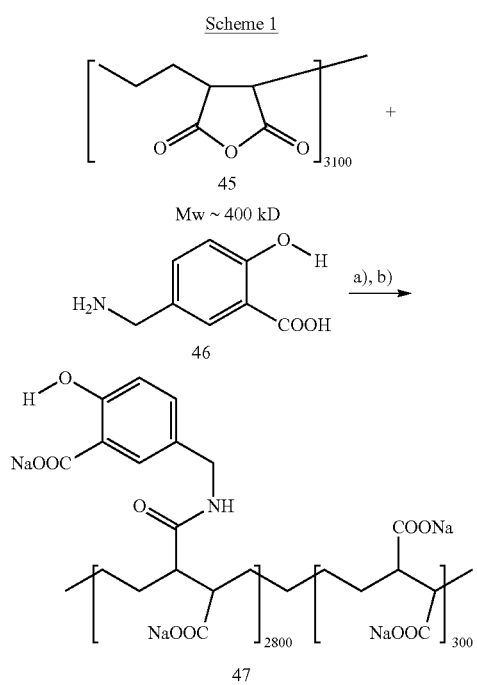

a) Et3N/DMSO;
b) dialysis with 1M NaHCO3 and then water.

As a proof of principle study, poly(ethylen-alt-maleic anhydride) (45) with a molecular weight around 400 kD, which contains around 3100 units was chosen. After purification, 1H-NMR clearly indicated the incorporation of salicylic acid. The calculated efficiency based on integration is around 90% for the polymer, as shown in FIG. 1. Based on the size of the starting material, the formed polymer contained 2800 salicylic acid units on average. The molecular weights of the synthesized polymers were further proved by electophoresis.

The material 47 showed significant CEST contrast at 9.2 ppm. As shown in FIG. 2, linear relationship between the contrast and the concentration was observed at relative low concentration. In principle, this type of material could be conjugated to antibodies towards receptor imaging.

CEST Contrast of the Polymer 47 at Micromolar Level Condition and pH Dependence.

CEST data were obtained at 10 mM concentration, pH 7.3-7.4, $t_{sat}$=3 sec, ω1=3.6 µT and 37° C. The contrast at 9.2 ppm was plotted at different concentrations.

Interestingly, CEST property of 47 showed great pH dependence. The contrast changes from pH 6 to 8 were plotted in FIG. 3. As shown, the CEST signal dropped dramatically, when the pH dropped below 7.4.

Example 2

Synthesis of SA PolyCEST (SA-T) and Control CEST Copolymer (SA-UT)

The SA modified polymeric platform (referred to herein as "SA PolyCEST" or SA-T) was synthesized by reacting commercially available poly(isobutylene-alt-maleic anhydride)$_{40}$ ($M_w$=6,000 g per mol) with 5-(aminomethyl)-2-hydroxy-benzoic acid and PSMA-targeting Lys-Glu with a ratio (1/40/4) in DMSO stirring at room temperature for 16 h in presence of excess diisopropylethylamine. The reaction solution was then diluted with 1 M sodium bicarbonate and purified by ultrafiltration spin column (3 kD Mol wt cut off) using water to remove excess salt. The structures of the copolymers are shown in FIG. 1. Based on previous experience, the ratio of CEST contrast and targeting urea was kept around 10:1 in the final PolyCEST product so that it has enough CEST contrast from salicylic acid and also PSMA binding affinity from Ly-Glu urea. Based on the linear and flexible nature of the polymer, no linker moiety was attached to the urea binding part in this first generation of copolymer.

A control CEST copolymer (SA-UT) without targeting moiety also was prepared using poly(isobutylene-alt-maleic anhydride)$_{40}$ and 3-amino-salicylic acid (1/40). Copolymers were characterized by $^1$H NMR in $D_2O$.

These CEST contrast agents are amphiphilic in nature because the copolymer stems from the hydrophobic isobutylene chains grafted to the polymer backbone in combination with the hydrophilic carboxylic groups of maleic acid. The binding affinities of the new agents, expressed as $K_i$ values, were determined using amplex red assay and in cell-based assay. In amplex red assay, Ki values were ranged from 1.47-3.16 nM for SA-T 79-128 nM for SA-UT where ZJ43 was 0.09-0.1 nM. In the cell based assay, $EC_{50}$ values are 4.4-14 µM for SA-T, 66-890 µM for SA-UT and 70-128 nM for ZJ43.

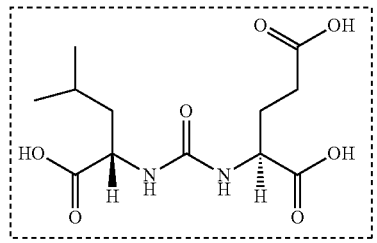

ZJ43

Example 3

In Vitro and In Vivo Characterization of SA-T

Both cellular (same method to prepare the cell pellets) and in vivo CEST imaging for both SA-T (n=5) and SA-UT (n=2) have been studied, using PSMA+PC3 PIP (right) and PSMA-PC3 flu (left) tumor xenografts at the lower flank of male SCID/NOD mice. In vivo CEST-MR images were acquired on a Bruker Biospec 11.7T MR scanner.

In Vitro Characterization of SA-T.

The results are displayed at four concentrations of the targeted SA-T polymeric diaCEST: 25, 12.5, 6.25, and 3.125 mg/mL, respectively, as disclosed in FIG. 2A. The results obtained show that the CEST contrast is dependent of the concentration of the PSMA-targeted probe, which is detectable below 3 mg/mL. Based on the quality of these data, in vivo studies were carried out as described immediately herein below.

In Vivo Characterization of SA-T PolyCEST.

Male SCID/NOD mice bearing two prostate tumors (PSMA+PC3 PIP and PSMA+PC3 flu) were injected with 100 of 25 mg/mL SA-T or SA-UT PolyCEST probe in phosphate buffered saline (PBS). Fifteen offsets were collected from 7.2 ppm to 11.4 ppm with CEST imaging parameters: $t_{sat}$=2 s, $B_i$=5.9 µT, FOV: 350 µm×350 µm. In vivo data after injection of both targeted ((SA)$_{40}$-Urea) and untargeted ((SA)$_{40}$) CEST polymers into mice bearing prostate tumors are disclosed in FIGS. 4B-4C. The CEST imaging process includes three components: image collection, WASSR correction, and CNR filtering and contour leveling. A significant contrast was observed 90 minutes post-injection of targeted polymer SA-T PolyCEST (upper panels), whereas no contrast was observed for the untargeted polymer (SA-UT PolyCEST).

Example 4

Synthesis of SA PolyCEST (SA-T) and Control CEST Copolymer (SA-UT) Coupled with a Dye Synthesis of SA PolyCEST (SA-T) Coupled with Cy7.5 (Obtained from Lumiprobe) (Table 2).

100 mg of MAA polymer (poly(isobutylene-alt-maleic anhydride)$_{40}$) and 35 mg of 5-methyl amino-2-hydroxybenzoic acid were added to a glass vial. 3.31 µL of 11-azido (1.10 g/mL) were added to the mixture. 2 mL of DMSO were added to dissolve and a stir bar was added. 290 µL of DIEA (0.742 g/mL) were added to the vial and the solution was stirred. 29 mg of PSMA Urea were added to the vial, followed by 1.37 mg of Cy7.5 Amine.

TABLE 1

PolyCEST (SA-UT), Green Dye

| Compound | MW | Ratio | Weight Taken (g) | Volume (mL) | Moles (mol) | |
|---|---|---|---|---|---|---|
| MAA | 6000 | 1 | 0.1 | | 1.66667E−05 | DMSO (2 mL) |
| 5-methyl amino-2-hydroxybenzoic acid | 203 | 40 | 0.135333333 | | 0.000666667 | |
| 11-azido-3,6,9-trioxaachardrlamide (d = 1.10 g/mL) | 218.25 | 1 | 0.0036375 | 0.003306818 | 1.66667E−05 | |
| DIEA (d = 0.742 g/mL) | 129 | 100 | 0.215 | 0.289757412 | 0.001666667 | |
| Cy7.5 Amine (green) | 819.99 | 0.1 | 0.00136665 | | 1.66667E−06 | DMSO 20 μL |

TABLE 2

PolyCEST (SA-T), Green Dye

| Compound | MW | Ratio | Weight Taken (g) | Volume (mL) | Moles (mol) | |
|---|---|---|---|---|---|---|
| MAA | 6000 | 1 | 0.1 | | 1.66667E−05 | DMSO (2 mL) |
| 5-methyl amino-2-hydroxybenzoic acid | 203 | 40 | 0.135333333 | | 0.000666667 | |
| 11-azido-3,6,9-trioxaachardrlamide (d = 1.10 g/mL) | 218.25 | 1 | 0.0036375 | 0.003306818 | 1.66667E−05 | |
| DIEA (d = 0.742 g/mL) | 129 | 100 | 0.215 | 0.289757412 | 0.001666667 | |
| PSMA Urea | 435 | 4 | 0.029 | | 6.66667E−05 | |
| Cy7.5 Amine (green) | 819.99 | 0.1 | 0.00136665 | | 1.66667E−06 | DMSO 20 μL |

Example 5

Biodistribution Studies of Control CEST Copolymer $^{111}$In-DOTA-SA-UT

TABLE 3

Tissue biodistibution properties of 1, untargeted polymer, $^{111}$In-DOTA-SA-UT in PC3 PIP and PC3 flu tumor bearing mice (n = 4)

| | 1 H | 2 H | 4 H | 24 h |
|---|---|---|---|---|
| Blood | 2.46 ± 0.25 | 1.34 ± 0.06 | 0.77 ± 0.02 | 0.15 ± 0.09 |
| heart | 1.50 ± 0.32 | 1.28 ± 0.13 | 1.40 ± 0.02 | 1.49 ± 0.28 |
| lung | 3.10 ± 0.15 | 2.76 ± 0.24 | 2.99 ± 0.03 | 2.63 ± 0.21 |
| liver | 53.72 ± 5.26 | 59.57 ± 5.93 | 62.94 ± 0.02 | 72.42 ± 5.31 |
| stomach | 1.39 ± 0.11 | 1.40 ± 0.16 | 1.58 ± 0.02 | 1.74 ± 0.22 |
| pancreas | 1.20 ± 0.07 | 1.28 ± 0.09 | 1.49 ± 0.04 | 1.13 ± 0.78 |
| spleen | 23.04 ± 2.15 | 24.51 ± 3.22 | 28.04 ± 0.12 | 23.02 ± 10.13 |
| fat | 0.29 ± 0.14 | 0.22 ± 0.08 | 0.24 ± 0.17 | 0.17 ± 0.18 |
| kidney | 18.92 ± 0.62 | 20.21 ± 0.91 | 24.41 ± 4.13 | 20.06 ± 2.21 |
| muscle | 0.39 ± 0.12 | 0.32 ± 0.20 | 0.40 ± 0.01 | 0.34 ± 0.15 |
| small intestine | 1.99 ± 0.75 | 2.40 ± 0.55 | 2.49 ± 0.02 | 1.08 ± 0.89 |
| large intestine | 1.11 ± 0.27 | 1.09 ± 0.93 | 1.28 ± 0.04 | 1.62 ± 0.92 |
| bladder | 1.08 ± 0.35 | 0.53 ± 0.16 | 0.75 ± 0.11 | 0.67 ± 0.45 |
| PC-3 PIP | 1.44 ± 0.63 | 1.32 ± 0.37 | 0.57 ± 7.99 | 0.90 ± 0.35 |
| PC-3 flu | 0.82 ± 0.19 | 0.74 ± 0.84 | 1.19 ± 0.06 | 0.74 ± 0.28 |

Example 6

Biodistribution and Cell Uptake Studies of $^{111}$In-DOTA-SA-T

TABLE 4

Tissue biodistribution data per time point for 2, targeted polymer ($^{111}$In-DOTA-SA-T) in PC3 PIP and PC3 flu tumor bearing mice (n = 4)

|  | 1 H | 2 H | 4 H |
|---|---|---|---|
| Blood | 1.26 ± 0.55 | 1.33 ± 1.41 | 0.58 ± 0.13 |
| heart | 1.36 ± 0.22 | 0.86 ± 0.35 | 0.86 ± 0.35 |
| lung | 1.88 ± 0.24 | 1.63 ± 0.49 | 1.62 ± 0.49 |
| liver | 56.82 ± 8.95 | 41.11 ± 10.49 | 64.93 ± 52.91 |
| stomach | 3.13 ± 0.43 | 2.43 ± 1.30 | 2.40 ± 1.27 |
| pancreas | 2.95 ± 0.80 | 1.82 ± 0.93 | 2.23 ± 1.39 |
| spleen | 22.87 ± 5.38 | 18.26 ± 7.65 | 19.13 ± 8.65 |
| fat | 0.75 ± 3.66 | 0.422 ± 0.18 | 0.39 ± 0.17 |
| kidney | 67.52 ± 15.20 | 57.17 ± 12.94 | 57.75 ± 13.75 |
| muscle | 0.66 ± 0.19 | 0.62 ± 0.08 | 0.58 ± 0.035 |
| small intestine | 4.56 ± 1.02 | 4.48 ± 2.81 | 4.91 ± 3.29 |
| Salivary gland | 3.75 ± 0.75 | 2.36 ± 0.96 | 3.00 ± 1.70 |
| bladder | 7.45 ± 3.32 | 2.61 ± 0.81 | 5.44 ± 4.47 |
| PC-3 PIP | 4.29 ± 0.79 | 3.63 ± 1.53 | 3.58 ± 1.32 |
| PC-3 flu | 1.78 ± | 0.71 ± 0.31 | 0.84 ± 0.49 |

Cell Up Take Study.

The radiolabeled $^{111}$In-DOTA-SA-T, 2, was incubated in PC3 PIP and PC3 cell at 37° C. for 2 hours followed by washing with PBS, percent of uptake in PC PIP was 14.30 and PC3 flu 4.6, showing the specificity of the agent in cellular level ($^{111}$In-DOTA-SA-T) in PSMA-expressing cells.

TABLE 5

Cell up take Study for 2, targeted polymer ($^{111}$In-DOTA-SA-T)

|  | % of uptake |
|---|---|
| PSMA + PC 3 PIP | 14.30753 |
| PSMA − PC 3 flu | 4.62232 |

Example 7

Biodistribution Studies of $^{111}$In-DOTA-SA-Lys-Suberate-T

TABLE 6

Tissue biodistribution data per time point for 3, targeted polymer ($^{111}$In-DOTA-SA-Lys-suberate-T) in PC3 PIP and PC3 flu tumor bearing mice (n = 4)

|  | 1 H | 2 H | 4 H |
|---|---|---|---|
| Blood | 0.86 ± 0.22 | 0.50 ± 0.24 | 0.39 ± 0.19 |
| heart | 0.92 ± 0.15 | 0.59 ± 0.27 | 0.71 ± 0.19 |
| lung | 1.52 ± 0.33 | 1.25 ± 0.56 | 1.40 ± 0.23 |
| liver | 49.69 ± 9.32 | 34.60 ± 16.10 | 43.27 ± 13.21 |
| stomach | 1.53 ± 0.22 | 1.30 ± 0.58 | 1.65 ± 0.40 |
| pancreas | 1.52 ± 0.24 | 1.12 ± 0.52 | 1.41 ± 0.43 |
| spleen | 17.43 ± 4.10 | 11.53 ± 5.16 | 13.12 ± 1.90 |
| fat | 0.30 ± 0.23 | 0.39 ± 0.21 | 0.27 ± 0.05 |
| kidney | 50.72 ± 5.26 | 46.60 ± 20.86 | 53.00 ± 8.06 |
| muscle | 0.48 ± 0.18 | 0.50 ± 0.28 | 0.47 ± 0.15 |
| small intestine | 2.85 ± 1.0 | 2.09 ±0.93 | 2.66 ± 0.97 |
| Salivary gland | 2.26 ± 0.37 | 1.72 ± 0.84 | 2.45 ± 1.23 |
| bladder | 3.10 ± 2.43 | 3.14 ± 2.47 | 3.82 ± 3.59 |
| PC-3 PIP | 2.84 ± 0.49 | 2.34 ± 1.07 | 2.49 ± 0.21 |
| PC-3 flu | 1.12 ± 10.12 | 0.45 ± 0.20 | 0.50 ± 0.10 |

Example 8

Discussion

A salicylic acid (SA) analog when grafted on a polymeric platform is able to produce significantly enhanced contrast in MR images detectable through chemical exchange saturation transfer (CEST). The SA PolyCEST has been further modified with Glu-Lysine urea, an inhibitor of prostate-specific membrane antigen (PSMA), a cell surface protein that is over expressed in most prostate cancers, including hormone-refractory and metastatic disease and tumor neovasculature. PolyCEST compounds are water soluble organic polymeric materials that provide a general type of MRI organic contrast agents that produce significantly enhanced contrast in MR imaging, and because of the targeting aspect of the polymer, specific enhancement in PSMA-expressing tumor xenografts through CEST or FLEX imaging are expected.

The PSMA targeted SA PolyCEST retains its high CEST contrast sensitivity, as well as its binding affinity for PSMA. Using this PSMA-targeted SA PolyCEST, the first example of in vivo PSMA-specific CEST contrast enhancement in mouse xenografts has been demonstrated. This SA PolyCEST platform also could be used for other receptor-based MR imaging, such as HER-2/neu receptors, alpha V beta 3 integrin receptors, CXCR-4 alpha-chemokine receptors or others. Further, by attaching azide/alkyne group on the polymer backbone, any imaging and/or therapeutic agent can be attached to the polymer via click chemistry.

Moreover, other polymeric platforms could be used to synthesize salicylic acid-based polymeric CEST contrast agents targeting PSMA including, but not limited to, polyallyamine and polyethyleneimine (PLL).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control.

Airan, R. D. et al., *Magn. Reson. Med.* 2012, 68, 1919-1923.
Cai, K. J. et al., *Nat. Med.* 2012, 18, 302-306.

Caravan, P. *Chem, Soc. Rev.* 2006, 35, 512-523. I.
Chan, K. W. et al., *Magnetic resonance in medicine: official journal of the Society of Magnetic Resonance in Medicine/Society of Magnetic Resonance in Medicine* 2012, 68, 1764-1773.
Haris, M. et al., *Neurosci. Meth.* 2013, 212, 87-93.
Hancu, W. T. et al., *Acta Radiol.* 2010, 51, 910-923.
Jin, T. et al., *Magn. Reson. Med.* 2011, 65, 1448-1460.
Kubicek, V. and Toth, E. in Advances in Inorganic Chemistry, Vol 61 (Eds R. VanEldik, C. D. Hubbard), Elsevier Academic Press Inc, San Diego, 2009, pp. 63-129.
Ling, W. et al., *Proc. Natl. Acad. Sci. USA* 2008, 105, 2266-2270.
Liu, G. et al. "Nuts and Bolts of CEST Imaging", *NMR in Biomed.* 2013, Doi: 10.1002/nbm.2899.
Liu, G. et al., High-Throughput Screening of Chemical Exchange Saturation Transfer MR Contrast Agents. *Con. Media. & Mol. Imag.* 2010; 5(3): 162-170.
Longo D. L. et al. Iopamidol as a responsive MRI-chemical exchange saturation transfer contrast agent for pH mapping of kidneys: In vivo studies in mice at 7 T. *Magn. Reson. Med.* 2011; 65(1):202-211.
McMahon, M. T., et al., *Magn. Reson. Med.* 2008, 60, 803-812.
Salhotra, B. Lal, J. Laterra, P. Z. Sun, P. C. M. van Zijl, J. Y. Zhou, NMR Biomed 2008, 21, 489-497.
Sherry A D, and Woods M. Chemical exchange saturation transfer contrast agents for magnetic resonance imaging. *Annual Review of Biomedical Engineering* 2008; 10:391-411.
Terreno, E. et al., *Contrast Media Mol. Imaging* 2010, 5, 78-98.
Torrealdea, F. et al., *Contrast Media Mol. Imaging* 2013 doi: 10.1002/cmmi.1522.
Van Zijl, P. C. M. et al., *Proc. Natl. Acad. Sci. USA* 2007, 104, 4359-4364.
Van Zijl P. C. and Yadav N. N. Chemical exchange saturation transfer (CEST): what is in a name and what isn't? *Magn. Reson. Med* 201165(4):927-948.
Ward, K. M. et al., *J. Magn. Reson.* 2000, 143, 79-87.
Yang, X. et al. Salicylic acid and analogues as diaCEST MRI contrast agents with highly shifted exchangeable proton frequencies. *Angew Chem Int Ed Engl.* 2013; 52:8116-19.
International PCT Patent Application Publication No. PCT/US2014/038444 to Yang, X. et al., for Compositions and methods for chemical exchange saturation transfer (CEST) based magnetic resonance imaging (MRI), published 2014 Nov. 20.
International PCT Patent Application Publication No. PCT/US2008/007947 to Pomper M. G. et al., for Labeled inhibitors of prostate specific membrane antigen (PSMA), biological evaluation, and use as imaging agents, published 2009 Feb. 12.
International PCT Patent Application Publication No. PCT/US2008/013158 to Chandran S. S. et al., for Prostate specific membrane antigen targeted nanoparticles for therapy of prostate cancer, published 2009 Jun. 4.
International PCT Patent Application Publication No. PCT/US2010/028020 to Pomper M. G. et al., for PSMA-targeting compounds and uses thereof, published 2010 Sep. 23.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I), formula (II), formula (III), or formula (IV):

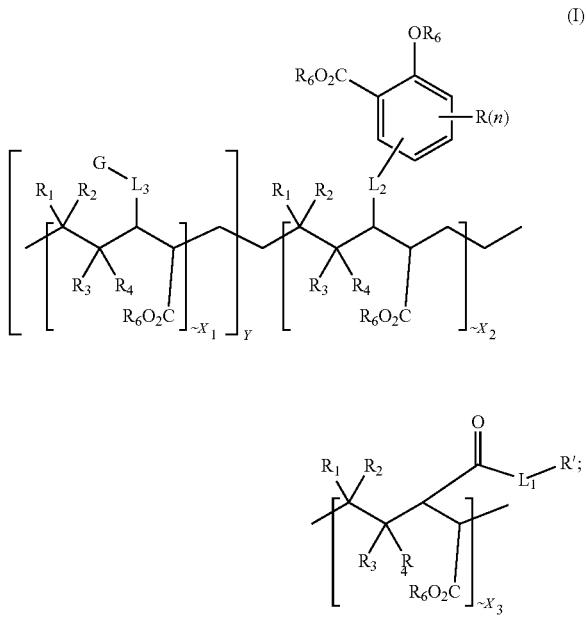

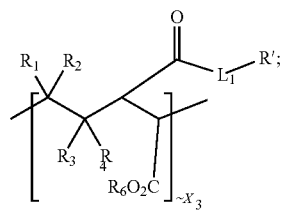

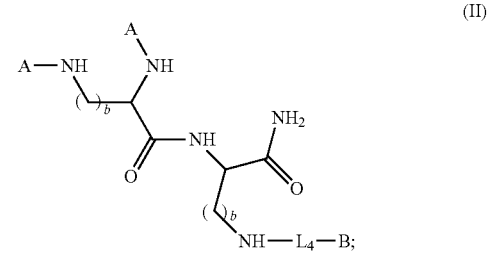

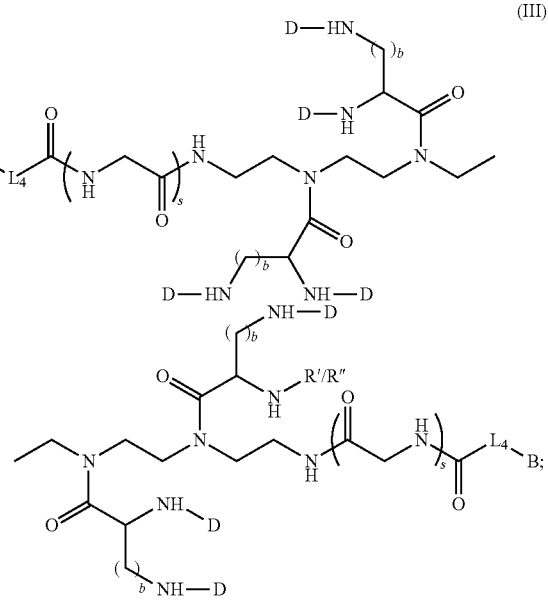

-continued

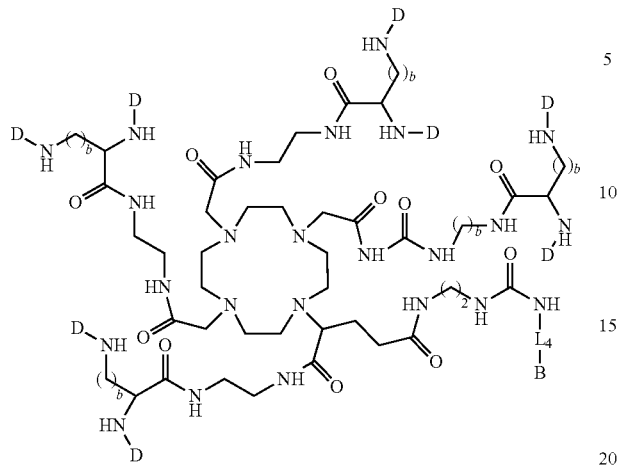

(IV)

wherein:
R' is

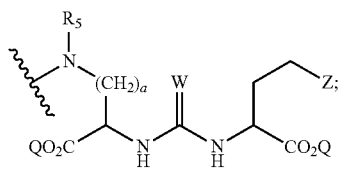

B is R' or

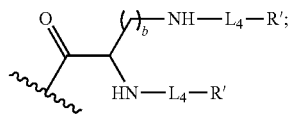

Z is tetrazole or CO$_2$Q;
Q is H or a protecting group;
W is O or S;
a is an integer selected from the group consisting of 0, 1, 2, 3 and 4;
b is an integer selected from the group consisting of 1, and 4;
n is independently an integer selected from the group consisting of 0, 1, 2, and 3;
s is an integer selected from the group consisting of 0, 1, 2, 3 and 4;
each R is independently selected from the group consisting of hydrogen, substituted or unsubstituted alkyl, alkoxyl, hydroxyl, hydroxyalkyl, carboxyl, acyl, carbonyl, carbamoyl, alkylcarbamoyl, halogen, amino, alkylamino, nitro, nitrile, amide, haloalkyl, aryl, cycloalkyl, aralkyloxyl, and —SO$_3$H;
R$_1$, R$_2$, R$_3$ and R$_4$ are independently selected from the group consisting of H or substituted or unsubstituted linear or branched alkyl, substituted or unsubstituted aryl, and alkoxyl;
R$_5$ is independently H, C$_1$-C$_4$ alkyl or C$_2$-C$_{12}$ aryl;
each R$_6$ is independently H, Na or a protecting group;
L$_1$ is a linking group selected from the group consisting of —(CH$_2$)$_m$—, —(CH$_2$—CH$_2$—O)$_t$—, —(O—CH$_2$—CH$_2$)$_t$—, —NR$_7$—(CHR$_8$)$_m$—NR$_7$—C(=O)—(CH$_2$)$_m$—C(=O)— and —NR$_7$—(CHR$_8$)$_m$—C(=O)—NR$_7$—(CH$_2$)$_m$—C(=O)—;
L$_2$ is a linking group selected from the group consisting of —(CH$_2$)$_m$—NR$_7$—C(=O)—(CH$_2$)$_p$—, —(CH$_2$)$_m$—C(=O)—NR$_7$—(CH$_2$)$_p$—, —(CH$_2$)$_m$—NR$_7$—C(=O)—NR$_7$—(CH$_2$)$_p$—, —(CH$_2$)$_m$—NR$_7$—C(=O)—NR$_7$—(CH$_2$)$_p$—, —(CH$_2$)$_m$—O—C(=O)—NR$_7$—, —CH$_2$)$_m$—O—C(=O)—NR$_7$—(CH$_2$)$_p$—, —(CH$_2$)$_m$—NR$_7$—C(=O)—O—CH$_2$)$_p$—, —(CH$_2$)$_m$—NR$_7$—C(=O)—O—(CH$_2$)$_p$—, —SO$_2$—NH—(CH$_2$)$_p$—, and —(CH$_2$)$_m$—SO$_2$—NH—(CH$_2$)$_p$—;
L$_3$ is a linking group selected from the group consisting of —C(=O)—NR$_7$—(CH$_2$)$_m$—, —C(=O)—NR$_7$—(CH$_2$)$_m$—NR$_7$—, —C(=O)—NR$_7$—(CH$_2$)$_m$—C(=O)—NR$_7$—, —C(=O)—NR$_7$—(CH$_2$)$_m$—NR$_7$—C(=O)—, —C(=O)—NR$_7$—(CH$_2$)$_m$—NR$_7$—C(=O)—NR$_7$—, —C(=O)—NR$_7$—(CH$_2$)$_m$—NR$_7$—C(=O)—(CH$_2$)$_p$—, —C(=O)—NR$_7$—(CH$_2$)$_m$—C(=O)—NR$_7$—(CH$_2$)$_p$—, —C(=O)—NR$_7$—(CH$_2$)$_m$—(O—CH$_2$—CH$_2$)$_t$—, —C(=O)—NR$_7$—(CH$_2$)$_m$—(CH$_2$—CH$_2$—O)$_t$—(CH$_2$)$_p$—, and —C(=O)—NR$_7$—(CH$_2$)$_m$—(O—CH$_2$—CH$_2$)$_t$—C(=O)—NR$_7$—;
L$_4$ is a linking group selected from the group consisting of —(CH$_2$)$_m$—, —C(=O)—(CH$_2$)$_m$—C(=O)—, —C(=O)—(CH$_2$)$_m$—NR$_7$—C(=O)—, —C(=O)—(CH$_2$—CH$_2$—O)$_t$—C(=O)—, —C(=O)—(CHR$_8$)$_m$—C(=O)—, —C(=O)—(CHR$_8$)$_m$—NR$_7$—C(=O)—, —C(=O)—(CH$_2$—CH$_2$—O)$_t$—C(=O)—, and —C(=O)—(O—CH$_2$—CH$_2$)$_t$—C(=O)—;
each R$_7$ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;
each R$_8$ is independently selected from the group consisting of hydrogen, and —COOR$_6$;
m and p are each independently an integer selected from the group consisting of 0, 1, 2, 3, 4, 5, 6, 7 and 8;
t is an integer selected from the group consisting of 1, 2, 3, 4, 5, 6, 7, 8, 9, 10, 11 and 12;
Y is an integer selected from the group consisting of 0 and 1;
G is an azide, an alkyne, a fluoerescent dye moiety that emits light in the visible or near-infrared (NIR) spectrum, or a chelating moiety optionally comprising a metal or a radiometal;
X$_1$ is an integer selected from the group consisting of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and 2;
X$_2$ and X$_3$ are each independently an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40;
A is selected from the group consisting of:

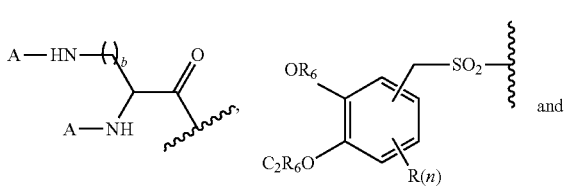

and

-continued
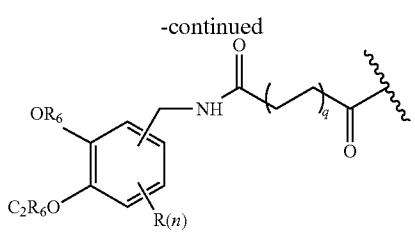
wherein q is an integer selected from the group consisting of 1, 2, 3, 4, and 5;
D is selected from the group consisting of:
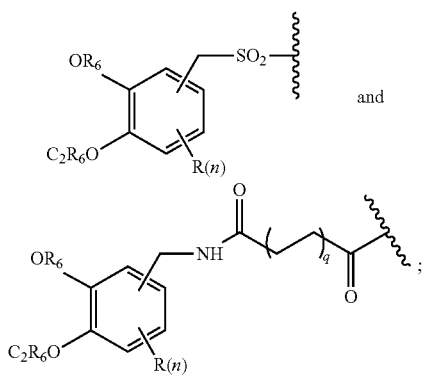
or a salt or a stereoisomer thereof.
2. The compound of claim 1, wherein R' is
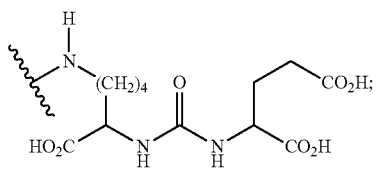
and
B is R' or
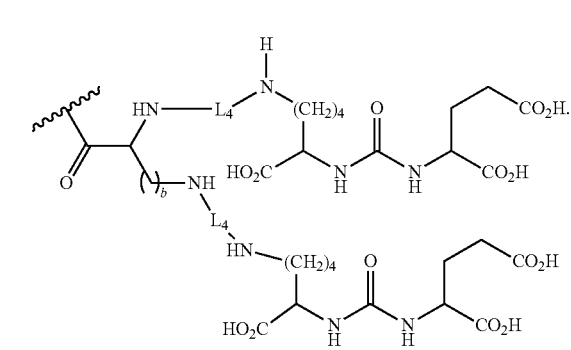
3. The compound of formula (II), wherein the compound is selected from the group consisting of:
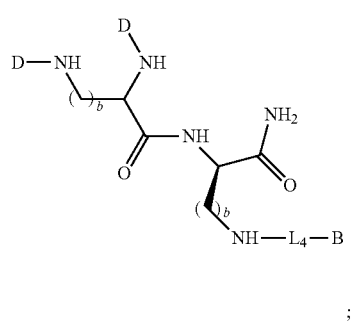
(II)a
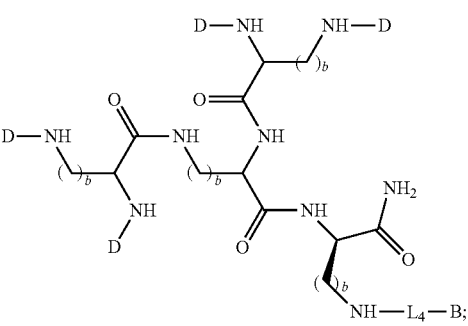
(II)b
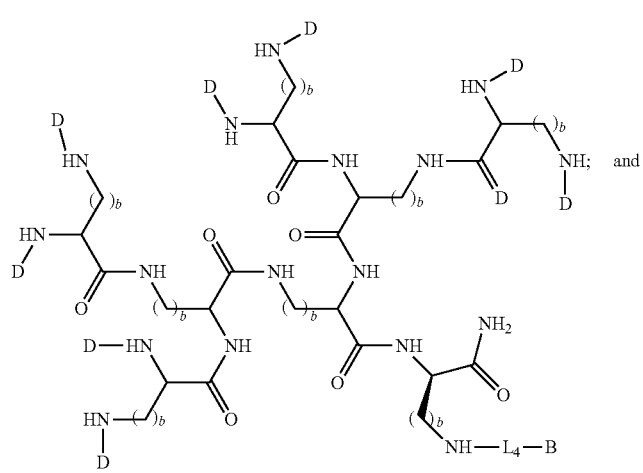
(II)c

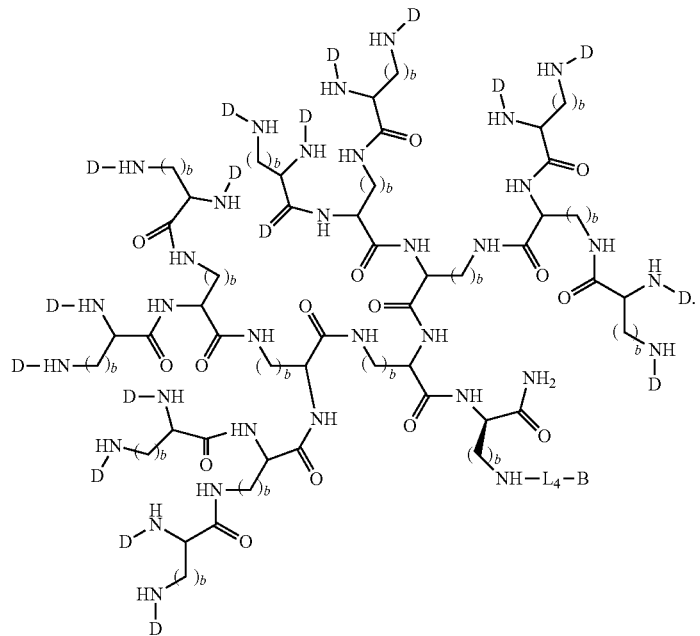
(II)d
4. The compound of claim 1, wherein the ratio of $X_2:X_3$ is about 10:1.
5. The compound of claim 1, wherein the ratio of $X_1:X_2:X_3$ is about 0.1:10:1.
6. The compound of claim 1, wherein the ratio of $X_1:X_2:X_3$ is about 1:10:1.
7. The compound of claim 1, wherein the chelating moiety comprising a metal or a radiometal, is selected from the group consisting of:
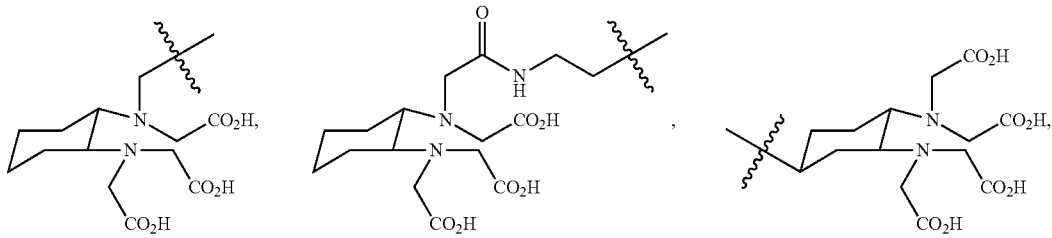
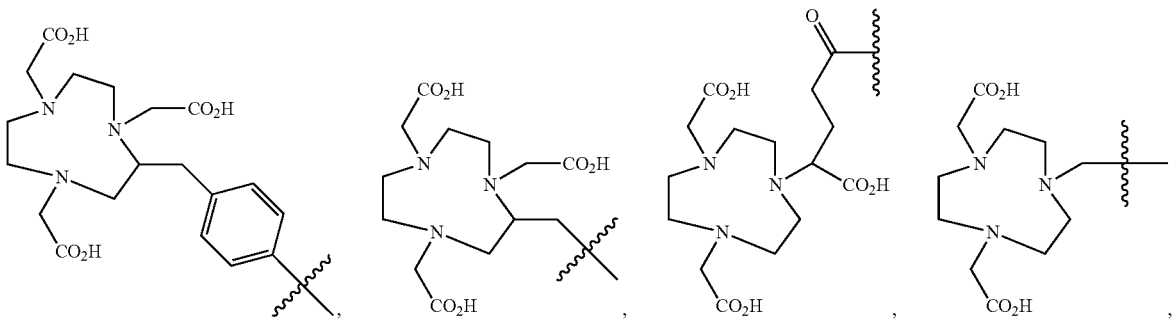

-continued
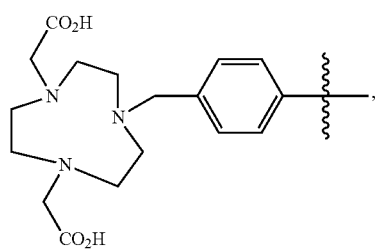
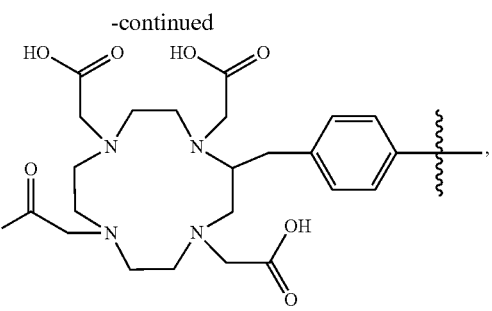
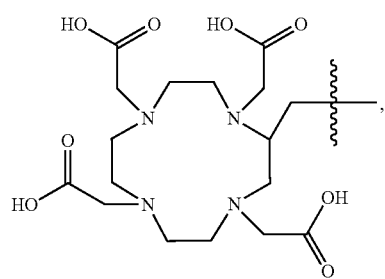
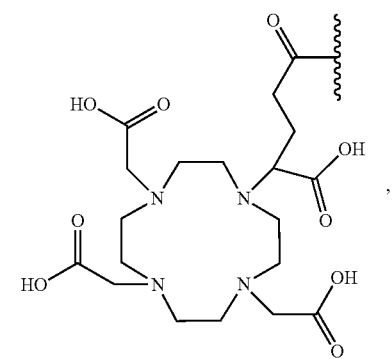
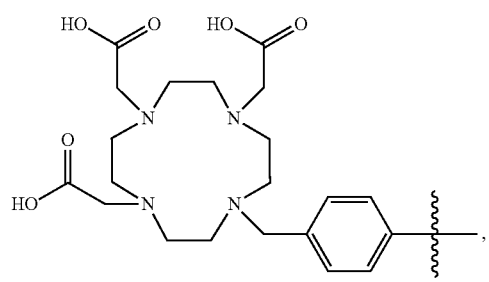
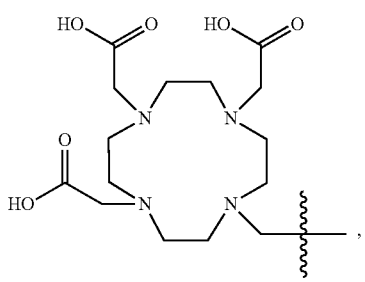
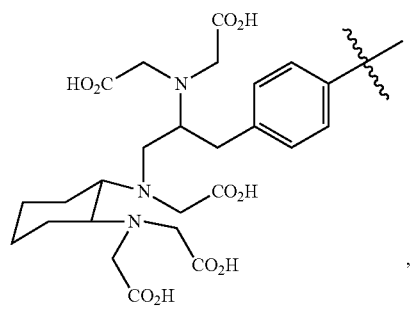
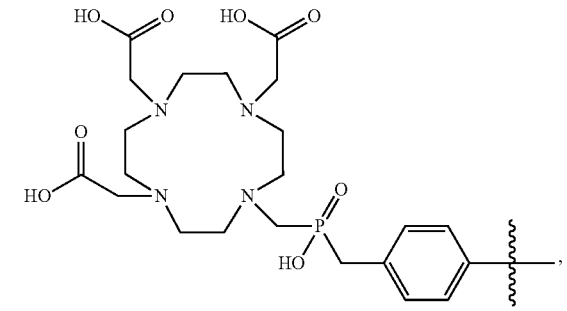
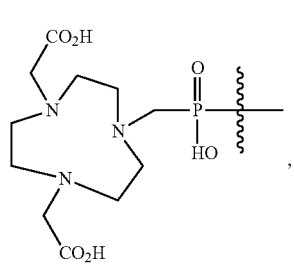
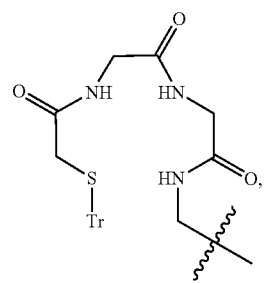
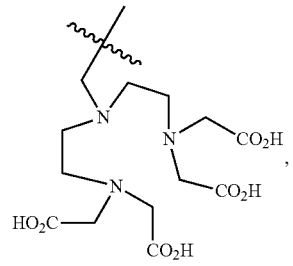

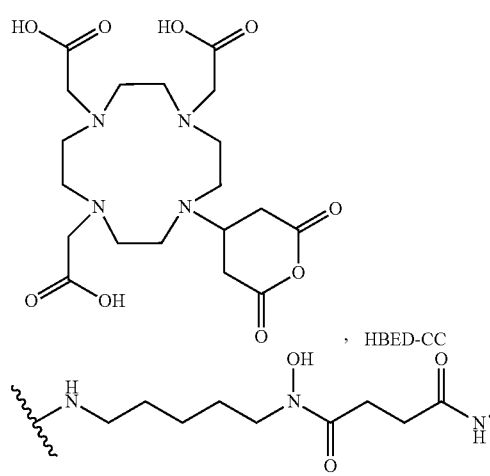

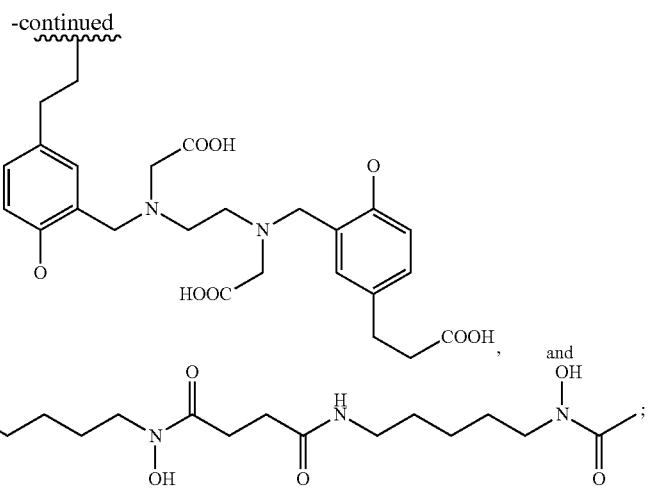

or a pharmaceutically acceptable salt thereof.

8. The compound of claim 7, wherein the metal is selected from the group consisting of: Y, Lu, Tc, Zr, In, Sm, Re, Cu, Pb, Ac, Bi, Al, Ga, Re, Ho and Sc.

9. The compound of claim 7, wherein the radiometal is selected from the group consisting of: $^{68}$Ga, $^{64}$Cu, Al—$^{18}$F, $^{86}$Y, $^{90}$Y, $^{89}$Zr, $^{111}$In, $^{99m}$Tc, $^{177}$Lu, $^{153}$Sm, $^{186}$Re, $^{188}$Re, $^{67}$Cu, $^{212}$Pb, $^{225}$Ac, $^{213}$Bi, $^{212}$Bi, $^{212}$Pb, $^{67}$Ga, $^{203}$Pb, $^{47}$Sc, and $^{166}$Ho.

10. The compound of claim 1, wherein the fluorescent dye moiety comprises carbocyanine, indocarbocyanine, oxacarbocyanine, thiacarbocyanine and merocyanine, polymethine, coumarine, rhodamine, xanthene, fluorescein, borondipyrromethane (BODIPY).

11. The compound of claim 10, wherein the fluorescent dye moiety is selected from the group consisting of:

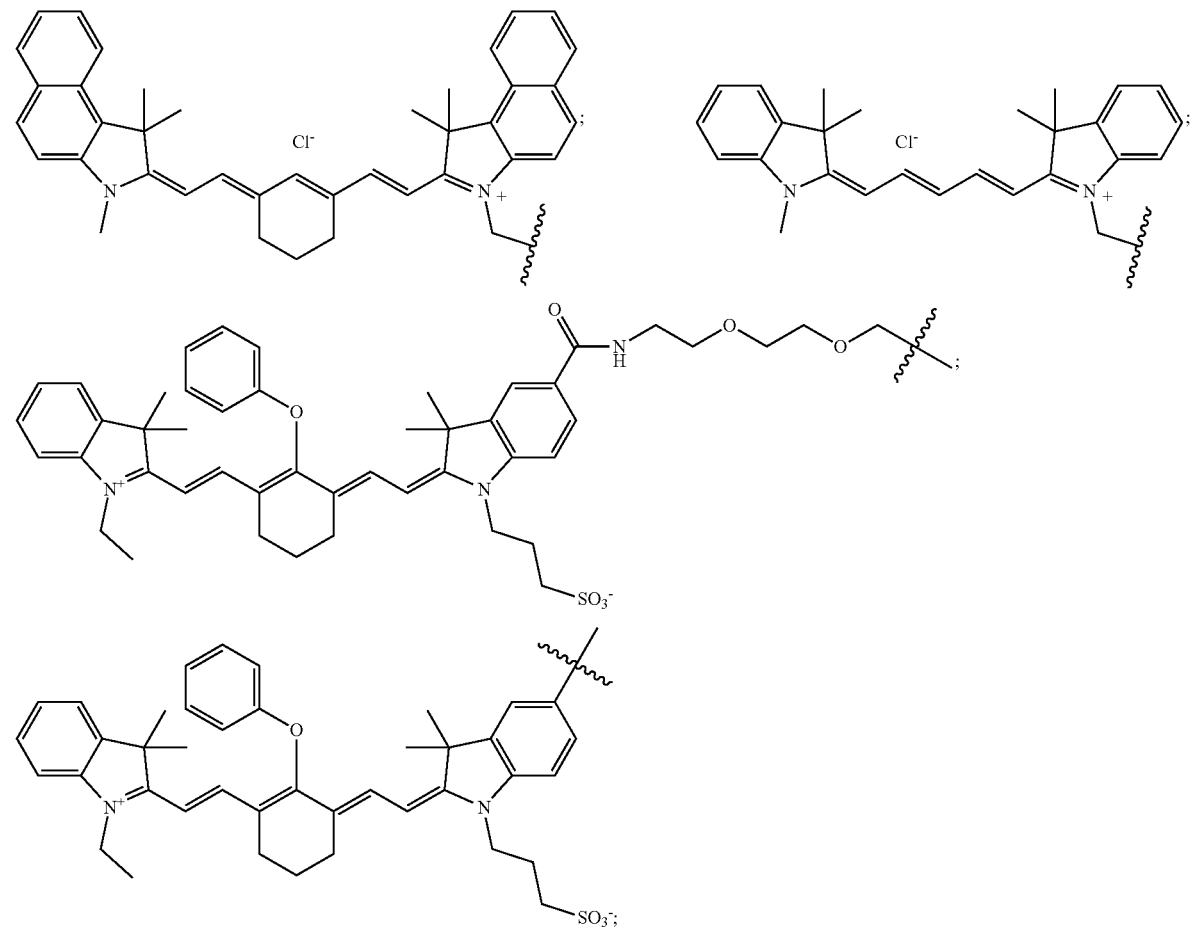

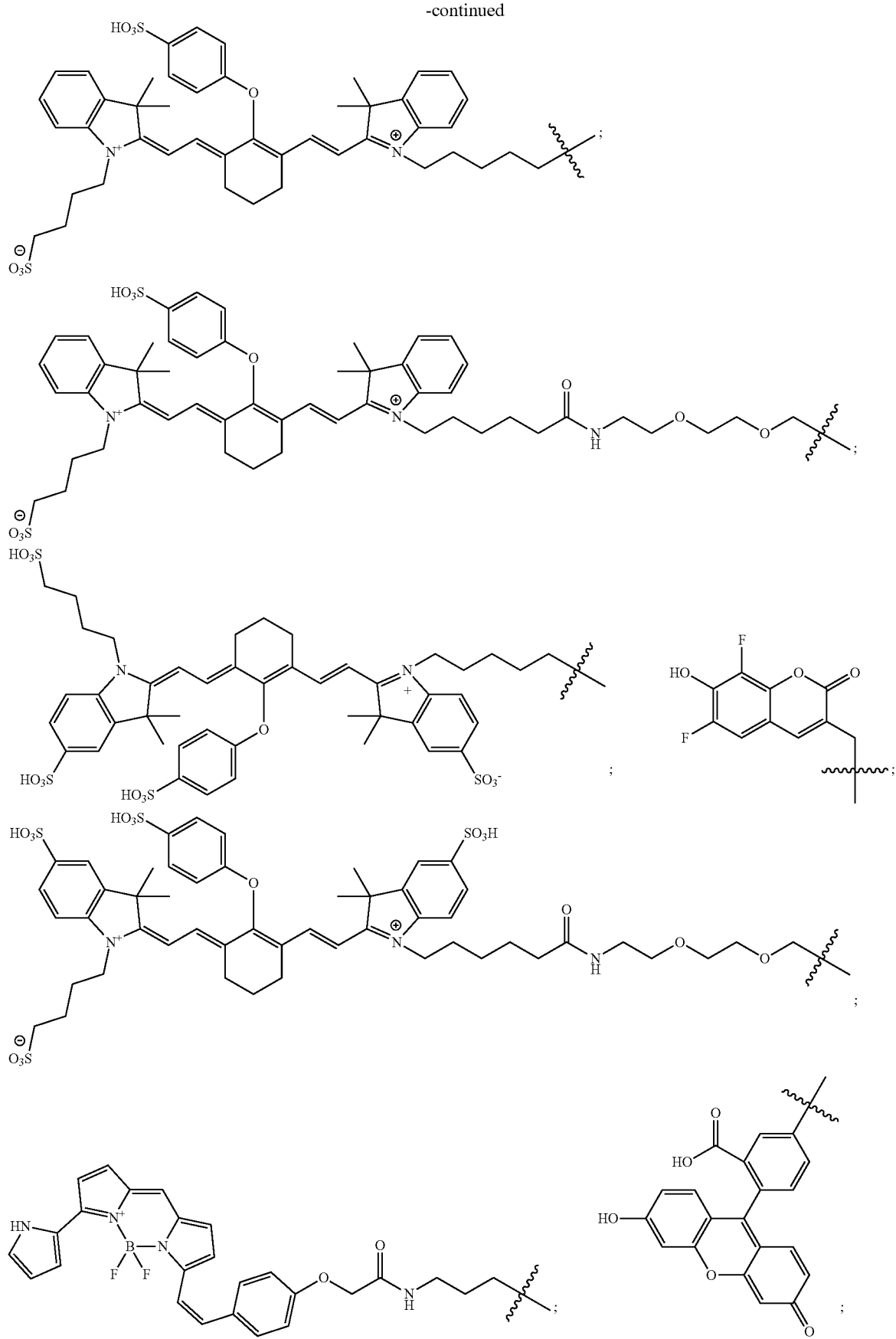

-continued
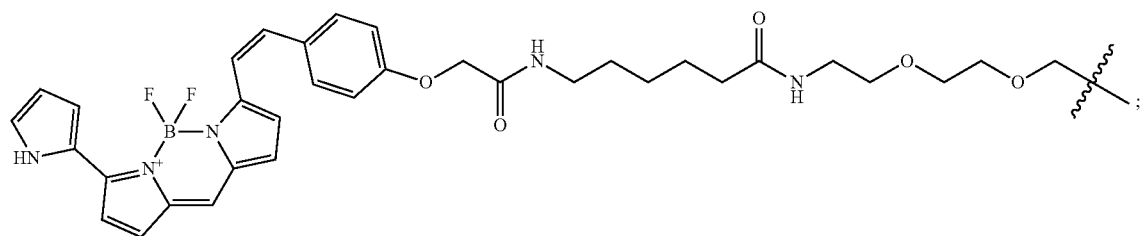
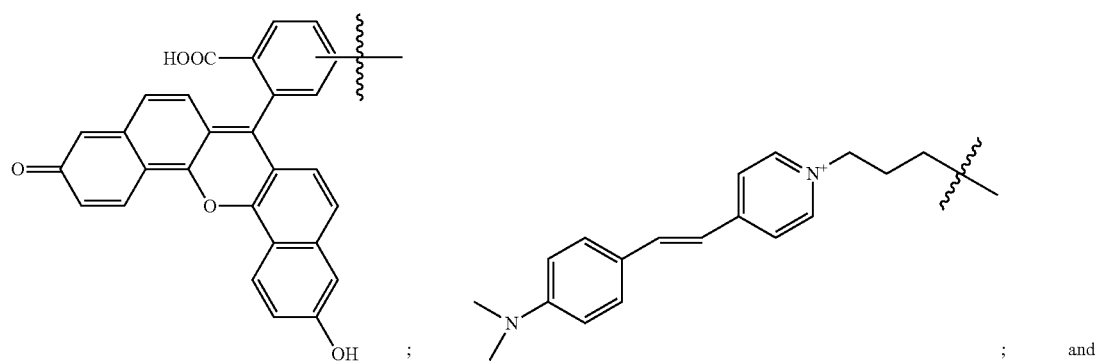
12. The compound of claim 1, wherein the compound of Formula (I) is selected from the group consisting of:
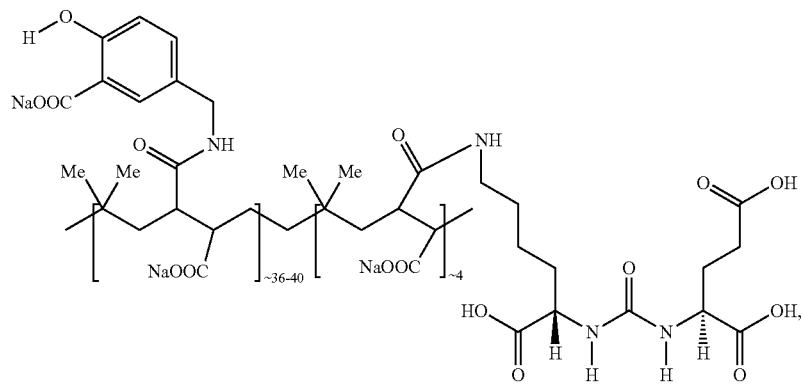

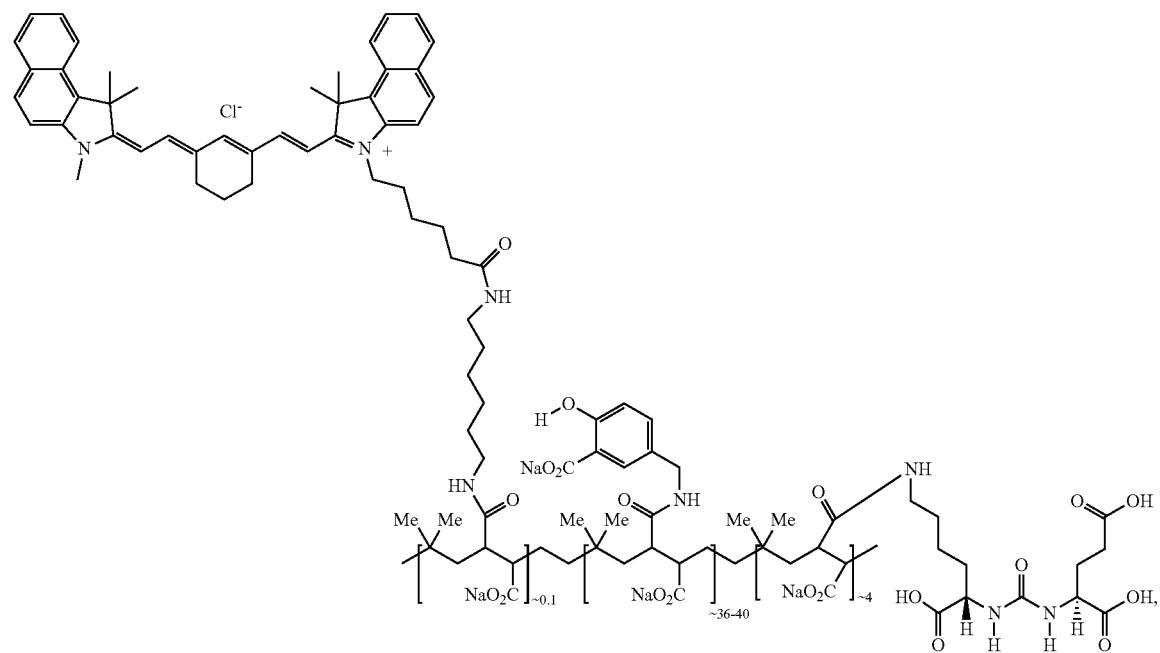
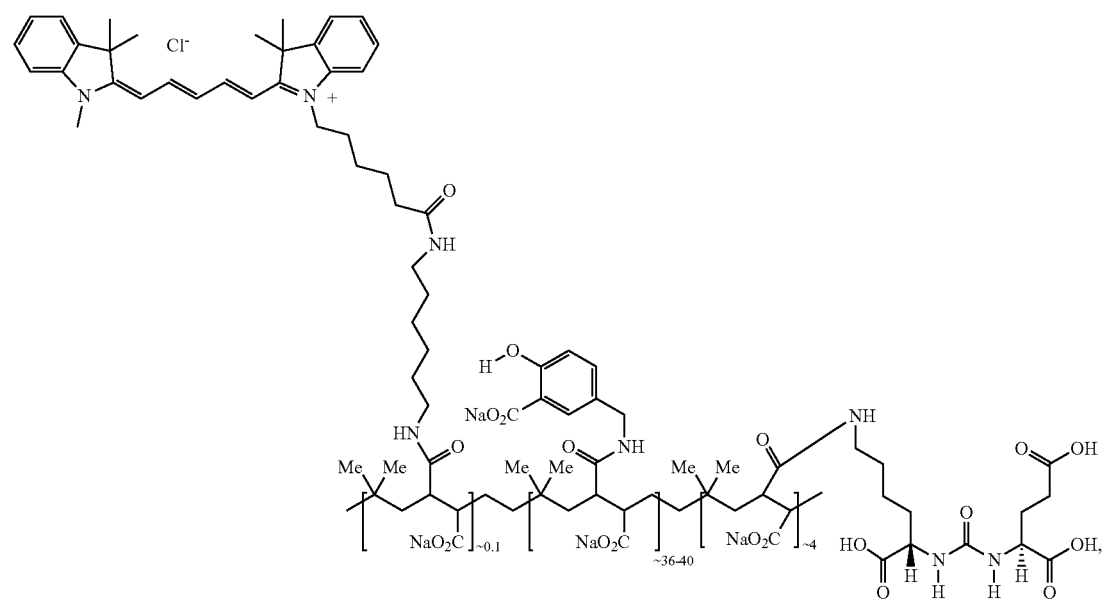

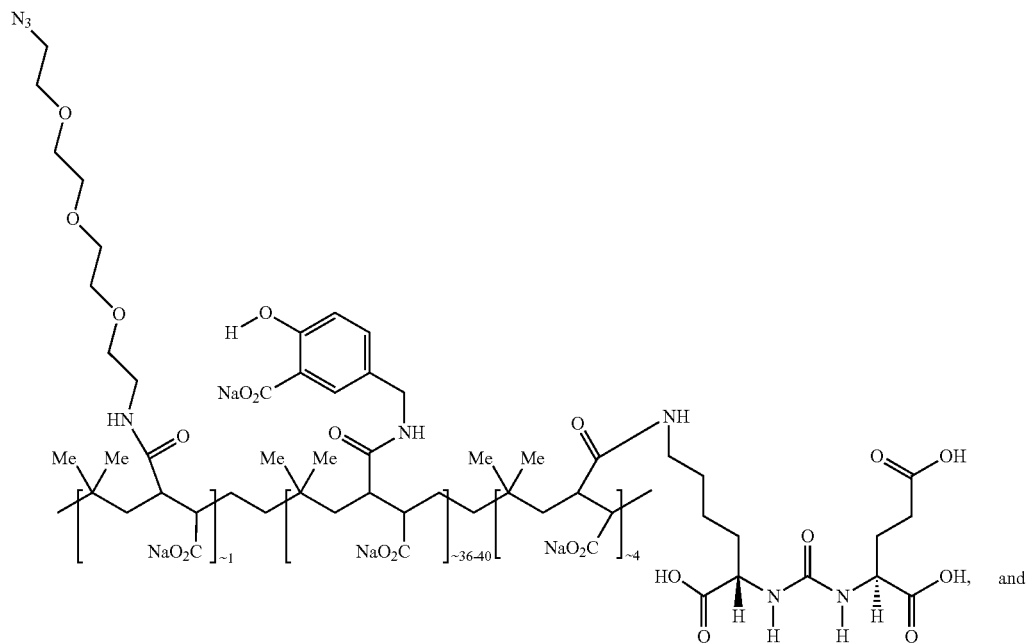
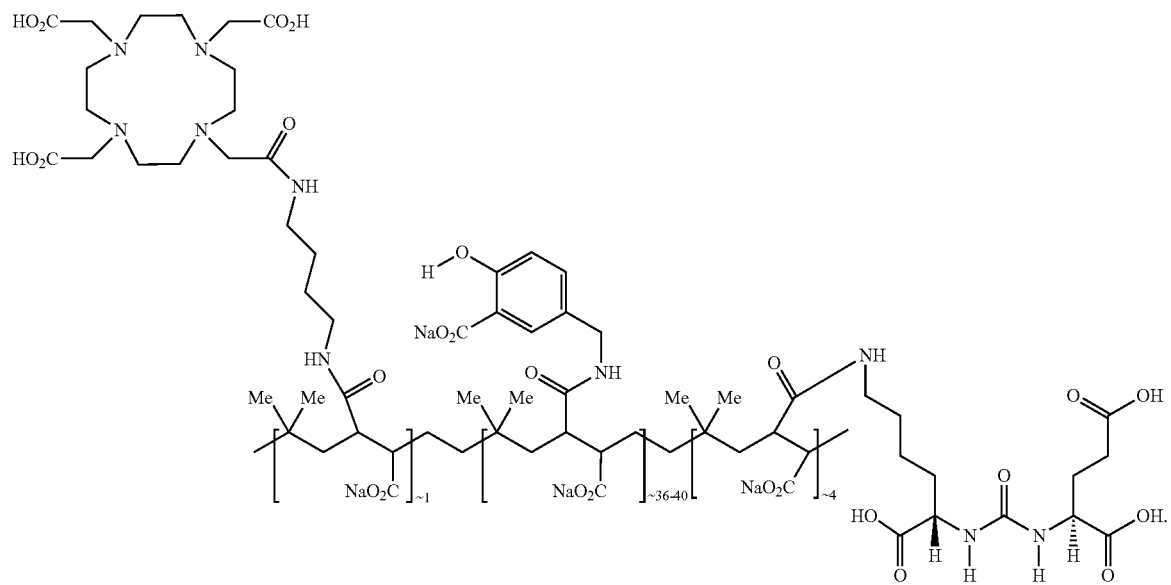

13. The compound of claim 1, wherein the compound of Formula (I) is selected from the group consisting of:

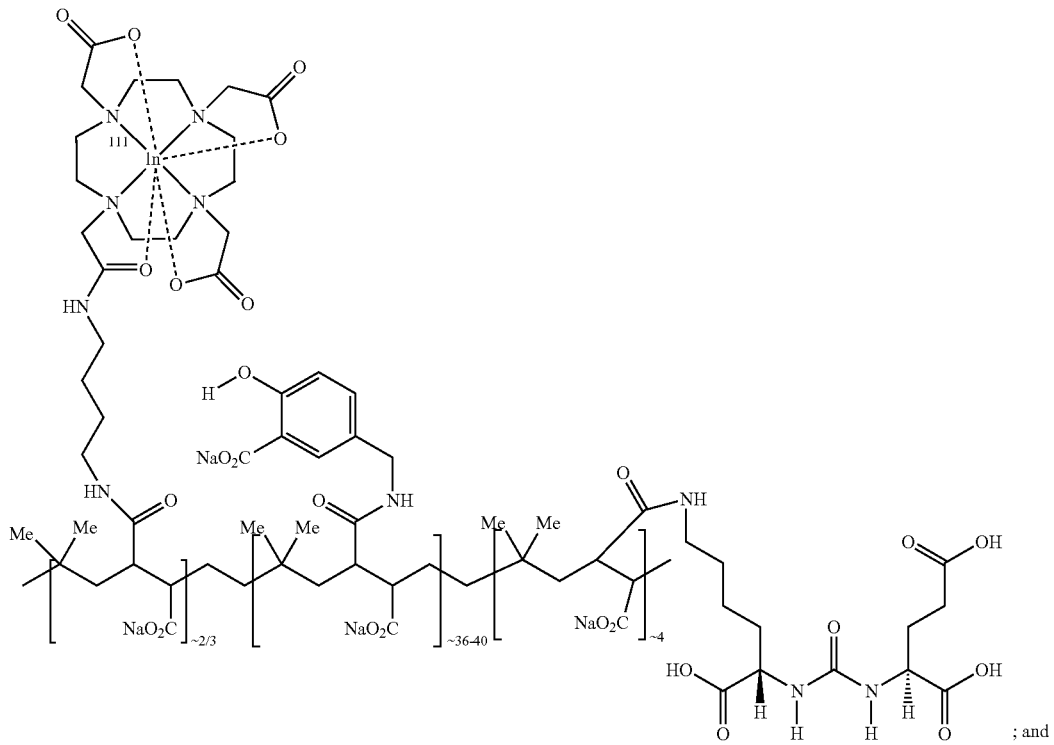

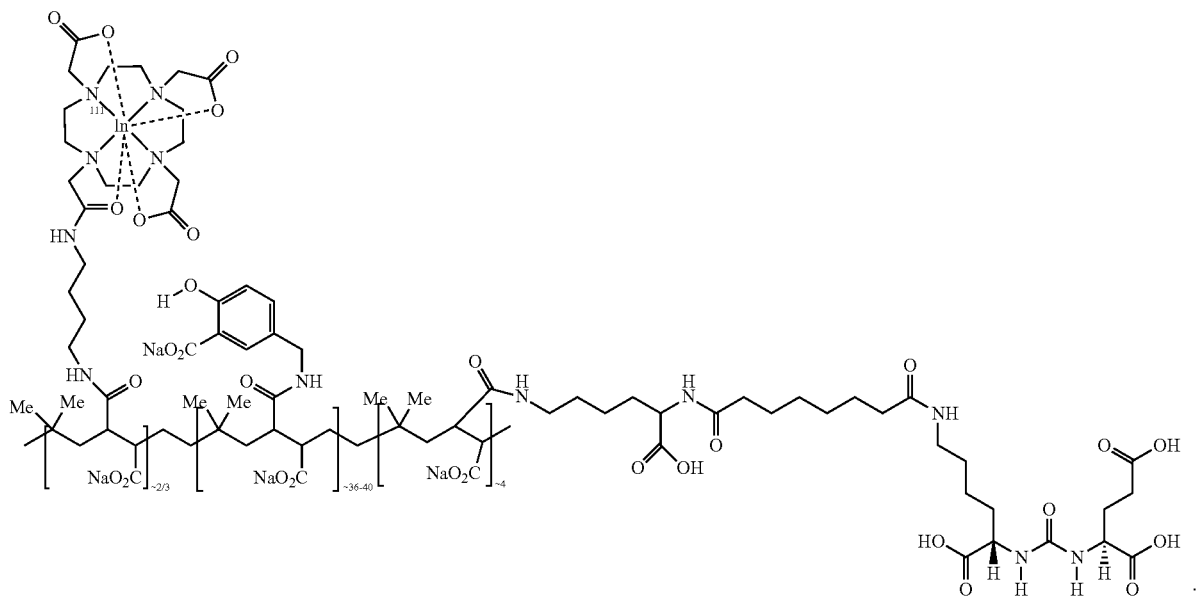

14. A pharmaceutical composition comprising a compound of formula (I) formula (II), (III) and/or (IV), and a pharmaceutically acceptable carrier, diluent or excipient.

15. A method for producing a magnetic resonance imaging (MRI) of one or more PSMA-expressing tumors or cells, the method comprising administering or contacting the one or more PSMA-expressing tumors or cells with an effective amount of a magnetic resonance imaging contrast agent; and imaging the target using a based MRI technique to produce the MR image of the one or more PSMA-expressing tumors or cells, wherein the magnetic resonance imaging contrast agent is a compound of formula (I), formula (II), formula (III), and/or formula (IV), or a pharmaceutical composition of any thereof; the compound of compound of formula (I), formula (II), formula (III), or formula (IV) comprising:

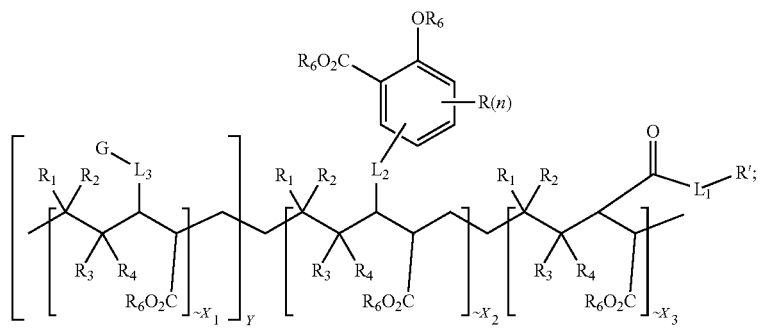
(I)
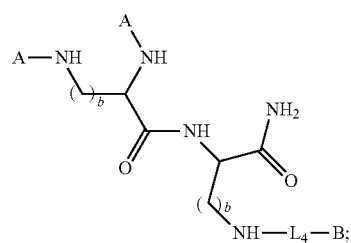
(II)
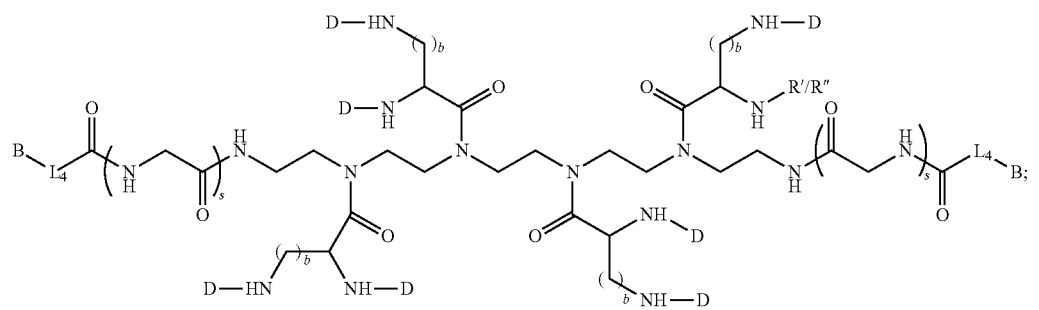
(III)
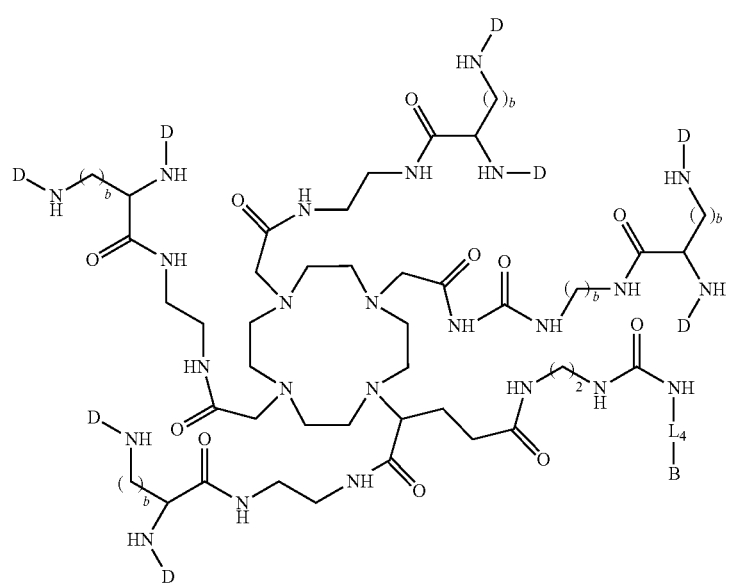
(IV)

wherein:

R' is

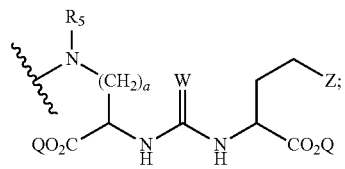

B is R' or

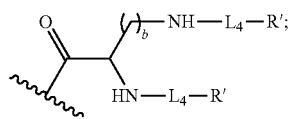

Z is tetrazole or CO₂Q;
Q is H or a protecting group;
W is O or S;
a is an integer selected from the group consisting of 0, 1, 2, 3 and 4;
b is an integer selected from the group consisting of 1, and 4;
n is independently an integer selected from the group consisting of 0, 1, 2, and 3;
s is an integer selected from the group consisting of 0, 1, 2, 3 and 4;
each R is independently selected from the group consisting of hydrogen, substituted or unsubstituted alkyl, alkoxyl, hydroxyl, hydroxyalkyl, carboxyl, acyl, carbonyl, carbamoyl, alkylcarbamoyl, halogen, amino, alkylamino, nitro, nitrile, amide, haloalkyl, aryl, cycloalkyl, aralkyloxyl, and —SO₃H;
R₁, R₂, R₃ and R₄ are independently selected from the group consisting of H or substituted or unsubstituted linear or branched alkyl, substituted or unsubstituted aryl, and alkoxyl;
R₅ is independently H, C₁-C₄ alkyl or C₂-C₁₂ aryl;
each R₆ is independently H, Na or a protecting group;
L₁ is a linking group selected from the group consisting of —(CH₂)ₘ—, —(CH₂—CH₂—O)ₜ—, —(O—CH₂—CH₂)ₜ—, —NR₇—(CHR₈)ₘ—NR₇—C(=O)—(CH₂)ₘ—C(=O)— and —NR₇—(CHR₈)ₘ—C(=O)— NR₇—(CH₂)ₘ—C(=O)—;
L₂ is a linking group selected from the group consisting of —(CH₂)ₘ—NR₇—C(=O)—(CH₂)ₚ—, —(CH₂)ₘ—C(=O)—NR₇—(CH₂)ₚ—, —(CH₂)ₘ—NR₇—C(=O)—NR₇—(CH₂)ₚ—, —(CH₂)ₘ—NR₇—C(=O)—(CH₂)ₚ—, —(CH₂)ₘ—O—C(=O)—NR₇—, —(CH₂)ₘ—O—C(=O)—NR₇—(CH₂)ₚ—, —(CH₂)ₘ—NR₇—C(=O)—O—CH₂)ₚ—, —(CH₂)ₘ—NR₇—C(=O)—O—(CH₂)ₚ—, —SO₂—NH—(CH₂)ₚ—, and —(CH₂)ₘ—SO₂—NH—(CH₂)ₚ—;
L₃ is a linking group selected from the group consisting of —C(=O)—NR₇—(CH₂)ₘ—, —C(=O)—NR₇—(CH₂)ₘ—NR₇—, —C(=O)—NR₇—(CH₂)ₘ—C(=O)—NR₇—, —C(=O)—NR₇—(CH₂)ₘ—NR₇—C(=O)—, —C(=O)—NR₇—(CH₂)ₘ—NR₇—C(=O)—NR₇—(CH₂)ₘ—C(=O)—NR₇—(CH₂)ₚ—, —C(=O)—NR₇—(CH₂)ₘ—(O—CH₂—CH₂)ₜ—, —C(=O)— NR₇—(CH₂)ₘ—(CH₂—CH₂—O)ₜ—(CH₂)ₚ—, and —C(=O)—NR₇—(CH₂)ₘ—(O—CH₂—CH₂)ₜ—C(=O)—NR₇—;

L₄ is a linking group selected from the group consisting of —(CH₂)ₘ—, —C(=O)—(CH₂)ₘ—C(=O)—, —C(=O)—(CH₂)ₘ—NR₇—C(=O)—, —C(=O)—(CH₂—CH₂—O)ₜ—C(=O)—, —C(=O)—(CHR₈)ₘ—C(=O)—, —C(=O)—(CHR₈)ₘ—NR₇—C(=O)—, —C(=O)—(CH₂—CH₂—O)ₜ—C(=O)—, and —C(=O)—(O—CH₂—CH₂)ₜ—C(=O)—;
each R₇ is independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;
each R₈ is independently selected from the group consisting of hydrogen, and —COOR₆;
m and p are each independently an integer selected from the group consisting of 0, 1, 2, 3, 4, 5, 6, 7 and 8;
t is an integer selected from the group consisting of 1, 2, 3, 4, 5, 6, 7, 8, 9, 10, 11 and 12;
Y is an integer selected from the group consisting of 0 and 1;
G is an azide, an alkyne, a fluoerescent dye moiety that emits light in the visible or near-infrared (NIR) spectrum, or a chelating moiety optionally comprising a metal or a radiometal;
X₁ is an integer selected from the group consisting of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and 2;
X₂ and X₃ are each independently an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40;
A is selected from the group consisting of:

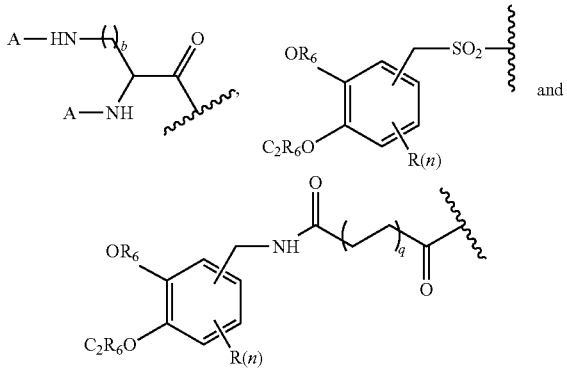

wherein q is an integer selected from the group consisting of 1, 2, 3, 4, and 5;
D is selected from the group consisting of:

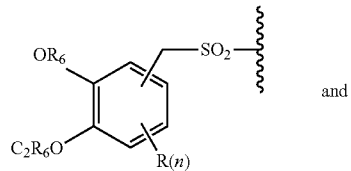

-continued
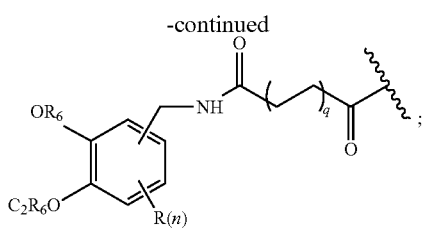
or a salt or a stereoisomer thereof.
16. The method of claim 15, wherein R' is
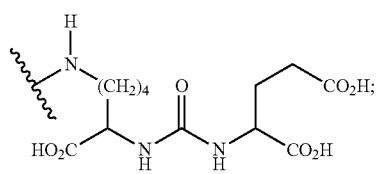
and
B is R' or
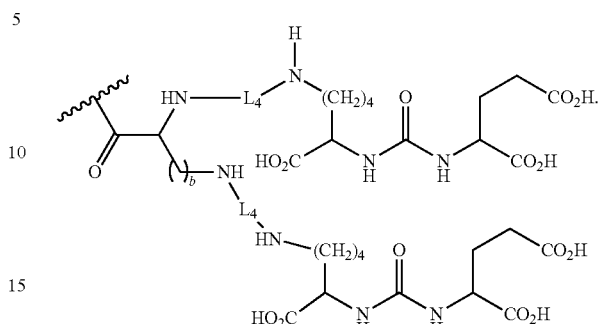
17. The method of claim 15, wherein the compound of formula (II) is selected from the group consisting of:
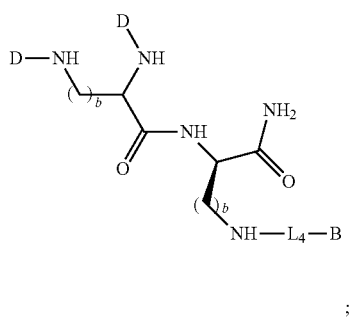
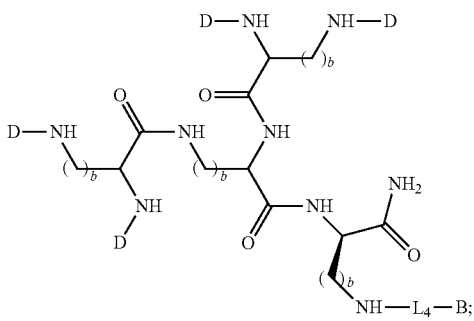
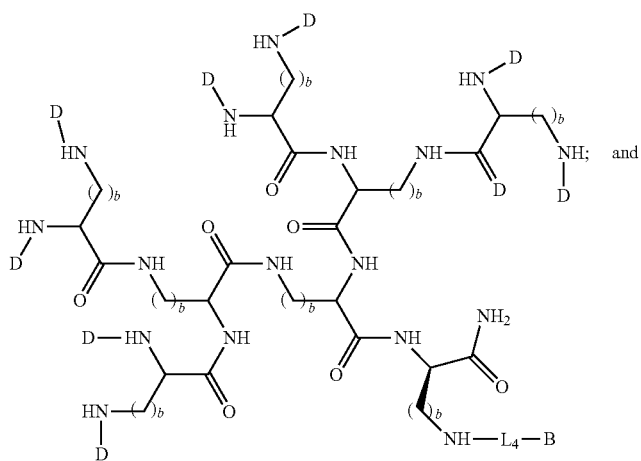

-continued
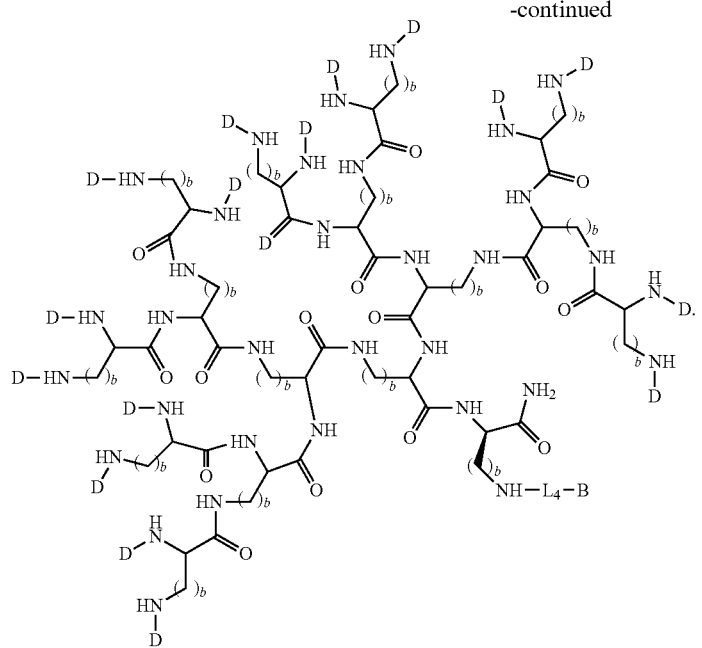
18. The method of claim 15, wherein the ratio of $X_2:X_3$ is about 10:1.
19. The method of claim 15, wherein the ratio of $X_1:X_2:X_3$ is about 0.1:10:1.
20. The method of claim 15, wherein the ratio of $X_1:X_2:X_3$ is about 1:10:1.
21. The method of claim 15, wherein the chelating moiety comprising a metal or a radiometal, is selected from the group consisting of:
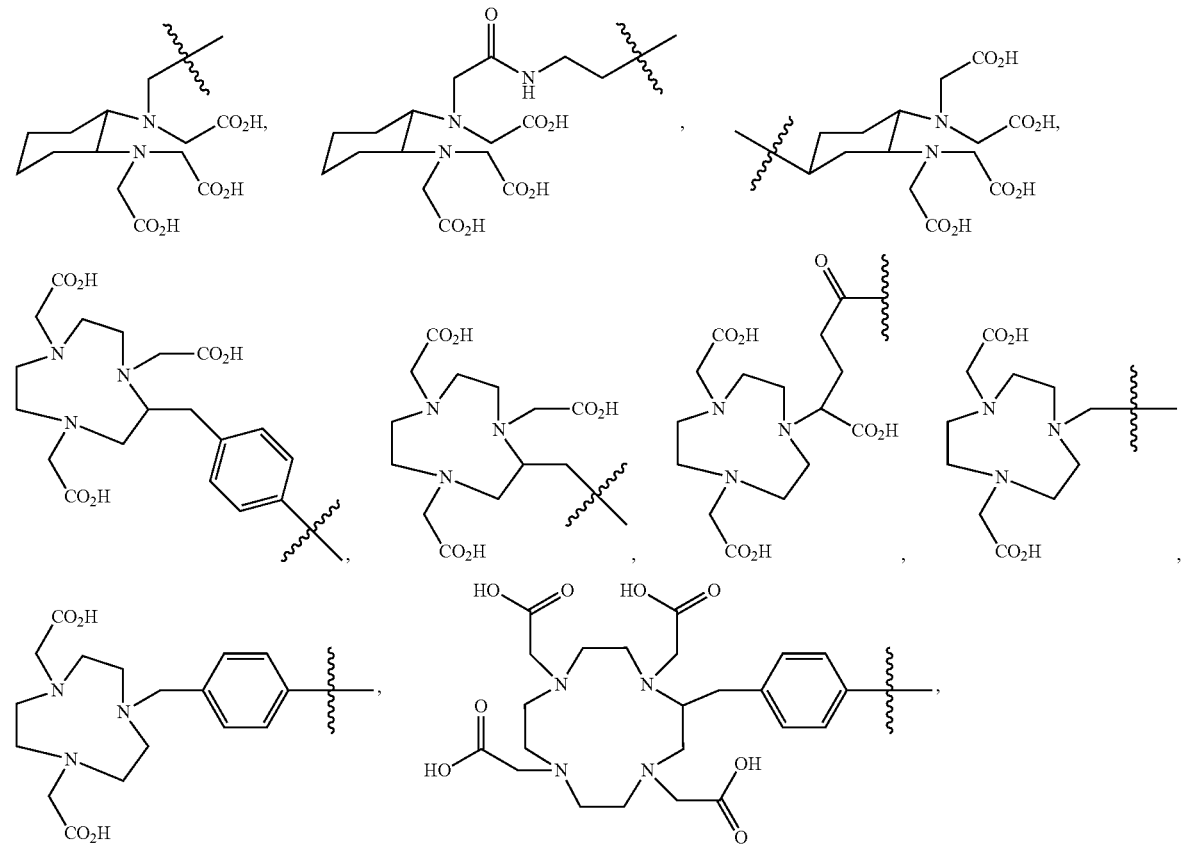

-continued
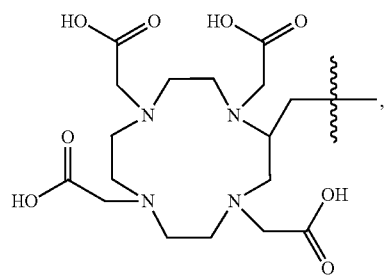
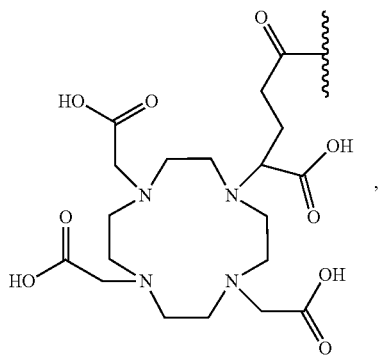
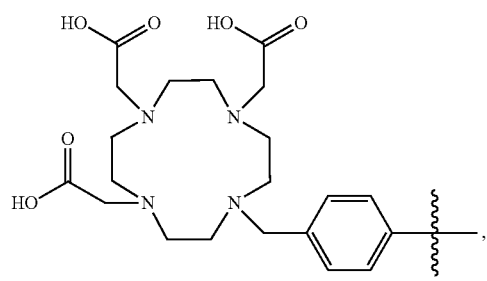
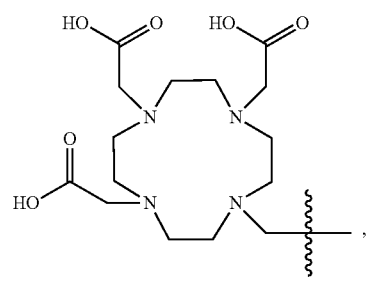
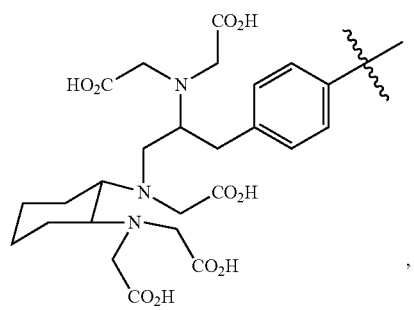
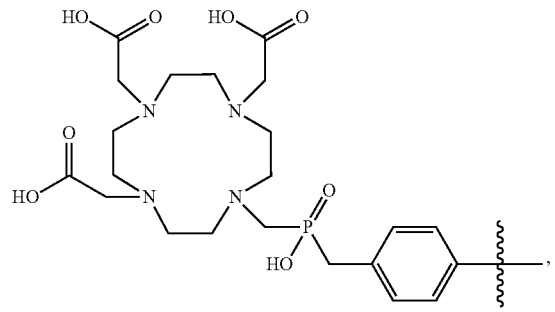
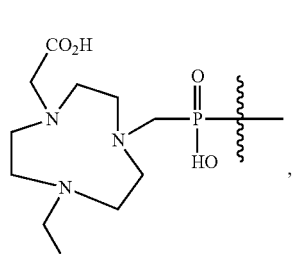
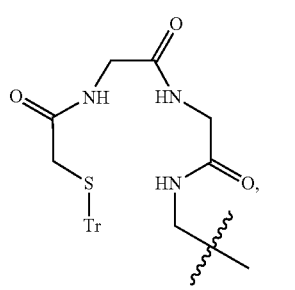
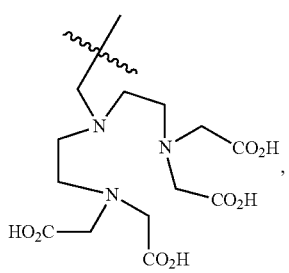
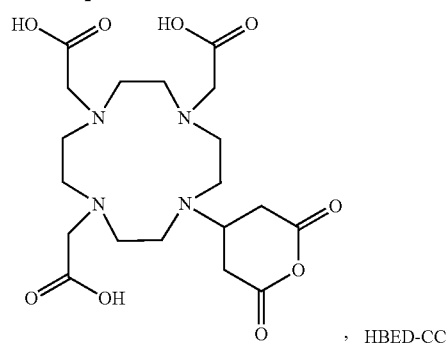, HBED-CC
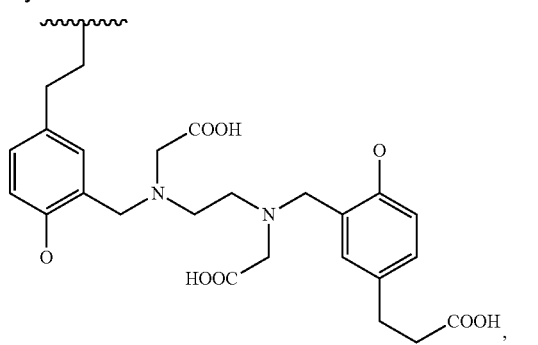, and

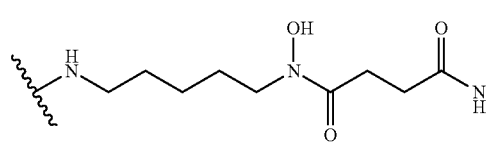

or a pharmaceutically acceptable salt thereof.

22. The method of claim 21, wherein the metal is selected from the group consisting of: Y, Lu, Tc, Zr, In, Sm, Re, Cu, Pb, Ac, Bi, Al, Ga, Re, Ho and Sc.

23. The method of claim 21, wherein the radiometal is selected from the group consisting of: $^{68}$Ga, $^{64}$Cu, Al-$^{18}$F, $^{86}$Y, $^{90}$Y, $^{89}$Zr, $^{111}$In, $^{99m}$Tc, $^{177}$Lu, $^{153}$Sm, $^{186}$Re, $^{188}$Re, $^{67}$Cu, $^{212}$Pb, $^{225}$Ac, $^{213}$Bi, $^{212}$Bi, $^{212}$Pb, $^{67}$Ga, $^{203}$Pb, $^{47}$Sc, and $^{166}$Ho.

24. The method of claim 15, wherein the NIR dye is selected from the group consisting of: wherein the fluorescent dye moiety comprises carbocyanine, indocarbocyanine, oxacarbocyanine, thiacarbocyanine and merocyanine, polymethine, coumarine, rhodamine, xanthene, fluorescein, boron-dipyrromethane (BODIPY).

25. The method of claim 24, wherein the fluorescent dye moiety is selected from the group consisting of:

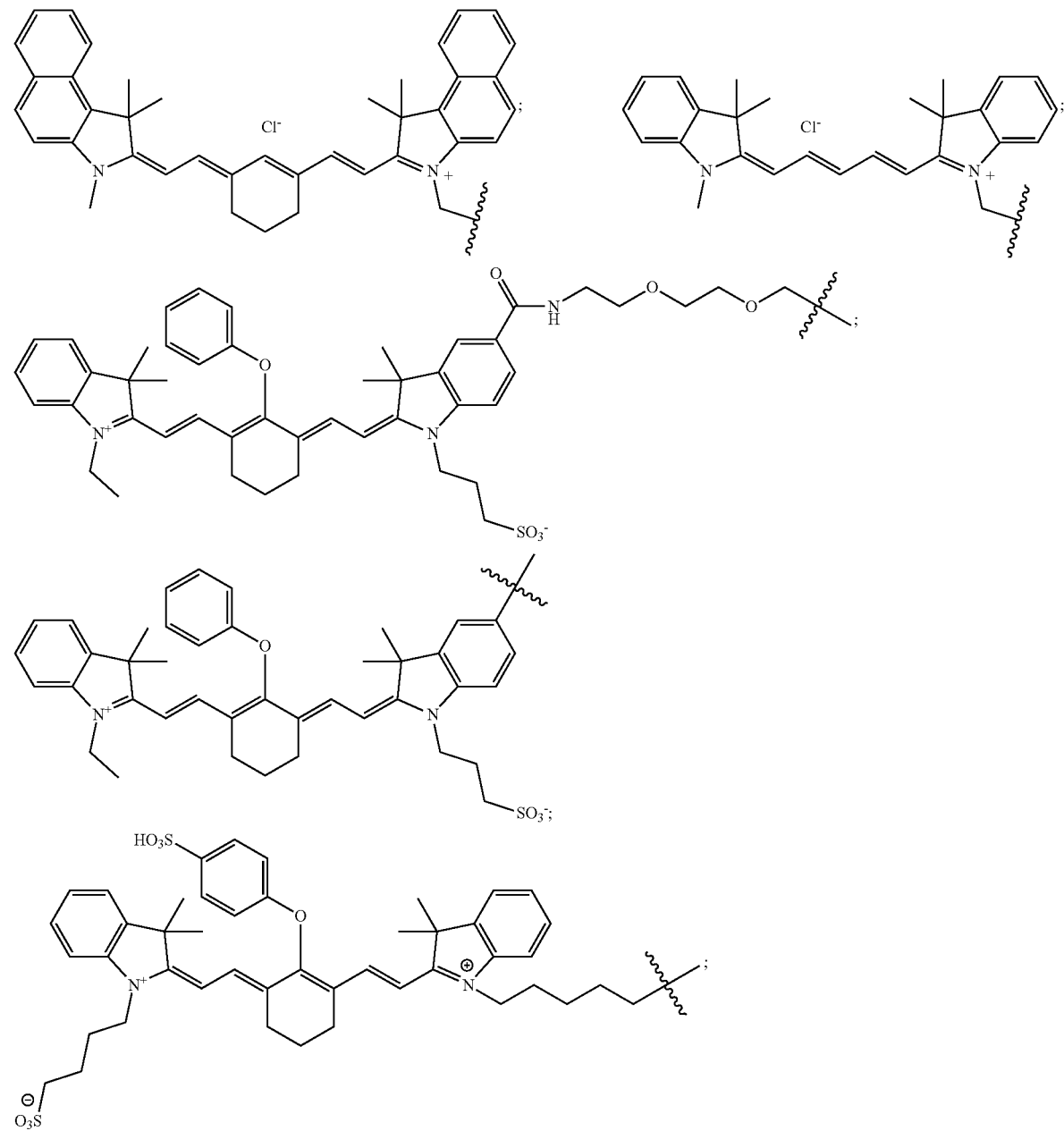

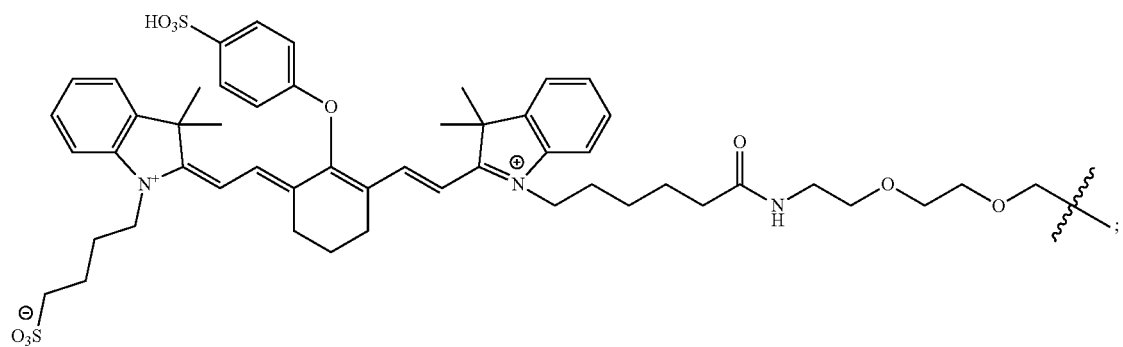
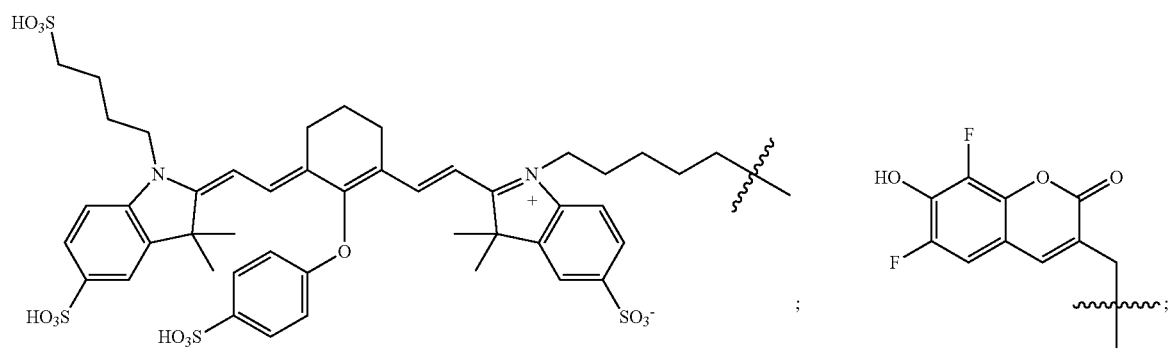
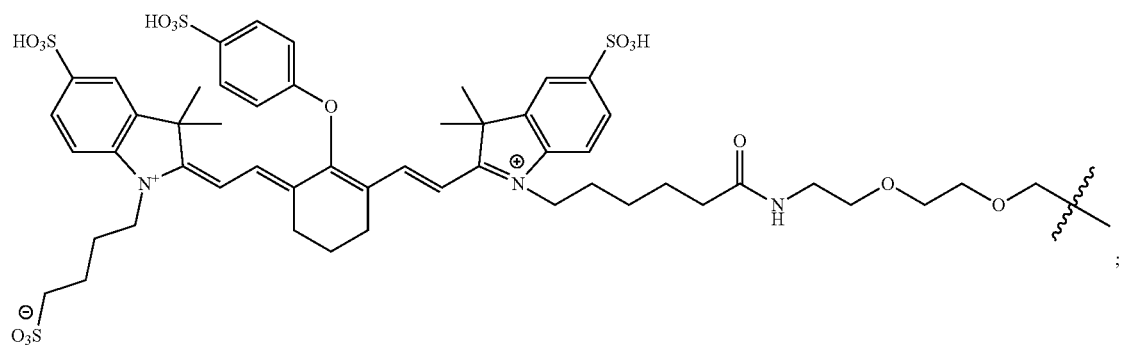
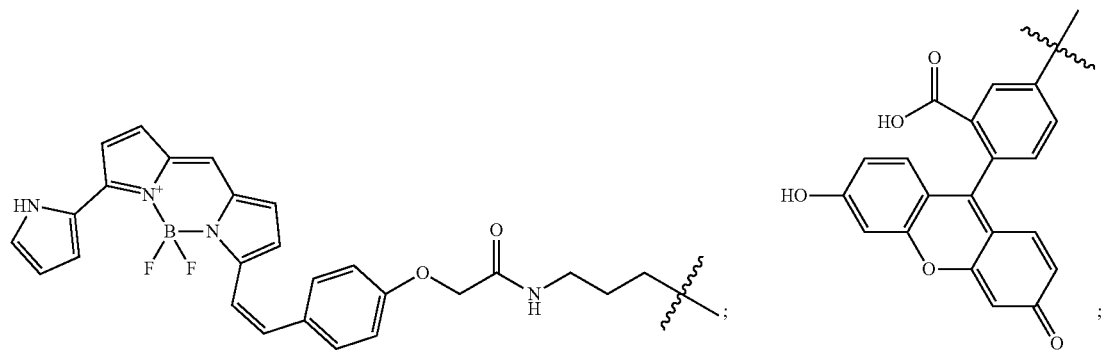

-continued
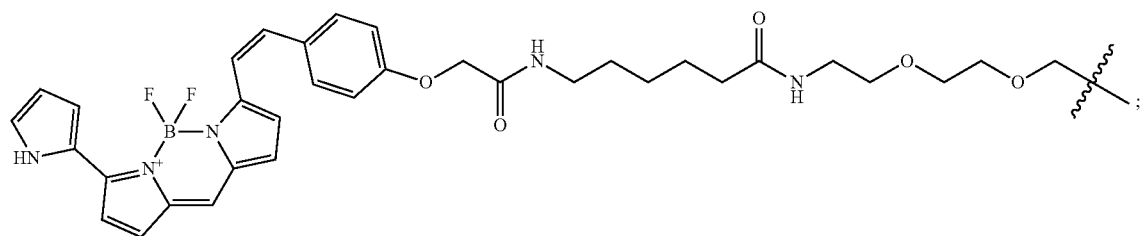
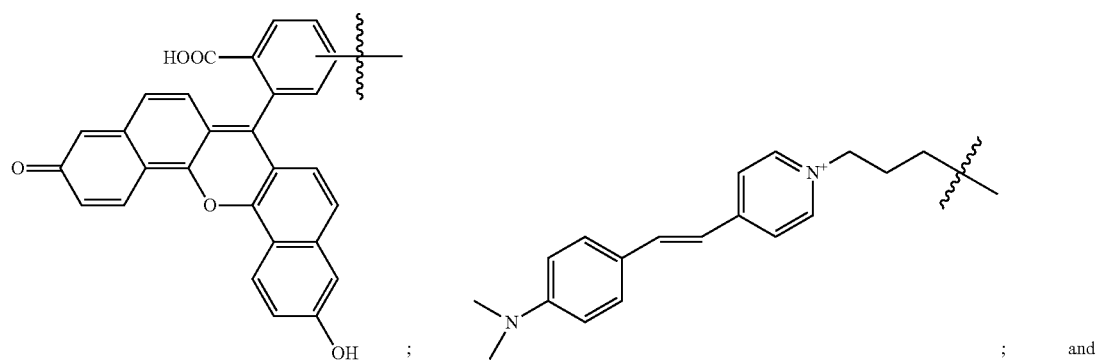
26. The method of claim 15, wherein the compound of Formula (I) is selected from the group consisting of:
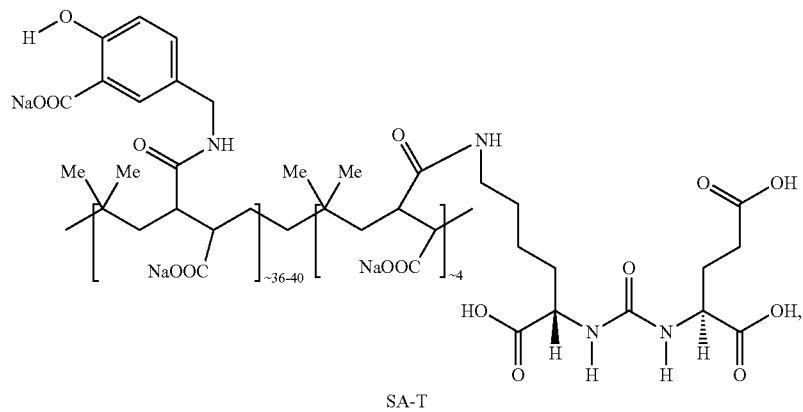
SA-T

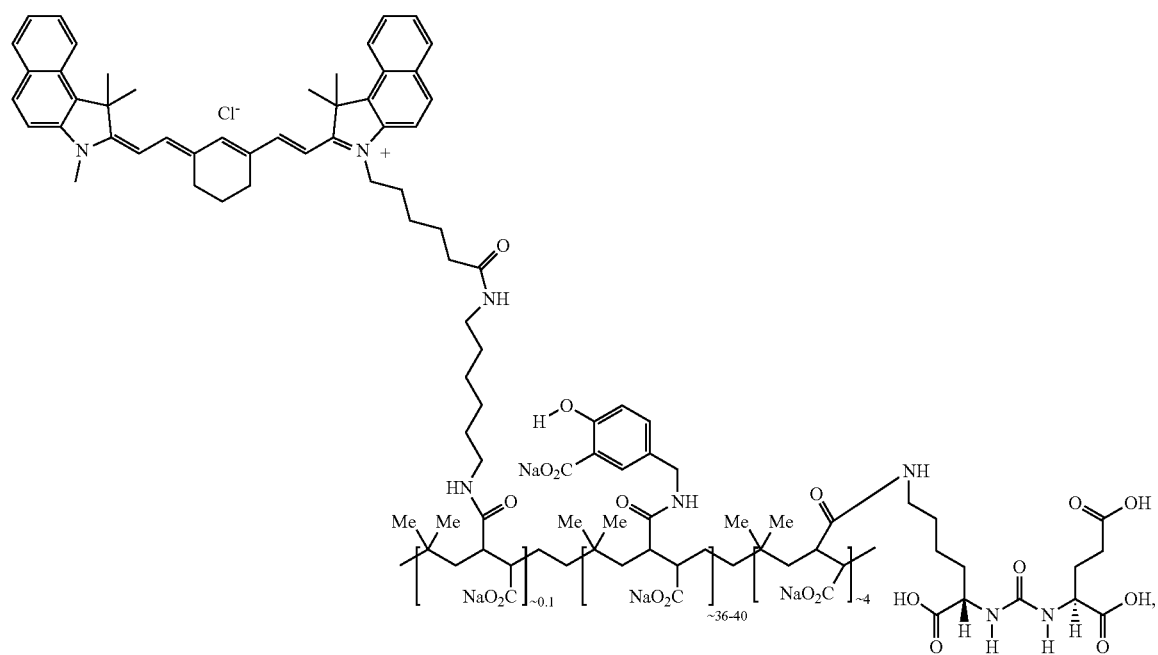
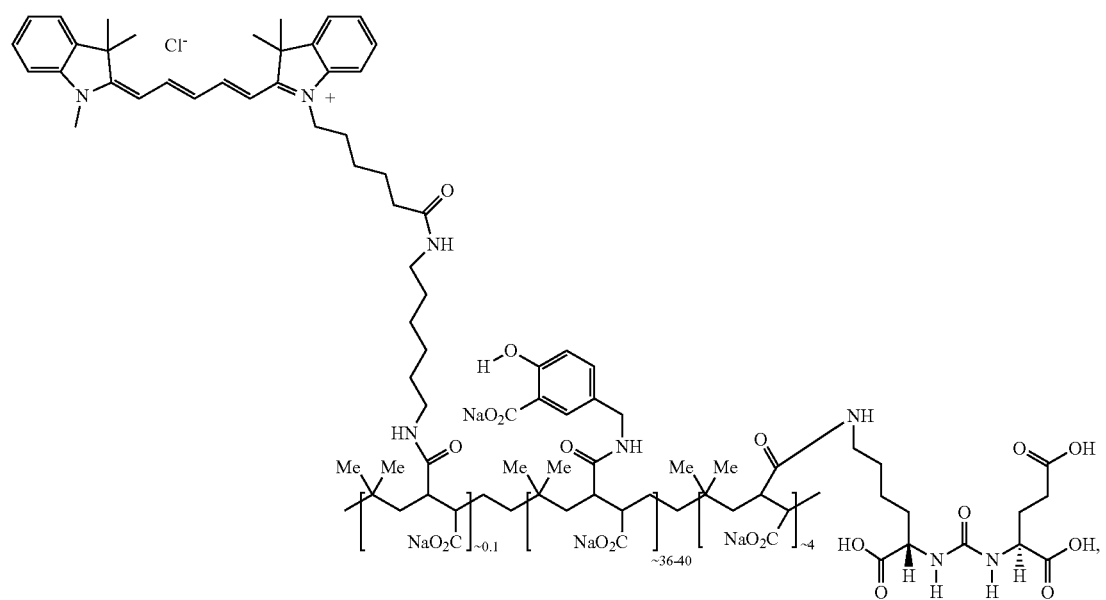

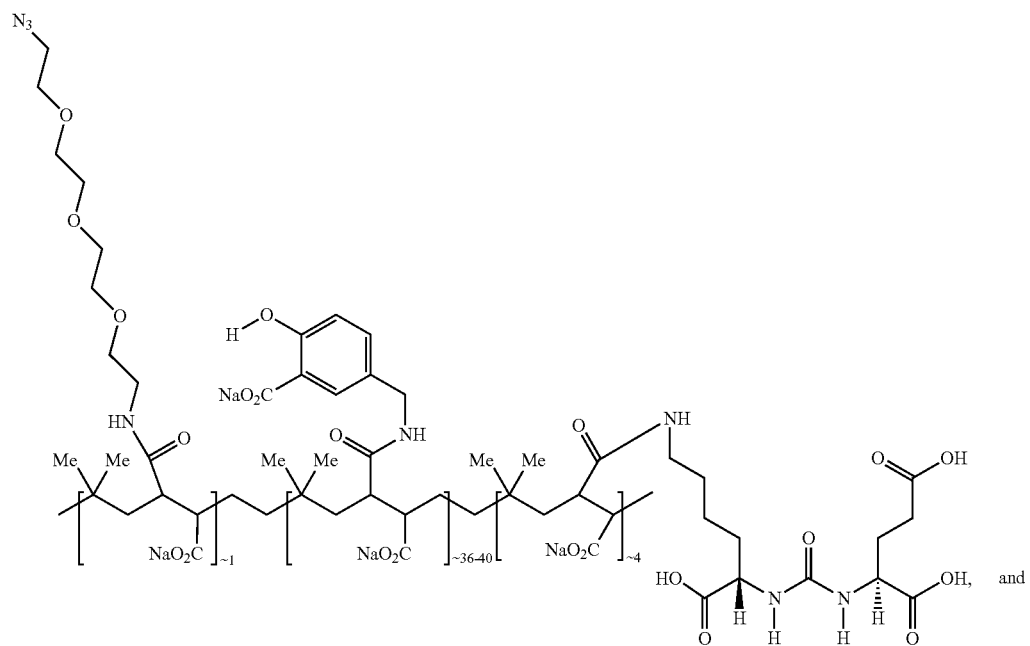
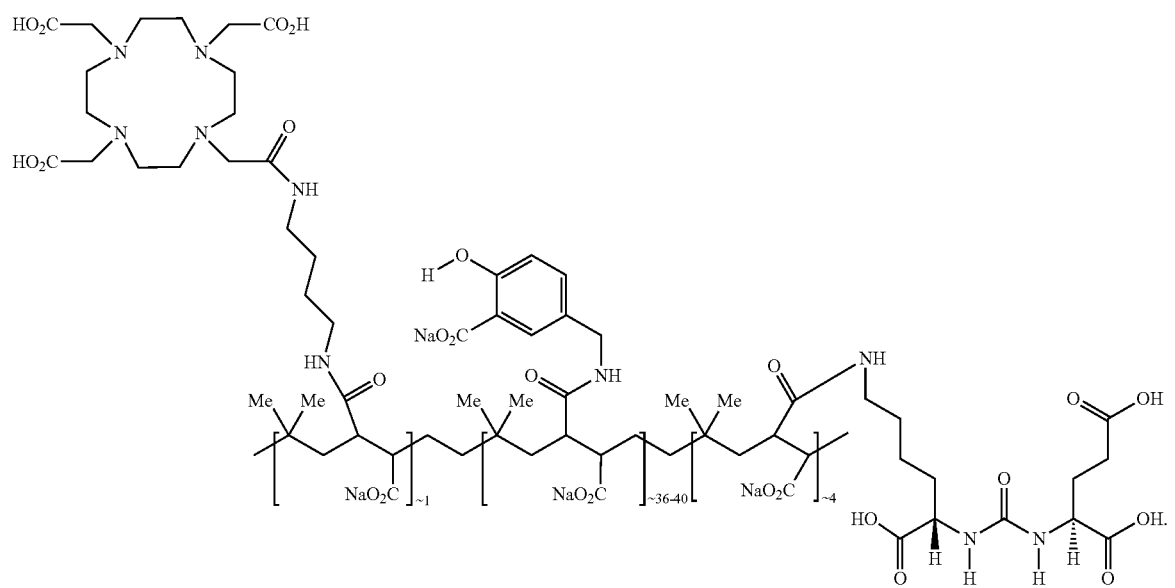

27. The method of claim 15, wherein the compound of Formula (I) is selected from the group consisting of:

31. The method of claim 15, wherein the one or more PSMA-expressing tumors or cells is present in a subject.

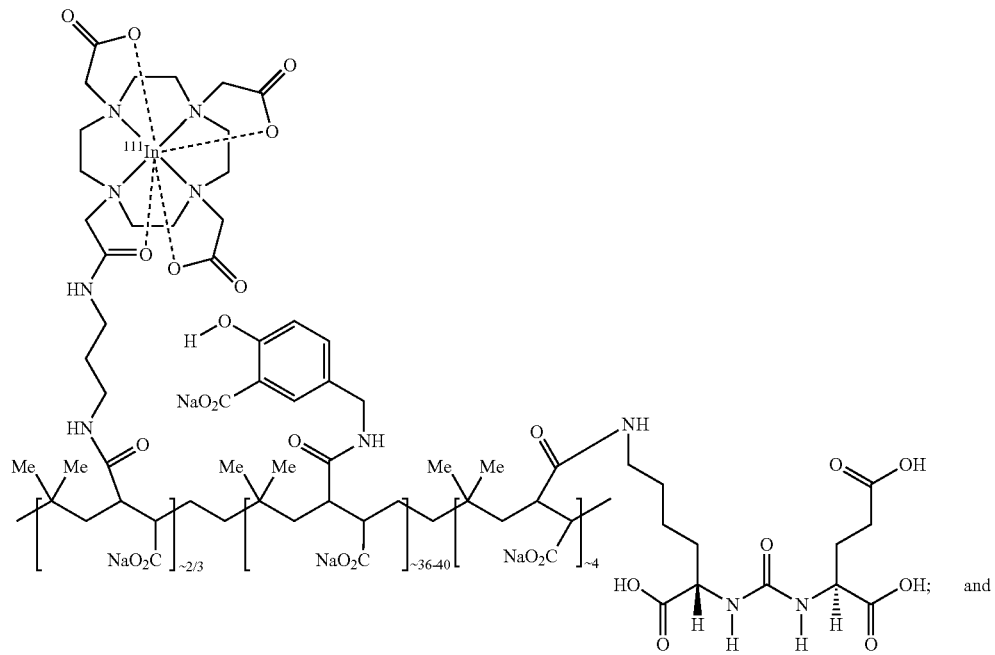

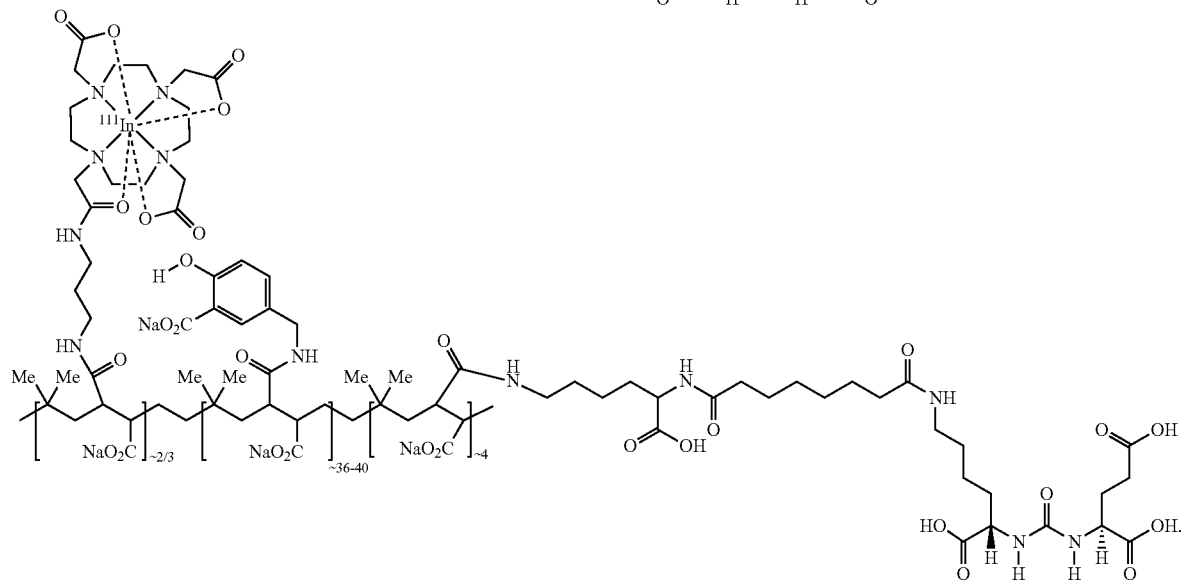

28. The method of claim 15, wherein the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

29. The method of claim 15, wherein the one or more PSMA-expressing tumors or cells is a prostate tumor or cell.

30. The method of claim 15, wherein the one or more PSMA-expressing tumors or cells is in vitro, in vivo, or ex vivo.

32. The method of claim 15, further comprising measuring a chemical shift change of exchangeable protons in said MM contrast agent.

33. The method of claim 15, wherein the one or more PSMA-expressing tumors or cells is imaged using CEST MRI.

34. The method of claim 15, wherein the one or more PSMA-expressing tumors or cells is imaged using FLEX MRI.

35. The method of claim 15, further comprising diagnosing, based on the MR image of the one or more PSMA-expressing tumors or cells, a disease or condition in a subject.

36. The method of claim 15, further comprising monitoring, based on the MR image of the one or more PSMA-expressing tumors or cells, progression or regression of a disease or condition in a subject.

37. The method of claim 15, further comprising treating a disease or condition in a subject in need thereof.

38. The method of claim 35, wherein the disease or condition is selected from the group consisting of prostate cancer, hormone-refractory disease, metastatic diseases and tumor neovasculature.

39. The method of claim 15, wherein the MR imaging is performed in combination with positron emission tomography (PET).

40. The method of claim 15, wherein the MR imaging is performed in combination with single-photon emission computed tomography (SPECT).

* * * * *

UNITED STATES PATENT AND TRADEMARK OFFICE
CERTIFICATE OF CORRECTION

PATENT NO. : 10,688,198 B2
APPLICATION NO. : 15/764316
DATED : June 23, 2020
INVENTOR(S) : Sangeeta Ray et al.

It is certified that error appears in the above-identified patent and that said Letters Patent is hereby corrected as shown below:

In the Claims

Column 87, Claim 11, the first compound reads:

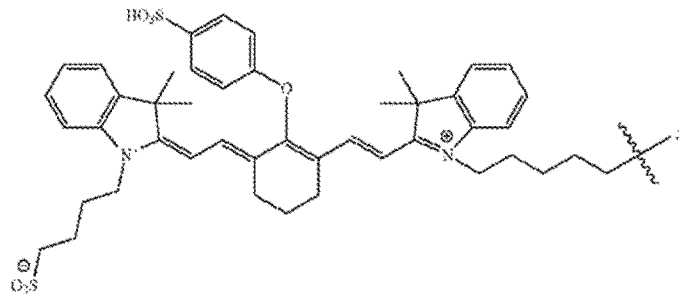

Whereas it should read:

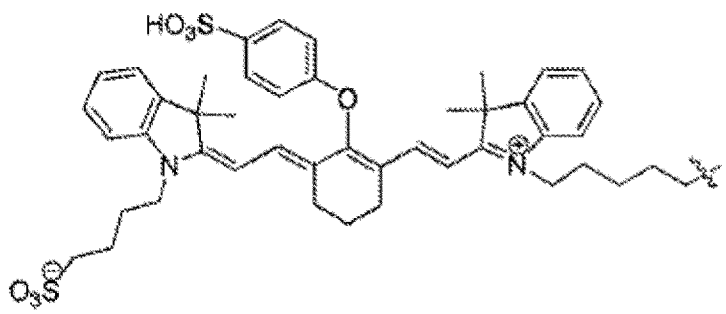

Signed and Sealed this
Tenth Day of November, 2020

Andrei Iancu
*Director of the United States Patent and Trademark Office*

Column 87, Claim 11, the second compound reads:
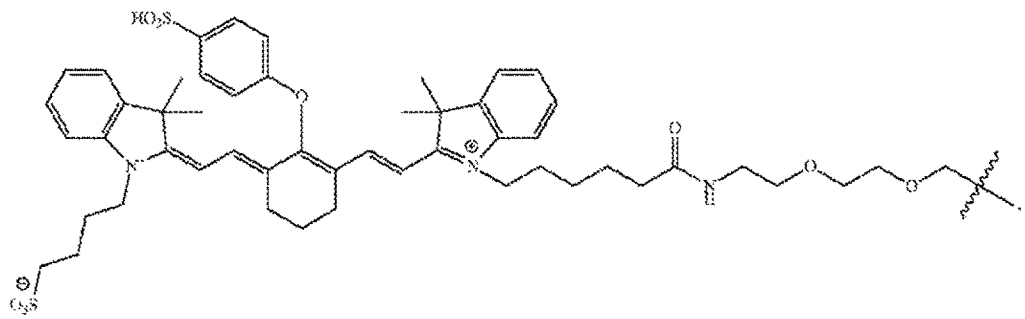
Whereas it should read:
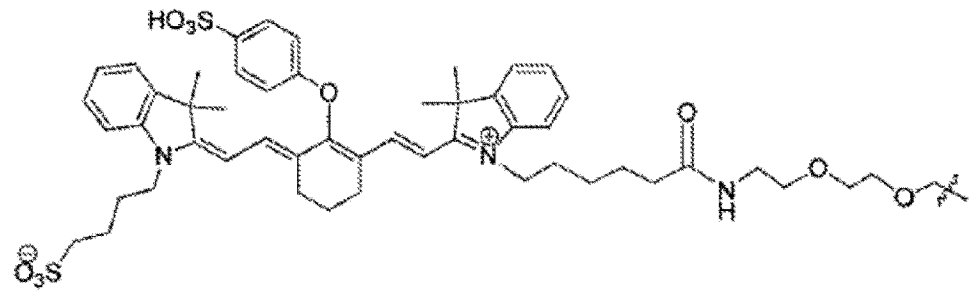
Column 87, Claim 11, the fourth compound reads:
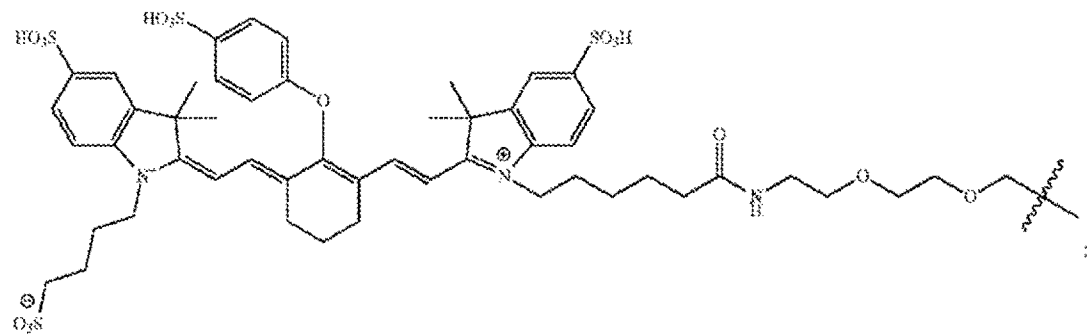
Whereas it should read:
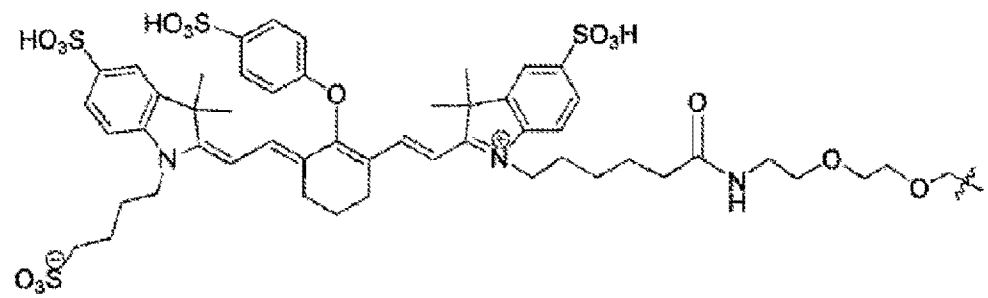

CERTIFICATE OF CORRECTION (continued)
U.S. Pat. No. 10,688,198 B2

Column 107, Claim 25, the fourth compound reads:

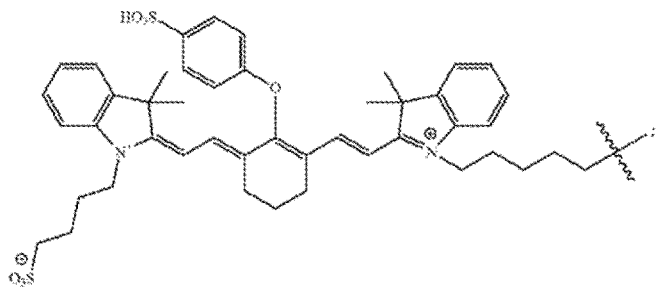

Whereas it should read:

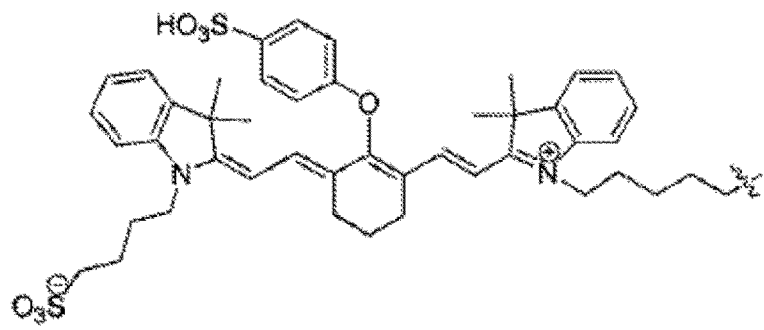

Column 109, Claim 25, the first compound reads:

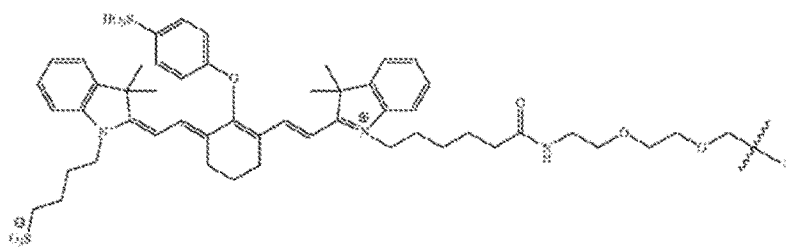

Whereas it should read:

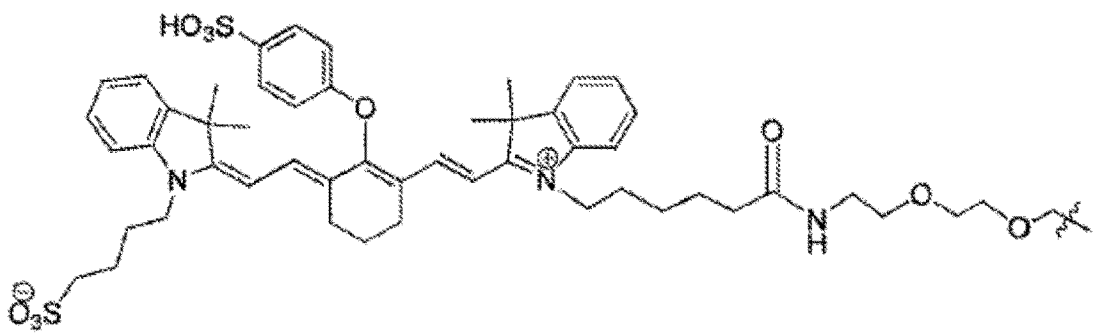

Column 109, Claim 25, the third compound reads:

CERTIFICATE OF CORRECTION (continued)
U.S. Pat. No. 10,688,198 B2

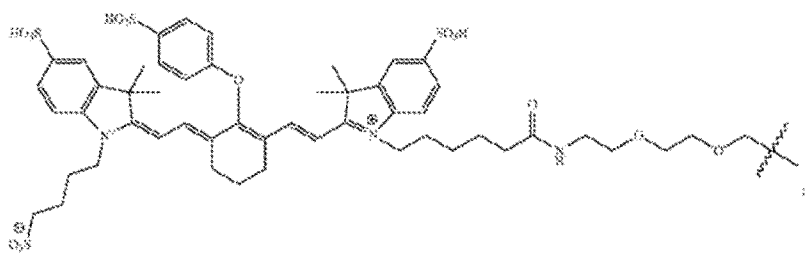

Whereas it should read: